US010934291B2

(12) United States Patent
Haystead et al.

(10) Patent No.: US 10,934,291 B2
(45) Date of Patent: Mar. 2, 2021

(54) KINASE INHIBITORS AND RELATED METHODS OF USE

(71) Applicants: Duke University, Durham, NC (US); UTI Limited Partnership, Calgary (CA)

(72) Inventors: Timothy A. J. Haystead, Chapel Hill, NC (US); David A. Carlson, Durham, NC (US); Douglas H. Weitzel, Durham, NC (US); Justin A. MacDonald, Calgary (CA); Michael P. Walsh, Calgary (CA)

(73) Assignees: Duke University, Durham, NC (US); UTI Limited Partnership, Calgary (CA)

( * ) Notice: Subject to any disclaimer, the term of this patent is extended or adjusted under 35 U.S.C. 154(b) by 500 days.

(21) Appl. No.: 15/514,303

(22) PCT Filed: Sep. 25, 2015

(86) PCT No.: PCT/US2015/052309
§ 371 (c)(1),
(2) Date: Mar. 24, 2017

(87) PCT Pub. No.: WO2016/049500
PCT Pub. Date: Mar. 31, 2016

(65) Prior Publication Data
US 2017/0260191 A1   Sep. 14, 2017

Related U.S. Application Data

(60) Provisional application No. 62/055,340, filed on Sep. 25, 2014, provisional application No. 62/055,354, filed on Sep. 25, 2014.

(51) Int. Cl.
*A61K 31/519* (2006.01)
*A61K 31/5377* (2006.01)
*C07D 487/04* (2006.01)

(52) U.S. Cl.
CPC .......... *C07D 487/04* (2013.01); *A61K 31/519* (2013.01); *A61K 31/5377* (2013.01)

(58) Field of Classification Search
CPC . C07D 487/04; A61K 31/5377; A61K 31/519
See application file for complete search history.

(56) References Cited

U.S. PATENT DOCUMENTS 4,663,326 A  5/1987 Hamilton
5,294,612 A  3/1994 Bacon et al.
(Continued)

FOREIGN PATENT DOCUMENTS

WO   WO 1996/028429 A1   9/1996
WO   WO 1997/033890 A1   9/1997
(Continued)

OTHER PUBLICATIONS

Martinez-Glez, DAPK1 promoter hypermethylaiton in brain metastases and peripheral blood, Neoplasma, 2007, 54(2), pp. 123-126. (Year: 2007).*

(Continued)

*Primary Examiner* — Savitha M Rao
*Assistant Examiner* — Andrew P Lee
(74) *Attorney, Agent, or Firm* — Michael Best & Friedrich LLP

(57) ABSTRACT

The present disclosure is directed to compounds that may selectively inhibit Death Associated Protein Kinases (DAPKs) as well as PIM kinases. The compounds can be used in methods of treating various disorders, including cancers.

11 Claims, 48 Drawing Sheets

(56) References Cited

U.S. PATENT DOCUMENTS

| | | |
|---|---|---|
| 2009/0163545 A1 | 6/2009 | Goldfarb |
| 2011/0281832 A1 | 11/2011 | Li et al. |
| 2013/0137708 A1 | 5/2013 | Garske et al. |

FOREIGN PATENT DOCUMENTS

| | | |
|---|---|---|
| WO | WO 2008/094575 A2 | 8/2008 |
| WO | WO 2008/094602 A2 | 8/2008 |
| WO | WO 2010/039538 A2 | 4/2010 |
| WO | WO 2012/166891 A2 | 12/2012 |
| WO | WO 2013/096820 A1 | 6/2013 |

OTHER PUBLICATIONS

Danziger, Automated site-directed drug design: a general algorithm for knowledge acquisition about hydrogen-bonding regions at protein surfaces, Proc. R. Soc. Lond., 1989, 236, pp. 101-113. (Year: 1989).*

Simone, Oncology (Introduction), Textbook of Medicine, 1997, 154, pp. 1004-1010. (Year: 1997).*

Anderson et al., "Synthesis of certain 3-alkoxy-1-β-D-ribofuranosylpyrazolo[3,4-d]pyrimidines structurally related to adenosine, inosine and guanosine," Journal of Heterocyclic Chemistry, 1986, 23(6), 1869-78.

Anderson et al., "Synthesis of certain pyrazolo[3,4-d]pyrimidin-3-one nucleosides," Journal of Heterocyclic Chemistry, 1990, 27(2), pp. 439-453.

Anderson et al., "Synthesis of pyrazolo[3,4-d]pyrimidine ribonucleoside 3',5'-cyclic phosphates related to cAMP, cIMP and cGMP," Nucleosides & Nucleotides, 1987, 6(5), 853-63.

Avasthi et al., "Design and synthesis of pyrazolo[3,4-d]pyrimidine core based dissymmetrical 'Leonard linker' compounds: 1H NMR and crystallographic evidence for folded conformation due to arene interactions," Journal of Molecular Structure, 2006, vol. 785, Issue 1-3, pp. 106-113.

Bain et al., "The selectivity of protein kinase inhibitors: a further update," Biochem. J., 2007, 408:297-315.

Bektemirov et al., "Antiviral activity of substituted 6-methylmercaptopyrazolo(3,4-d)pyrimidines and their ribosides," Acta Virologica (English Edition), 1981, 25(5), 326-9.

Bentya et al., "Electrophilic heterocyclization of 6-alken(yn)ylsulfanyl-pyrazolo[3,4-d]pyrimidin-4(5 H)-ones," Russian Journal of Organic Chemistry, 2008, vol. 44, Issue 9, pp. 1362-1368.

Berge et al, "Pharmaceutical Salts." J. Pharm. Sci., 1977, vol. 66, pp. 1-19.

Betlakowska et al., "Reaction of 4-benzylidene-2-methyl-5-oxazolone with amines, Part 2: Influence of substituents in para-position in the phenyl ring and a substituent on amine nitrogen atom on the reaction kinetics," Int. J. Chem. Kinet., 2002, 34(3):148-155.

Bialik et al., "The death-associated protein kinases: Structure, function, and beyond," Annual Review of Biochemistry, 2006, vol. 75, pp. 189-210.

Borman et al., "Smooth muscle myosin phosphatase-associated kinase induces Ca2+ sensitization via myosin phosphatase inhibition," J. Biol. Chem., 2002, 277(26):23441-23446.

Brognard et al., "Cancer-associated loss-of-function mutations implicate DAPK3 as a tumor-suppressing kinase," Cancer Res., 2011, 71(8):3152-3161.

Bulychev et al., "Synthesis of derivatives of pyrazolo[3,4-d]pyrimidin-3-ylacetic acid and their nucleosides," Khimiya Geterotsiklicheskikh Soedinenii, 1981, (4), 536-45.

Butler et al., "Role of serine-threonine phosphoprotein phosphatases in smooth muscle contractility," Am. J. Physiol.-Cell Physiol., 2013, 304(6):C485-0504.

Carlson et al., "Fluorescence Linked Enzyme Chemoproteomic Strategy for Discovery of a Potent and Selective DAPK1 and ZIPK Inhibitor," ACS Chemical Biology, 2013, 8, 2715-2723.

Carruthers, Some Modern Methods of Organic Synthesis, 3rd Edition, Cambridge University Press, Cambridge, 1987.

Chico et al., "Targeting protein kinases in central nervous system disorders," Nature Reviews Drug Discovery, 2009, 8(11):892-909.

Cohen, "Protein kinases—the major drug targets of the twenty-first century?" Nature Reviews Drug Discovery, 2002, 1(4):309-315.

Dar et al., "The evolution of protein kinase inhibitors from antagonists to agonists of cellular signaling," Annual Review of Biochemistry, 2011, vol. 80, pp. 769-795.

Deo et al., "Studies in nucleosides. Part XXII. Synthesis of 4-amino/hydroxy-1-(cyclohexyl/2'-tetrahydropyranyl)-6-amino/n-propoxy-1H-pyrazolo[3,4-d]pyrimidines and their antiallergic activity," Indian Journal of Chemistry, Section B: Organic Chemistry Including Medicinal Chemistry, 1989, 28B(3), 237-41.

El-Kerdawy et al., "Fused pyrimidine synthesis and antiinflammatory testing of certain novel imidazo[1,2-c]quinazoline, pyrazolo[3,4-d]triazolo[3,4-b]pyrimidine, and pyrimido[2,1-a]phthalazine derivatives," Saudi Pharmaceutical Journal, 1997, 5(1), 46-51.

Fadden et al., "Application of Chemoproteomics to Drug Discovery: Identification of a Clinical Candidate Targeting Hsp90," Chem. Biol., 2010, 17(7):686-694.

Feinstein et al., "Assignment of DAPI and DAPK-genes that positively mediate programmed celldeath triggered by inf-gamma-to chromosome regions 5p12.2 and 9q34.I, respectively," Genomics, 1995, 29(1):305-307.

Garin et al., "N-Halosuccinimide-sulfuric acid: an efficient reagent for the synthesis of fused benzothiazoles," Heterocycles, 1987, 26(9), 2371-9.

Gong et al., "Arachidonic-acid and diacylglycerol release associated with inhibition of myosin light-chain dephosphorylation in rabbit smooth-muscle," Journal of Physiology—London, 1995, 486(1):113-122.

Gozuacik et al., "DAPk protein family and cancer," Autophagy, 2006, 2(2):74-79.

Grassie et al., "Cross-talk between Rho-associated kinase and cyclic nucleotide-dependent kinase signaling pathways in the regulation of smooth muscle myosin light chain phosphatase," J Biol Chem, 2012, 287(43):36356-69.

Guccione et al., "Synthesis and NK-2 Antagonist Effect of 1,6-Diphenyl-Pyrazolo [3,4-d]-Thiazolo[3,2-a]4H-Pyrimidin-4-One[1]," Bioorganic & Medical Chemistry Letters, 1996, vol. 6, No. 1, pp. 59-64.

Hasan et al., "Studies on nucleosides. Part XX Synthesis and antileishmanial activity of 4,6-substituted pyrazolo[3,4-d]pyrimidine nucleosides," Indian Journal of Chemistry, Section B: Organic Chemistry Including Medicinal Chemistry, 1989, 28B(5), 403-9.

Haystead et al., "Gamma-phosphate-linked atp-sepharose for the affinity purification of protein-kinases—rapid purification to homogeneity of skeletal-muscle mitogen-activated protein-kinase kinase," Eur. J. Biochem., 1993, 214(2):459-467.

Haystead, "The purinome, a complex mix of drug and toxicity targets," Curr Top Med Chem, 2006, 6(11):1117-1127.

Haystead, "ZIP kinase, a key regulator of myosin protein phosphatase 1," Cell. Signal., 2005, 17(11):1313-1322.

Horiuti, "Mechanism of contracture on cooling of caffeine-treated frog skeletal-muscle fibers," Journal of Physiology—London, 1988, 398:131-148.

Huber et al., "7,8-dichloro-1-oxo-beta-carbolines as a versatile scaffold for the development of potent and selective kinase inhibitors with unusual binding modes," J. Med. Chem., 2012, 55(1):403-413.

Kamal El-Dean et al., "Synthesis of Some New Pyrazolotriazines, Pyrazolothiazines and Pyrazolopyrimidines ," 1997, J. Chem. Res. (S.), Issue 10, 352-353.

Kang et al., "Death-associated protein kinase-mediated cell death modulated by interaction with DANGER," J. Neurosci., 2010, 30(1):93-98.

Katakami et al., "Role of pim-1 in smooth muscle cell proliferation," J. Biol. Chem., 2004, 279(52):54742- 54749.

(56) References Cited

OTHER PUBLICATIONS

Kesley et al., "QSAR Modeling of Nucleosides Against Amastigotes of Leishmania donovani Using Logistic Regression and Classification Tree," QSAR & Combinatorial Science, 2008, 27(8), 1020-1027.
Kishino et al., "Deletion of the kinase domain in death-associated protein kinase attenuates tubular cell apoptosis in renal ischemia-reperfusion injury," J. Am. Soc. Nephrol., 2004, 15(7):1826-1834.
Kitazawa et al., "G-protein-mediated inhibition of myosin light-chain phosphatase in vascular smooth-muscle," Proc. Natl. Acad. Sci. U.S.A., 1991, 88(20):9307-9310.
Kitazawa et al., "Receptor-coupled permeabilized smooth-muscle—role of the phosphatidylinositol cascade, g-proteins, and modulation of the contractile response to $Ca^{2+}$," J. Biol. Chem., 1989, 264(10):5339-5342.
Kobayashi et al., "$Ca^{2+}$ channel blockers distinguish between gprotein-coupled pharmacomechanical $Ca^{2+}$ release and $Ca^{2+}$ sensitization," American Journal of Physiology, 1991, 260(2):C364-C370.
Korbukh et al., "Synthesis and reactions of 4- and 4,6-substituted pyrazolo[3,4-d]pyrimidine nucleosides," Bioorganicheskaya Khimiya, 1980, 6(11), 1632-8.
Korbukh et al., "The nucleosides of substituted pyrazolo(3,4-d)pyrimidines," Nucleic Acids Symposium Series, 1981, 9, 73-5.
Lack et al., "Correction to Targeting the Binding Function 3 (BF3) Site of the Human Androgen Receptor through Virtual Screening," J. Med. Chem., 2012, 55 (1), pp. 565-565.
Lack et al., "Targeting the Binding Function 3 (BF3) Site of the Human Androgen Receptor through Virtual Screening," Journal of Medicinal Chemistry, 2011, 54, 8563-8573.
Larock, Comprehensive Organic Transformations, VCH Publishers, Inc., New York, 1989.
Ihara et al., "The regulation of smooth muscle contractility by zipper-interacting protein kinase," Canadian Journal of Physiology and Pharmacology, 2007, 85(1):79-87.
Lontay et al., "Smoothelin-like 1 protein regulates myosin phosphatase-targeting subunit 1 expression during sexual development and pregnancy," J. Biol. Chem., 2010, 285(38):29357-29366.
Lu et al., "The study on synthesis and biological activity of pyrazolopyrimidine derivatives," Jiangxi Shifan Daxue Xuebao, Ziran Kexueban, 2011, 35(1), 10-14.
MacDonald et al., "Identification of the endogenous smooth muscle myosin phosphatase-associated kinase," Proceedings of the National Academy of Sciences, 2001, 98(5):2419-2424.
Magnuson et al., "Why target PIM1 for cancer diagnosis and treatment?," Future Oncol., 2010, 6(9):1461-1478.
Manetti et al., "Identification of a novel pyrazolo 3,4-d pyrimidine able to inhibit cell proliferation of a human osteogenic sarcoma in vitro and in a xenograft model in mice," J. Med. Chem., 2007, 50(23):5579-5588.
Manning et al., "The protein kinase complement of the human genome," Science, 2002, 298(5600):1912-1934.
Misra et al., "Studies on Nucleosides: Part XXVIII1. Synthesis of 4-Amino (or Hydroxy)-6-Methylthio-1-(3'-Deoxy-β-D-ribofuranosyl)-1-H-pyrazolo[3, 4-d]Pyrimidines," Nucleosides and Nucleotides, 1990, vol. 9, Issue 6, pp. 837-846.
Moellering et al., "How chemoproteomics can enable drug discovery and development," Chem. Biol., 2012, 19(1):11-22.
Mosselhi et al., "New Triheterocyclic Ring System. Synthesis of Functionalized Pyrazolo[3,4-d]Pyrimido[1,2-b][1,2,4,5]Tetrazine Derivatives," Journal of the Chinese Chemical Society, 2006, vol. 53, Issue 4, pp. 923-929.
Mukaida et al., "Roles of Pim-3, a novel survival kinase, in tumorigenesis," Cancer Science, 2011, 102(8):1437-1442.
Mukhopadhyay et al., "DAPK-ZIPK-L13a axis constitutes a negative-feedback module regulating inflammatory gene expression," Mol. Cell, 2008, 32(3):371-382.
Nichols et al., "Discovery of Wild-Type and Y181C Mutant Non-nucleoside HIV-1 Reverse Transcriptase Inhibitors Using Virtual Screening with Multiple Protein Structures," J. Chem. Inf. Model., 2009, 49 (5), pp. 1272-1279.

Okamoto et al., "Structure-activity relationship of novel DAPK inhibitors identified by structure-based virtual screening," Bioorg. Med. Chem., 2010, 18(7):2728-2734.
Paulin et al., "Signal transducers and activators of transcription-3/PIM1 axis plays a critical role in the pathogenesis of human pulmonary arterial hypertension," Circulation, 2011, 123(11):1205-1215.
Periodic Table of the Elements, CAS version, Handbook of Chemistry and Physics, 75th Ed., 1994.
Petrie et al., "Synthesis and biological activity of 6-azacadeguomycin and certain 3,4,6-trisubstituted pyrazolo[3,4-d]pyrimidine ribonucleosides," Journal of Medicinal Chemistry, 1985, 28(8), 1010-16.
Poste et al., "Lipid Vesicles as Carriers for Introducing Biologically Active Materials inot Cells,", Methods in Cell Biology, vol. XIV, Academic Press, New York, N. Y., (1976), pp. 33-71.
Radi et al., "Identification of potent c-Src inhibitors strongly affecting the proliferation of human neuroblastoma cells," Bioorg. Med. Chem. Lett., 2011, 21(19):5928-5933.
Russo et al., "Pyrazolothiazolopyrimidine derivatives as a novel class of antiinflammatory or antinociceptive agents—synthesis, structural characterization and pharmacological evaluation," Eur. J. Med. Chem., 1993, 28(5):363-376.
Schenone et al., "Synthesis of 1-(2-chloro-2-phenylethyl)-6-methylthio-1H-pyrazolo 3,4-d pyrimidines 4-amino substituted and their biological evaluation," Eur. J. Med. Chem., 2004, 39(2):153-160.
Shamloo et al., "Death-associated protein kinase is activated by dephosphorylation in response to cerebral ischemia," J. Biol. Chem., 2005, 280(51):42290-42299.
Shen et al., "Blueprint for antimicrobial hit discovery targeting metabolic networks," PNAS, 2010, 107(3):1082-1087.
Shoval et al., "ZIPK: A unique case of murine-specific divergence of a conserved vertebrate gene," Plos Genetics, 2007, 3(10):1884-1893.
Smith and March, March 's Advanced Organic Chemistry, 5th Edition, John Wiley & Sons, Inc., New York, 2001.
Somlyo et al., "Signal-transduction and regulation in smooth-muscle," Nature, 1994, 372(6503):231-236.
Sorrell, Organic Chemistry, University Science Books, Sausalito, 1999.
Tominaga et al., "Synthesis of pyrazolo[3,4-d]pyrimidine derivatives using ketene dithioacetals," Journal of Heterocyclic Chemistry, 1990, 27(3), pp. 775-783.
Ulke-Lemee et al., "Opportunities to target specific contractile abnormalities with smooth muscle protein kinase inhibitors," Pharmaceuticals, 2010, 3(6):1739-1760.
Vas'kevich et al., "Cyclofunctionalization of 6-alkenylsulfanylpyrazolo[3,4-d]-pyrimidin-4(5 H)-ones with arenesulfenyl chlorides," Russian Journal of Organic Chemistry, 2009, vol. 45, Issue 12, pp. 1847-1852.
Velentza et al., "A protein kinase associated with apoptosis and tumor suppression—Structure, activity, and discovery of peptide substrates," J. Biol. Chem., 2001, 276(42):38956-38965.
Velentza et al., "An aminopyridazine-based inhibitor of a pro-apoptotic protein kinase attenuates hypoxia-ischemia induced acute brain injury," Bioorg. Med. Chem. Lett., 2003, 13(20):3465-3470.
Velentza et al., "Structure, activity, regulation, and inhibitor discovery for a protein kinase associated with apoptosis and neuronal death," Pharmacol. Ther., 2002, 93(2-3):217-224.
Watterson et al., "The role of sphingosine-1-phosphate in smooth muscle contraction," Cell. Signal., 2005, 17(3):289-298.
Weitzel et al., "Phosphorylation-dependent control of ZIPK nuclear import is species specific," Cell. Signal, 2011, 23(1):297-303.
Wesche et al., "High throughput screening for protein kinase inhibitors," Combinatorial Chemistry & High Throughput Screening, 2005, 8(2):181-195.
Wuts and Greene, Protective Groups in Organic Synthesis, 3rd Edition; John Wiley and Sons, 1999.
Zhang et al., "A Simple Statistical Parameter for Use in Evaluation and Validation of High Throughput Screening Assays," J Biomol Screen, 1999, 4(2):67-73.

(56) References Cited

OTHER PUBLICATIONS

Wang et al., "Synthesis and herbicidal activity of 3,6-bis(alkylthio)-1-phenyl-pyrazolo[3,4-d]pyrimidin-4-ones," Youji Huaxue, 2010, 30(11), 1749-1753.
International Search Report and Written Opinion for Application No. PCT/US2015/052309 dated Dec. 28, 2015 (10 pages).
Carlson et al., "Targeting Pim Kinases and DAPK3 to Control Hypertension," Cell Chemical Biology, Oct. 2018, 25:1195-1207.
Garcia et al., Pan-PIM Kinase Inhibition Provides a Novel Therapy for Treating Hematologic Cancers, Clin Cancer Res, Apr. 2014, 20(7):1834-1845.
Goulopoulou, "Maternal Vascular Physiology in Preeclampsia," Hypertension, Dec. 2017, 70:1066-1073.
Liu et al., "Nur77 Suppresses Pulmonary Artery Smooth Muscle Cell Proliferation through Inhibition of the STAT3/Pim-1/NFAT Pathway," Am J Respir Cell Mol Biol, Feb. 2014, 50(2):379-388.
Luszczak et al., "PIM kinase inhibition: co-targeted therapeutic approaches in prostate cancer," Signal Transduction and Targeted Therapy, Jan. 2020, 5:7, 10 pages.
Lyle et al., "Regulation of Pulmonary Vascular Smooth Muscle Contractility in Pulmonary Arterial Hypertension: Implications for Therapy," Front. Physiol, Aug. 2017, 8:614, 11 pages.
Melchiorre et al., "Cardiovascular Implications in Preeclampsia. An Overview," Circulation, Aug. 2014, 130:703-714.
Pfefferle et al., "Transcriptomic classification of genetically engineered mouse models of breast cancer identifies human subtype counterparts," Genome Biology, Nov. 2013, 14:R125, 16 pages.
Renard et al., "Pim-1: A new biomarker in pulmonary arterial hypertension," Pulmonary Circulation, Jan.-Mar. 2013, 3(1):74-81.
Vangrieken et al., "The direct and sustained consequences of severe placental hypoxia on vascular contractility," PLoS One, Aug. 2018, 13(8):e0202648, 15 pages.
VanWijk et al., "Resistance artery smooth muscle function in pregnancy and preeclampsia," Am J Obstet Gynecol, 2002,186:148-54.
Zhang et al., "PIM Kinase as an Executional Target in Cancer," Journal of Cancer Prevention, Sep. 2018, 23(3):109-116.

\* cited by examiner

| HS # | R1 | R2 | ZIPK EC$_{50}$ (µM) | PIM1 EC$_{50}$ (µM) | PIM3 EC$_{50}$ (µM) | | HS # | R1 | R2 | ZIPK EC$_{50}$ (µM) | PIM1 EC$_{50}$ (µM) | PIM3 EC$_{50}$ (µM) |
|---|---|---|---|---|---|---|---|---|---|---|---|---|
| HS-38 | | | 34.1 | 81.9 | 4.9 | | HS-57 | | | >300 | >300 | >300 |
| HS-43 | | | >300 | >300 | 8.8 | | HS-58 | | | >300 | >300 | 58.9 |
| HS-50 | | | >300 | 28.6 | 46.3 | | HS-60 | | | >300 | >300 | >300 |
| HS-51 | | | >300 | >300 | 39.1 | | HS-61 | | | >300 | >300 | 13.2 |
| HS-52 | | | >300 | >300 | >300 | | HS-62 | | | >300 | >300 | 39.0 |
| HS-53 | | | >300 | >300 | 8.4 | | HS-63 | | | 34.3 | 10.0 | 9.8 |
| HS-54 | | | >300 | >300 | >300 | | HS-64 | | | >300 | >300 | 8.1 |
| HS-55 | | | >300 | >300 | >300 | | HS-73 | | | >300 | >300 | >300 |
| HS-56 | | | 43.9 | 6.7 | 7.4 | | HS-74 | | | >300 | 19.3 | 23.7 |

FIG. 23

| HS # | R1 | R2 | ZIPK EC$_{50}$ (μM) | PIM1 EC$_{50}$ (μM) | PIM3 EC$_{50}$ (μM) |
|---|---|---|---|---|---|
| HS-75 | | | >300 | 17.4 | 17.7 |
| HS-76 | | | 44.4 | 30.0 | 8.7 |
| HS-82 | | | >300 | | 22.1 |
| HS-83 | | | 76.4 | 48.4 | 56.6 |
| HS-84 | | | >300 | 83.9 | 56.7 |
| HS-85 | | | 101.7 | 32.9 | 22.3 |
| HS-86 | | | >300 | 83.6 | 80.4 |
| HS-87 | | | 42.3 | 66.7 | 119.0 |
| HS-88 | | | 103.5 | | 25.1 |
| HS-89 | | | 66.3 | | 29.7 |
| HS-90 | | | >300 | | >300 |
| HS-91 | | | >300 | | 133.7 |
| HS-92 | | | 42.4 | 63.0 | 44.7 |
| HS-93 | | | 127.1 | | 23.8 |
| HS-94 | | | 30.0 | | 18.1 |
| HS-95 | | | 132.1 | | 43.4 |

FIG. 23 (cont'd)

KINASE INHIBITORS AND RELATED METHODS OF USE

CROSS-REFERENCE TO RELATED APPLICATIONS

This application is a national stage filing under 35 U.S.C. 371 of International Application No. PCT/US2015/052309, filed Sep. 25, 2015, which application claims the benefit of U.S. Application Ser. No. 62/055,340, filed Sep. 25, 2014, and U.S. Application Ser. No. 62/055,354, filed Sep. 25, 2014, the entire contents of which are hereby incorporated by reference in their entirety.

TECHNICAL FIELD

The present disclosure is directed to compounds that may selectively inhibit Death Associated Protein Kinases (DAPKs) as well as PIM kinases (PIMKs), pharmaceutical compositions comprising such compounds, and methods of using such compounds in the treatment of disorders.

BACKGROUND

The Death Associated Protein Kinase (DAPK) family of three closely related serine/threonine kinases; DAPK1, DAPK2 (also called DRP-1) and Zipper-interacting protein kinase or ZIPK (also called DAPK3). In vivo they mediate cell death through transmission of apoptotic and autophagic signals and highly regulate both non-muscle and smooth muscle (SM) myosin phosphorylation. DAPK1 and ZIPK are attractive drug targets for the attenuation of ischemia-reperfusion induced tissue injury and for smooth muscle related disorders.

The PIM (provirus integrating site for Moloney murine leukemia virus) kinases play significant roles in tumorigenesis by preventing apoptosis and by promoting proliferation and survival of normal and cancerous cells. PIM3 phosphorylates a set of substrates that regulate apoptosis, cellular division, and metabolism. PIM1 kinase plays a critical role in SM cell proliferation and in the pathogenesis of pulmonary artery hypertension. Because the PIM kinases are constitutively active and aberrantly expressed in numerous types of cancer, they may be attractive targets for cancer therapy.

SUMMARY

In one aspect, disclosed herein is a method of treating cancer in a subject in need of treatment, comprising administering to the subject a therapeutically effective amount of a compound of formula (I):

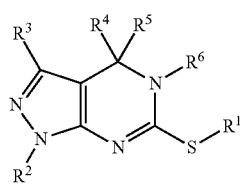

(I)

wherein:
$R^1$ is selected from the group consisting of $C_1$-$C_6$ alkyl, $C_2$-$C_6$ alkenyl, heterocyclyl, and —$(CR^aR^b)_n$—X;

$R^2$ is selected from the group consisting of $C_1$-$C_6$ alkyl, optionally substituted aryl and optionally substituted heteroaryl;

$R^3$ is selected from the group consisting of hydrogen and optionally substituted $C_1$-$C_6$ alkyl;

$R^4$ is hydrogen and $R^5$ optionally substituted $C_1$-$C_6$ alkoxy, or $R^4$ and $R^5$ together form an oxo group;

$R^6$ is selected from the group consisting of hydrogen and —$(CR^aR^b)_n$—X;

each $R^a$ and $R^b$ is independently selected from the group consisting of hydrogen and $C_1$-$C_4$ alkyl;

n is 1, 2, 3, 4, 5 or 6;

each X is independently selected from the group consisting of optionally substituted aryl, optionally substituted heteroaryl, —$OR^c$, —$COR^d$, —$COOR^e$, —$CON(R^f)(R^g)$, —CN;

each $R^c$ is independently selected from the group consisting of hydrogen, $C_1$-$C_4$ alkyl, and —$(CH_2)_m$—Y wherein m is 1, 2 or 3 and Y is selected from the group consisting of —OH, —O($C_1$-$C_4$-alkyl), —$COOR^e$ and —$CON(R^f)(R^g)$;

each $R^d$ is independently selected from the group consisting of optionally substituted aryl and optionally substituted heteroaryl; and each $R^e$, $R^f$ and $R^g$ is independently selected from the group consisting of hydrogen and $C_1$-$C_4$ alkyl.

In another aspect, disclosed herein is a method of treating cancer in a subject in need of treatment, comprising administering to the subject a therapeutically effective amount of a compound of formula (II):

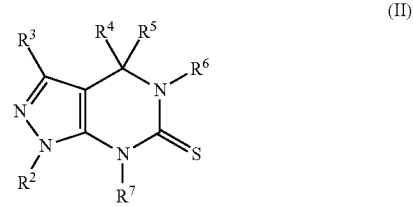

(II)

wherein:
$R^2$ is selected from the group consisting of $C_1$-$C_6$ alkyl, optionally substituted aryl and optionally substituted heteroaryl;

$R^3$ is selected from the group consisting of hydrogen and optionally substituted $C_1$-$C_6$ alkyl;

$R^4$ is hydrogen and $R^5$ optionally substituted $C_1$-$C_6$ alkoxy, or $R^4$ and $R^5$ together form an oxo group;

$R^6$ is selected from the group consisting of hydrogen and —$(CR^aR^b)_n$—X;

$R^7$ is selected from the group consisting of hydrogen and —$(CR^aR^b)_n$—X;

each $R^a$ and $R^b$ is independently selected from the group consisting of hydrogen and $C_1$-$C_4$ alkyl;

n is 1, 2, 3, 4, 5 or 6;

each X is independently selected from the group consisting of optionally substituted aryl, optionally substituted heteroaryl, —$OR^c$, —$COR^d$, —$COOR^e$, —$CON(R^f)(R^g)$, —CN;

each $R^c$ is independently selected from the group consisting of hydrogen, $C_1$-$C_4$ alkyl, and —$(CH_2)_m$—Y wherein m is 1, 2 or 3 and Y is selected from the group consisting of —OH, —O($C_1$-$C_4$-alkyl), —$COOR^e$ and —$CON(R^f)(R^g)$;

each $R^d$ is independently selected from the group consisting of optionally substituted aryl and optionally substituted heteroaryl; and each $R^e$, $R^f$ and $R^g$ is independently selected from the group consisting of hydrogen and $C_1$-$C_4$ alkyl.
In another aspect, disclosed herein is a pharmaceutical composition comprising a pharmaceutically acceptable carrier, and a compound selected from the group consisting of
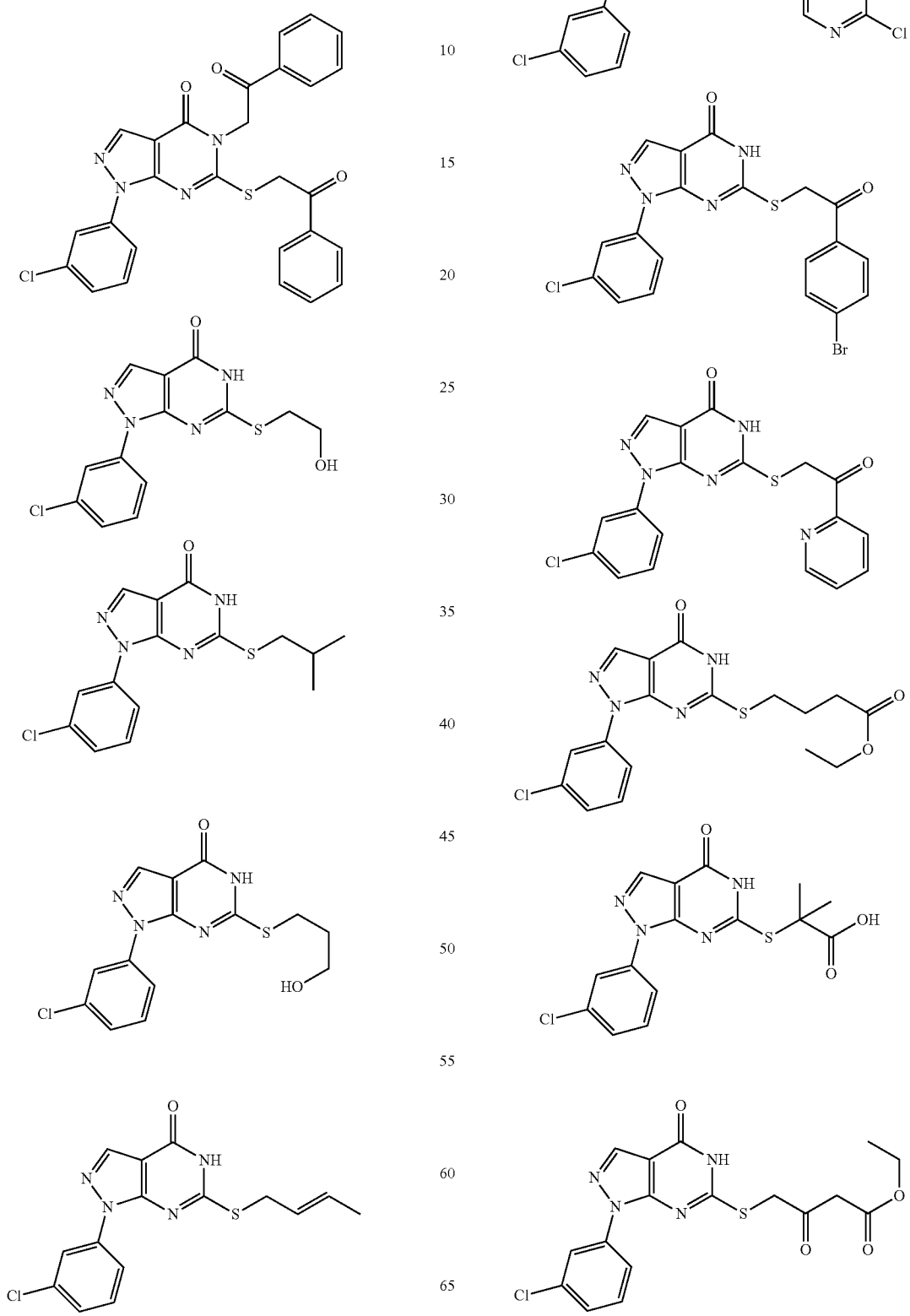

-continued
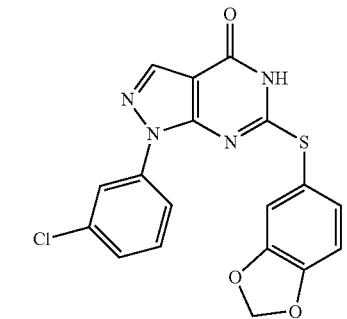
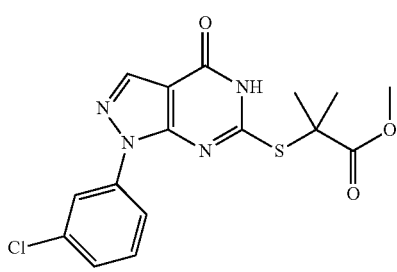
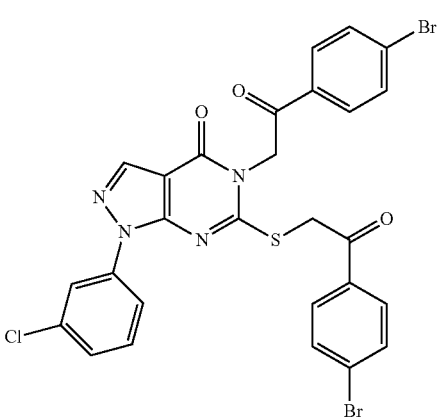
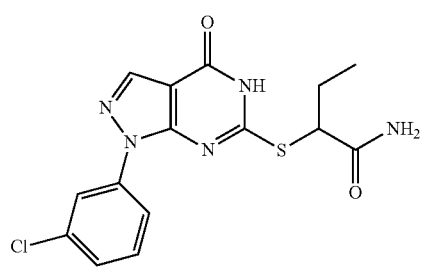
-continued
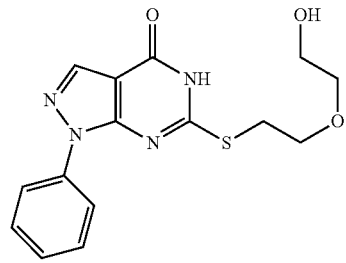
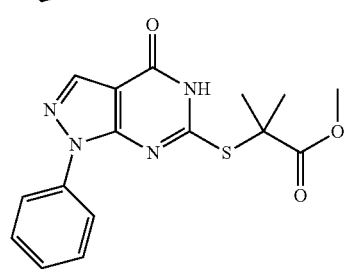
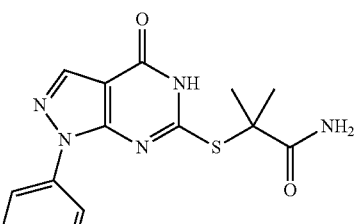
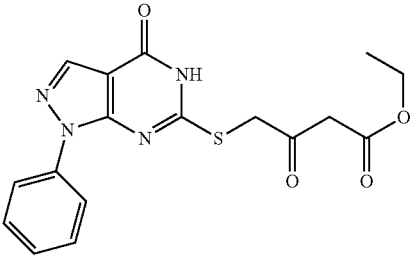
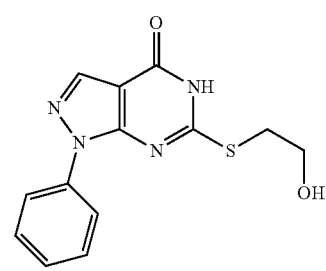
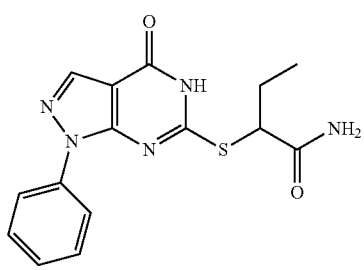

-continued
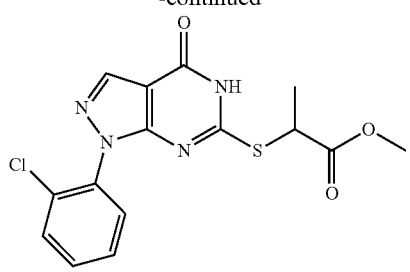
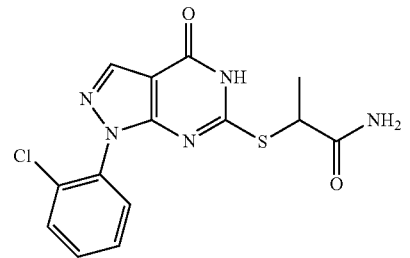
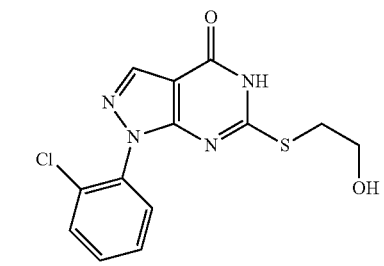
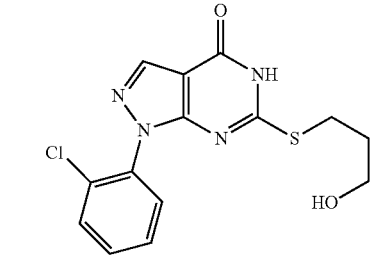
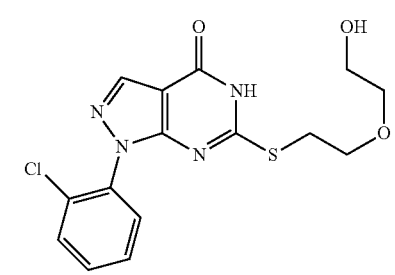
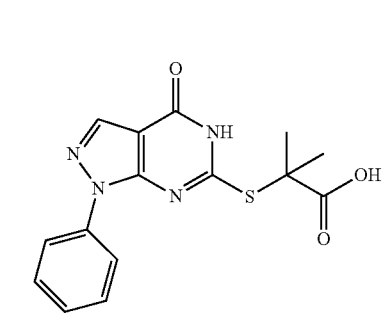
-continued
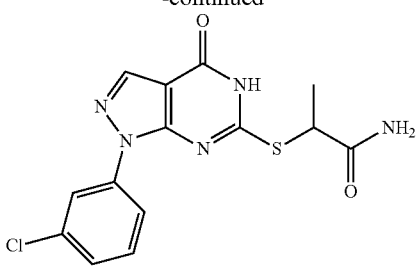
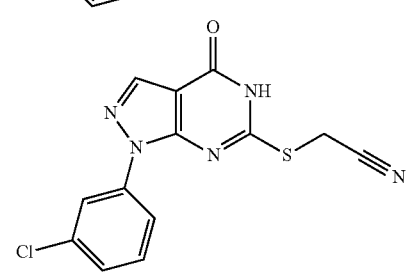
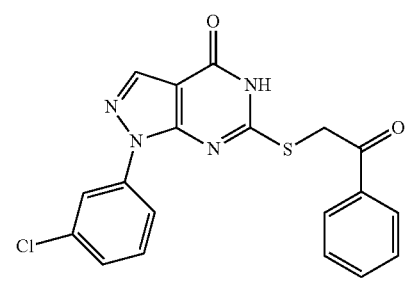
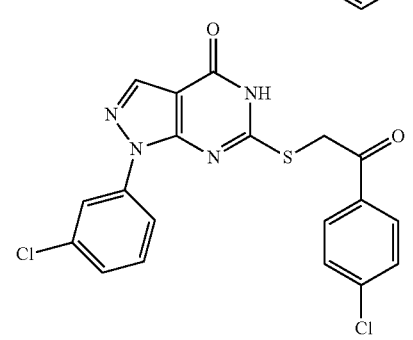
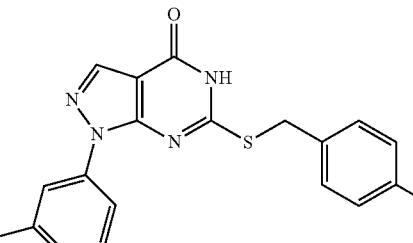
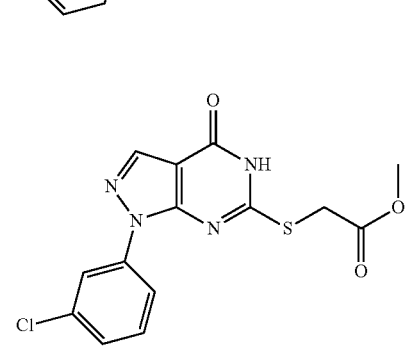

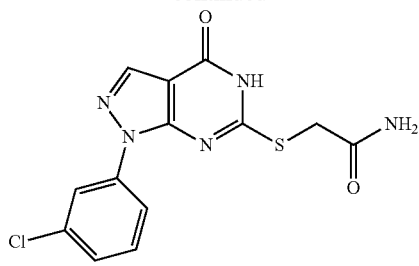
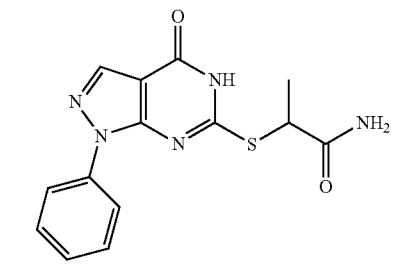
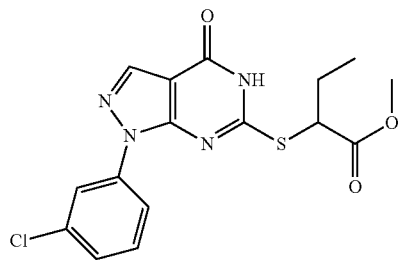
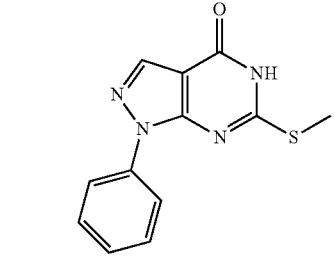
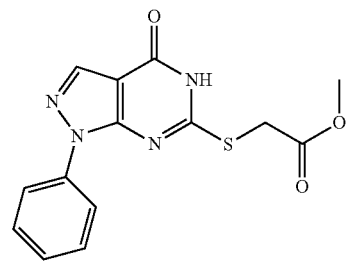
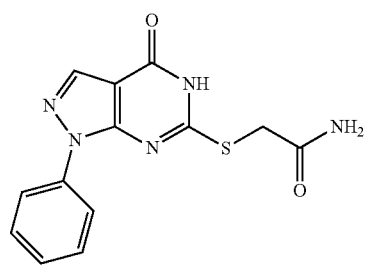
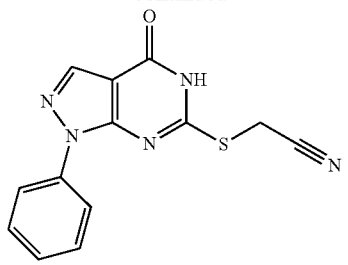
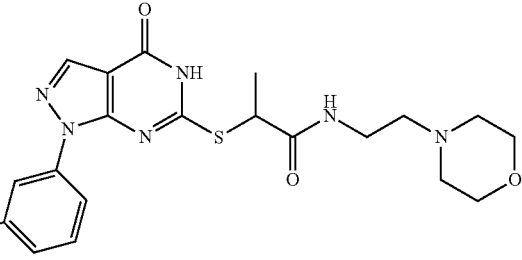
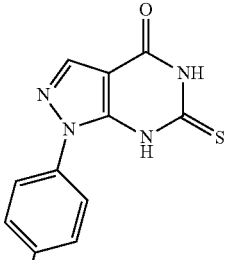
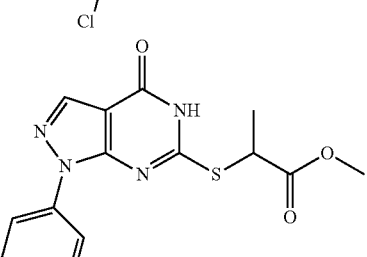
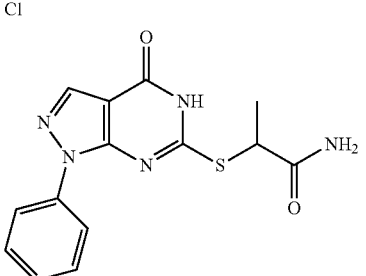
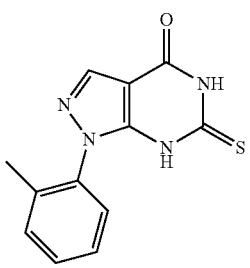

-continued
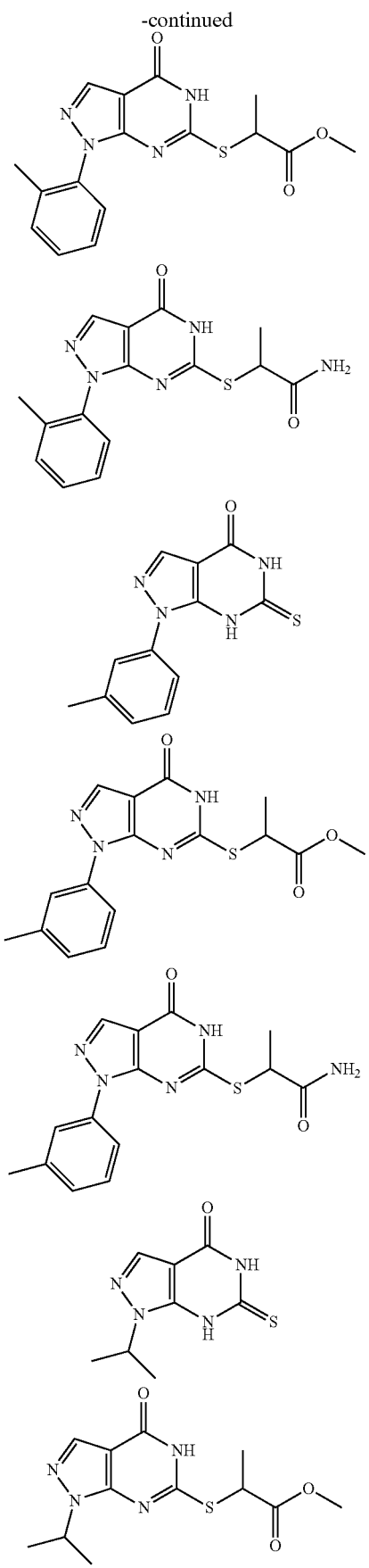
-continued
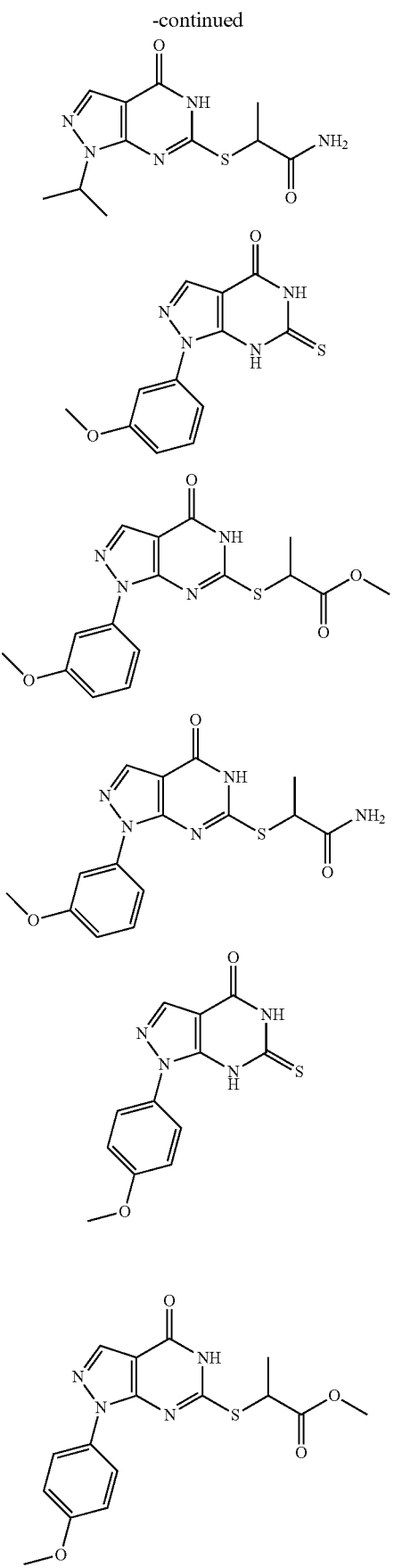

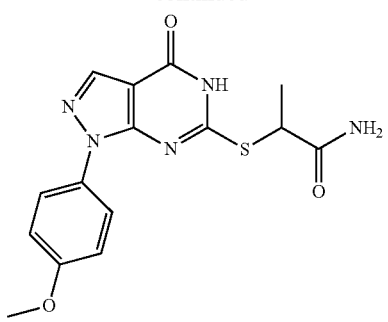
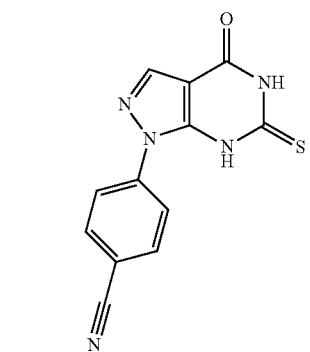
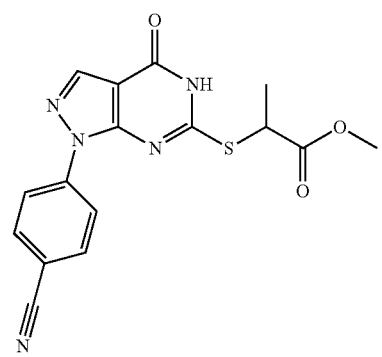
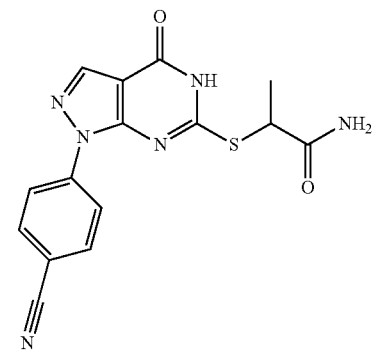
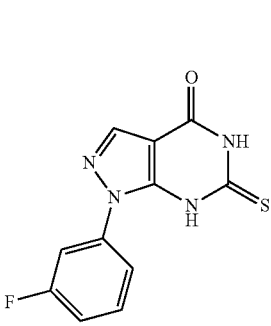
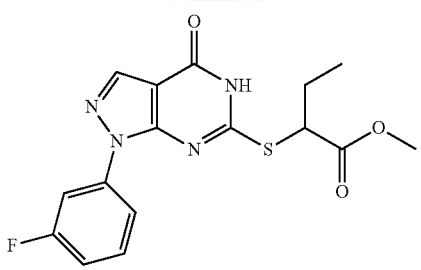
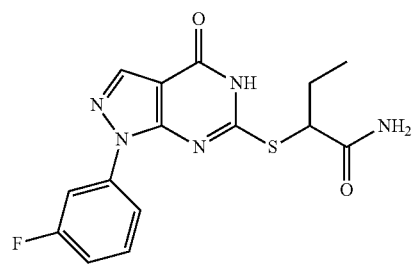
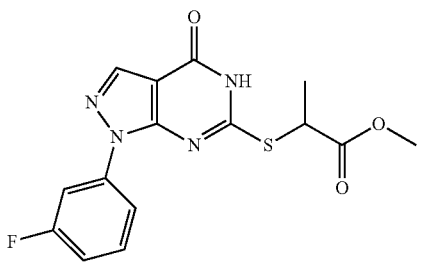
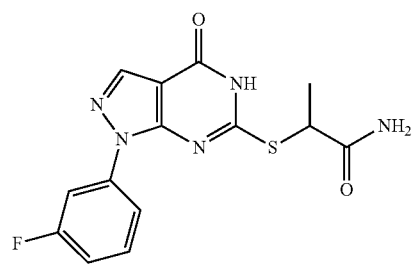
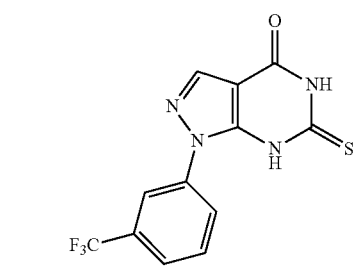
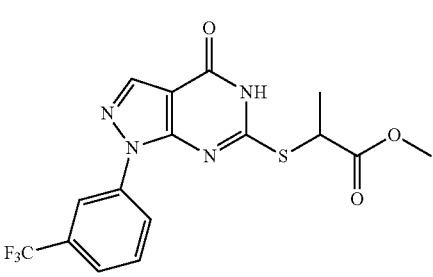

-continued
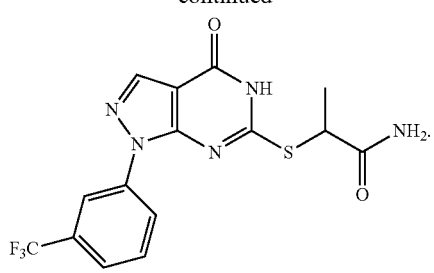
In another aspect, disclosed herein is a compound selected from the group consisting of:
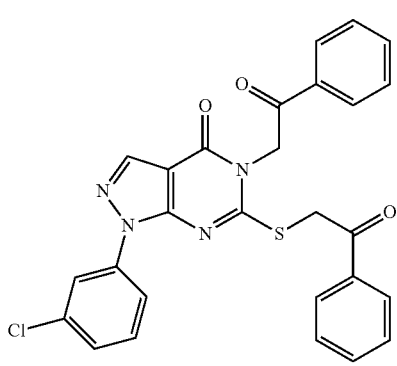
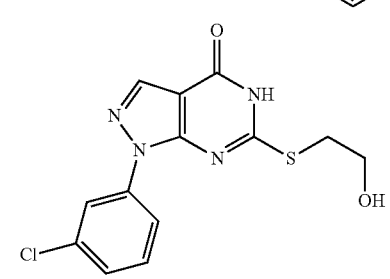
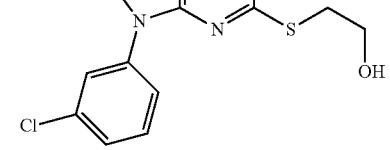
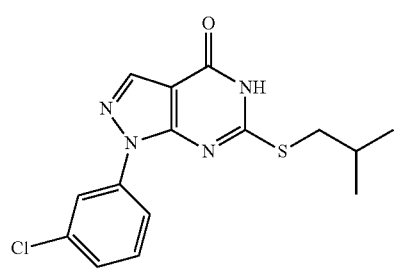
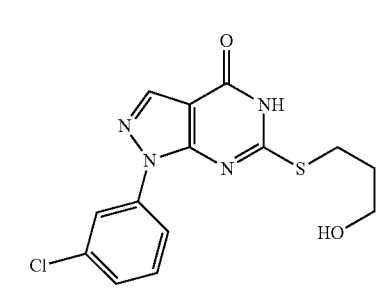
-continued
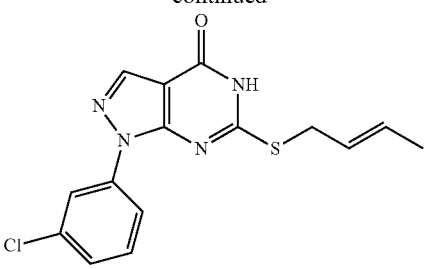
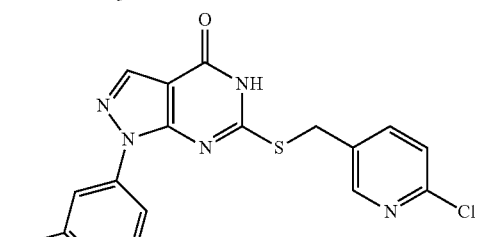
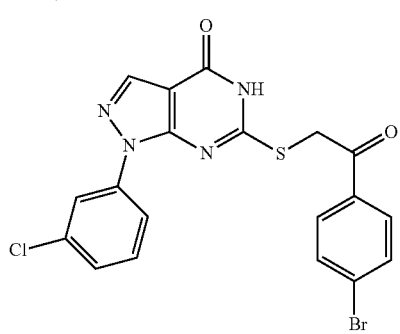
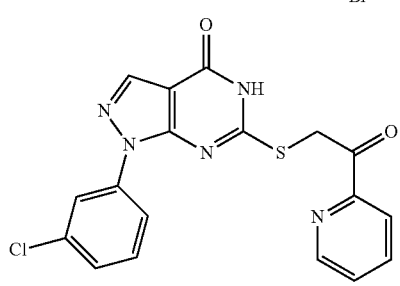
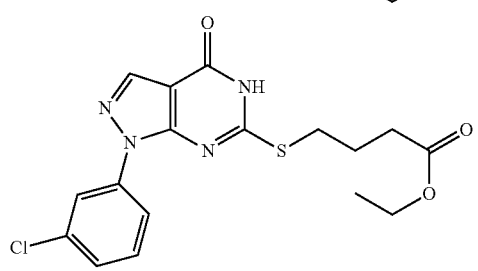
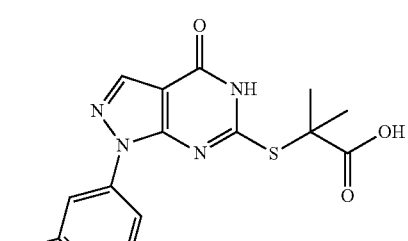

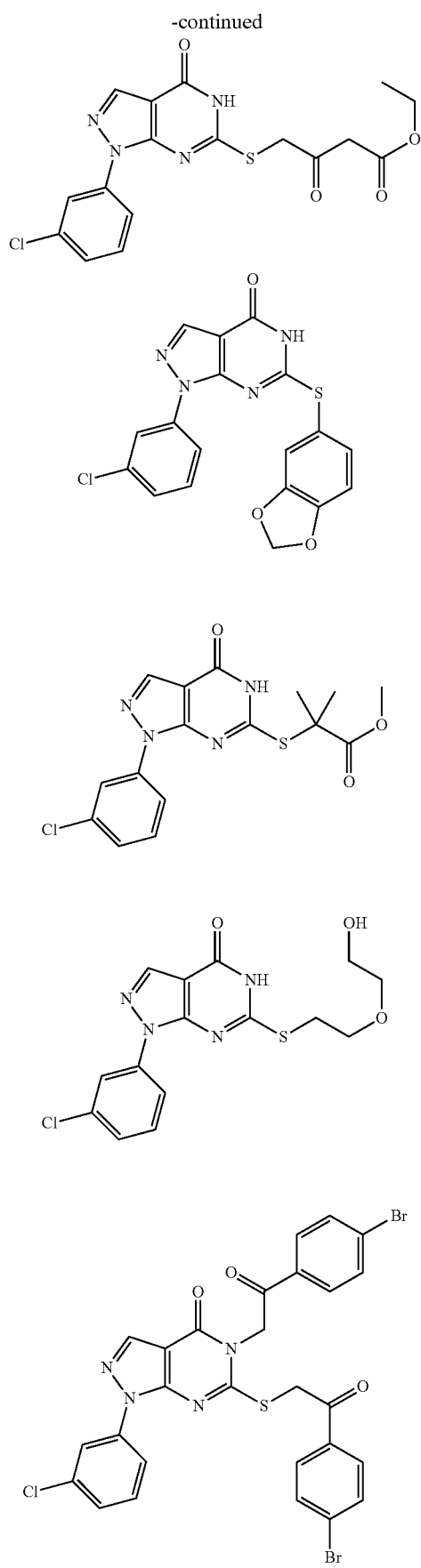

-continued
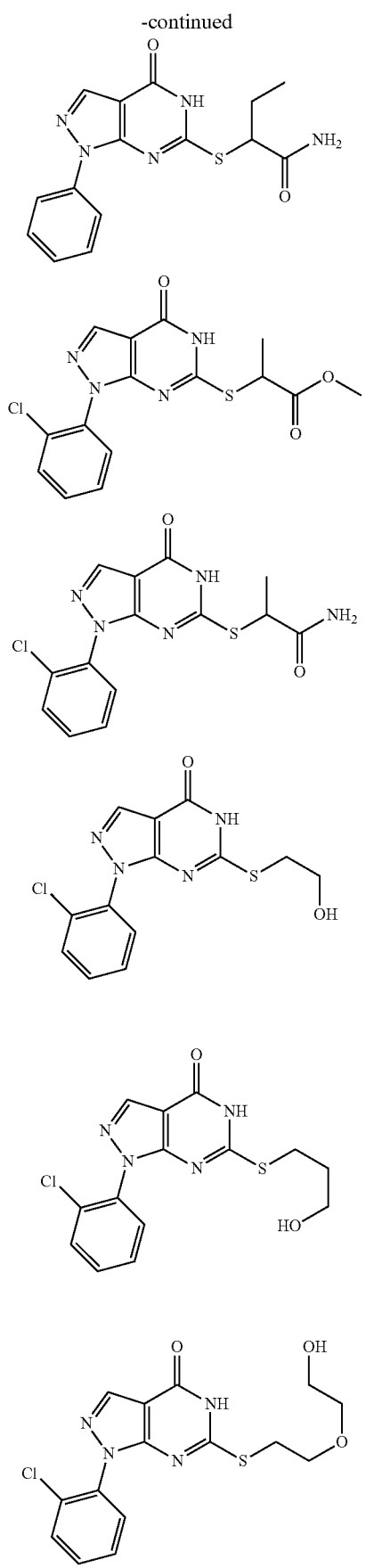
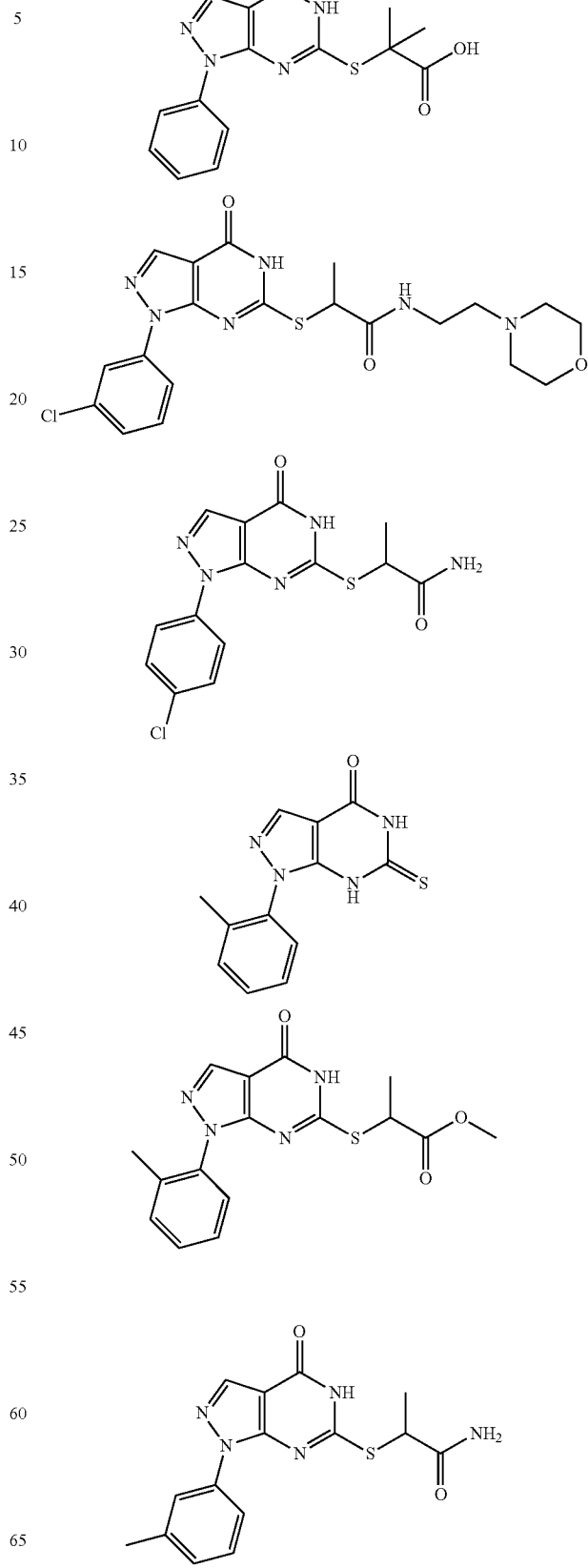

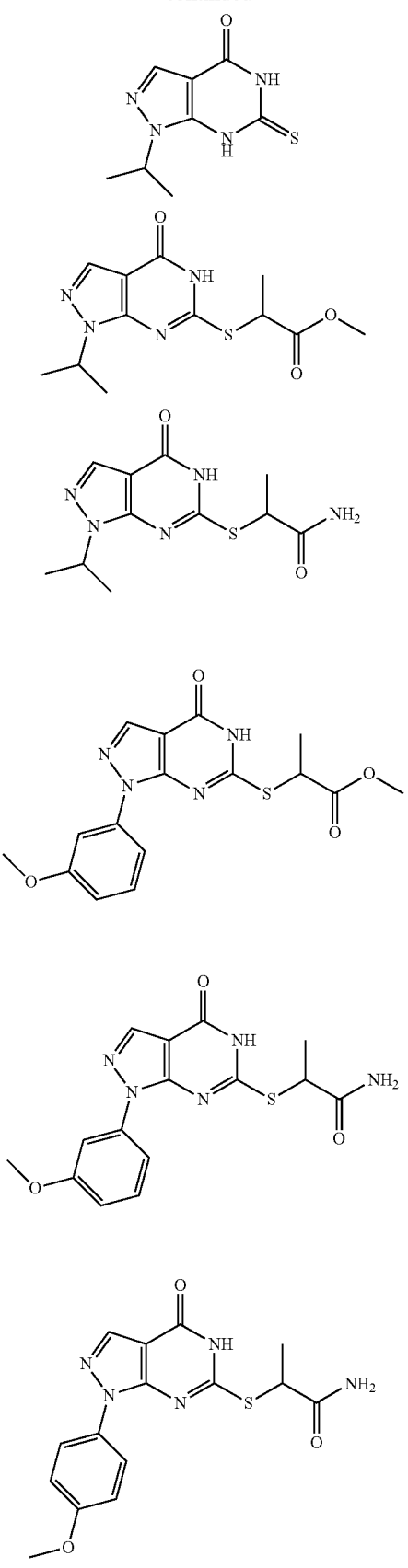
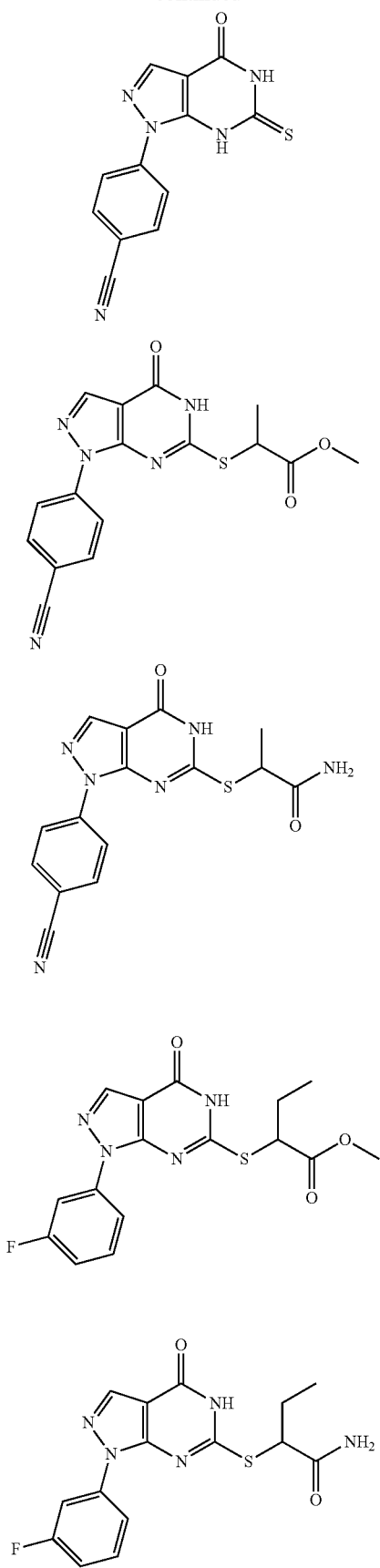

-continued

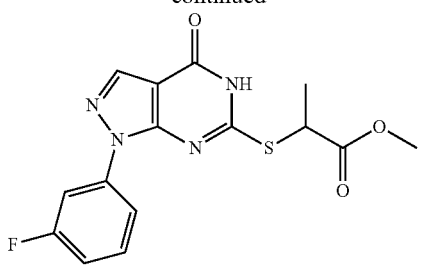

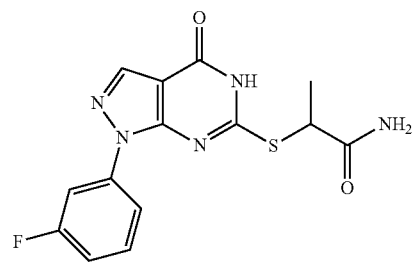

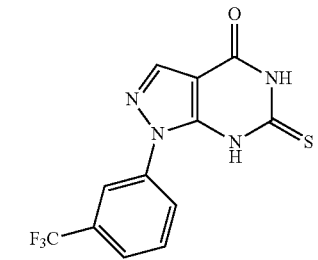

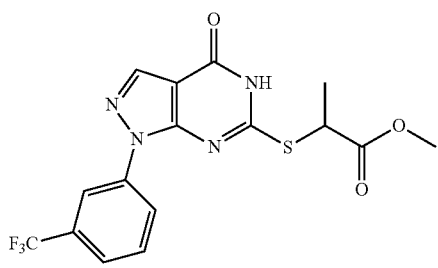

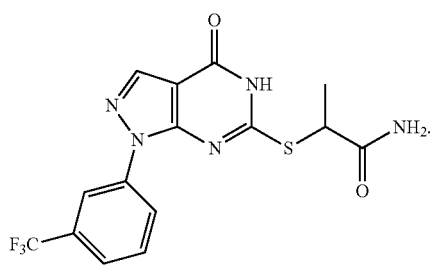

In one aspect, disclosed herein is a method of treating a disorder in a subject in need of treatment, wherein the disorder is selected from the group consisting of hypertension, pulmonary hypertension, stroke, an ischemia reperfusion injury, erectile dysfunction, premature labor, pre-eclampsia, migraine, asthma, diarrhea, irritable bowel syndrome and peripheral artery disease, comprising administering to the subject a therapeutically effective amount of a compound of formula (I):

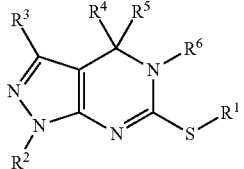

(I)

$R^1$ is selected from the group consisting of $C_1$-$C_6$ alkyl, $C_2$-$C_6$ alkenyl, heterocyclyl, and —$(CR^aR^b)_n$—X.

$R^2$ is selected from the group consisting of optionally substituted aryl and optionally substituted heteroaryl;

$R^3$ is selected from the group consisting of hydrogen and optionally substituted $C_1$-$C_6$ alkyl;

$R^4$ is hydrogen and $R^5$ optionally substituted $C_1$-$C_6$ alkoxy, or $R^4$ and $R^5$ together form an oxo group;

$R^6$ is selected from the group consisting of hydrogen and —$(CR^aR^b)_n$—X;

each $R^a$ and $R^b$ is independently selected from the group consisting of hydrogen and $C_1$-$C_4$ alkyl;

n is 1, 2, 3, 4, 5 or 6;

each X is independently selected from the group consisting of optionally substituted aryl, optionally substituted heteroaryl, —$OR^c$, —$COR^d$, —$COOR^e$, —$CON(R^f)(R^g)$, —CN;

each $R^c$ is independently selected from the group consisting of hydrogen, $C_1$-$C_4$ alkyl, and —$(CH_2)_m$—Y wherein m is 1, 2 or 3 and Y is selected from the group consisting of —OH, —$O(C_1$-$C_4$-alkyl), —$COOR^e$ and —$CON(R^f)(R^g)$;

each $R^d$ is independently selected from the group consisting of optionally substituted aryl and optionally substituted heteroaryl; and each $R^e$, $R^f$ and $R^g$ is independently selected from the group consisting of hydrogen and $C_1$-$C_4$ alkyl.

In one aspect, disclosed herein is a method of treating a disorder in a subject in need of treatment, wherein the disorder is selected from the group consisting of hypertension, pulmonary hypertension, stroke, an ischemia reperfusion injury, erectile dysfunction, premature labor, pre-eclampsia, migraine, asthma, diarrhea, irritable bowel syndrome and peripheral artery disease, comprising administering to the subject a therapeutically effective amount of a compound of formula (II):

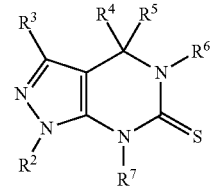

(II)

wherein:

$R^2$ is selected from the group consisting of $C_1$-$C_6$ alkyl, optionally substituted aryl and optionally substituted heteroaryl;

$R^3$ is selected from the group consisting of hydrogen and optionally substituted $C_1$-$C_6$ alkyl;

$R^4$ is hydrogen and $R^5$ optionally substituted $C_1$-$C_6$ alkoxy, or $R^4$ and $R^5$ together form an oxo group;

$R^6$ is selected from the group consisting of hydrogen and —$(CR^aR^b)_n$—X;

R[7] is selected from the group consisting of hydrogen and —(CR$^a$R$^b$)$_n$—X;

each R$^a$ and R$^b$ is independently selected from the group consisting of hydrogen and C$_1$-C$_4$ alkyl;

n is 1, 2, 3, 4, 5 or 6;

each X is independently selected from the group consisting of optionally substituted aryl, optionally substituted heteroaryl, —OR$^c$, —COR$^d$, —COOR$^e$, —CON(R$^f$)(R$^g$), —CN;

each R$^c$ is independently selected from the group consisting of hydrogen, C$_1$-C$_4$ alkyl, and —(CH$_2$)$_m$—Y wherein m is 1, 2 or 3 and Y is selected from the group consisting of —OH, —O(C$_1$-C$_4$-alkyl), —COOR$^e$ and —CON(R$^f$)(R$^g$);

each R$^d$ is independently selected from the group consisting of optionally substituted aryl and optionally substituted heteroaryl; and each R$^e$, R$^f$ and R$^g$ is independently selected from the group consisting of hydrogen and C$_1$-C$_4$ alkyl.

Other aspects and embodiments of the disclosure will become apparent in light of the following description.

BRIEF DESCRIPTION OF THE DRAWINGS

FIG. 23 is a table showing $EC_{50}$ values for certain compounds against ZIPK, PIM1 and PIM3.

DETAILED DESCRIPTION

Figure 1:
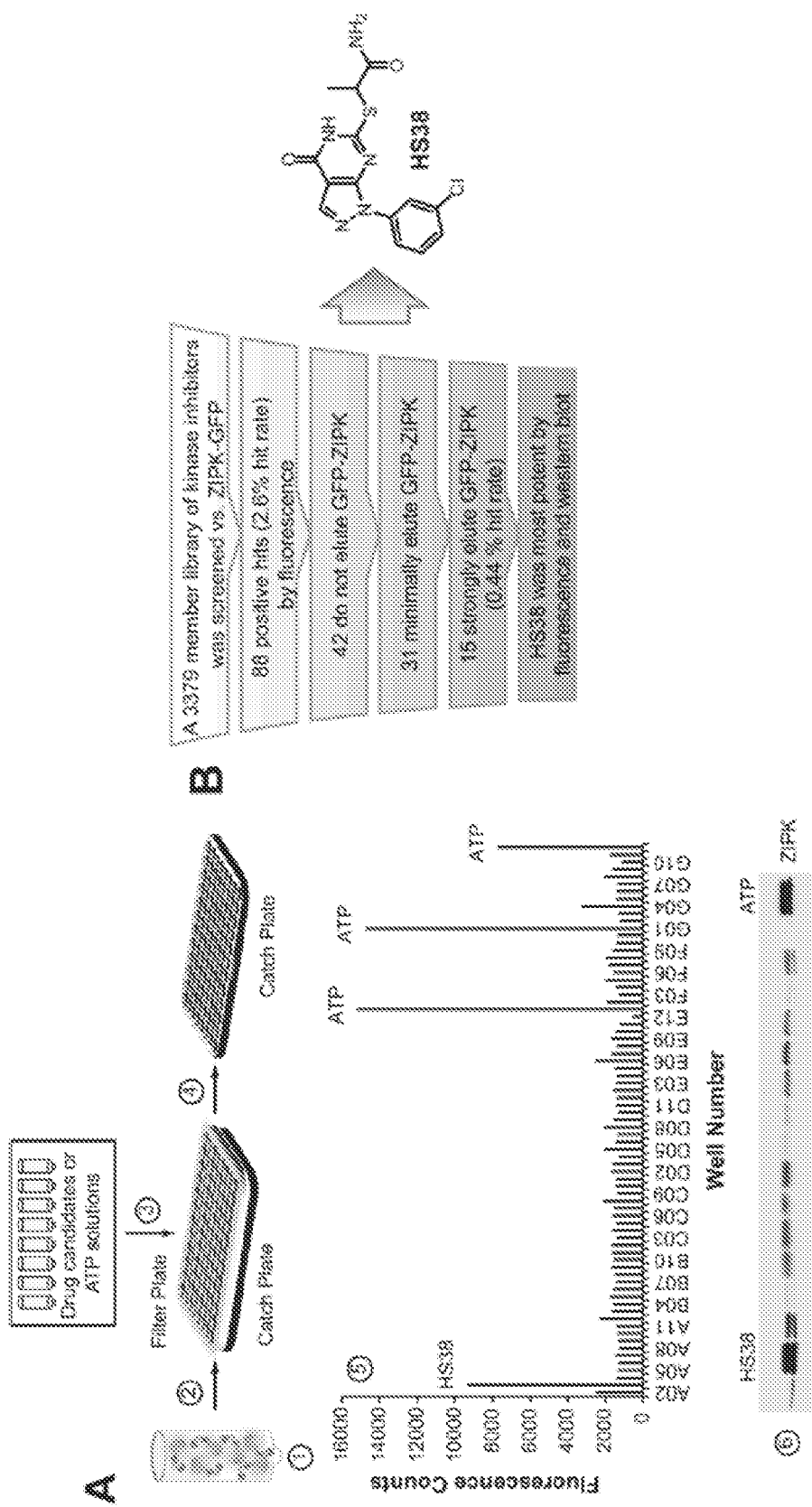
FIG. 1 is a schematic representing a fluorescence linked enzyme chemoproteomic strategy (FLECS). (A) (1) γ-Linked ATP sepharose beads were mixed with crude mammalian cell lysate containing GFP-ZIPK. (2) Charged beads were distributed into 96-well filter plates. (3) Drug candidates or ATP solutions were added to each well. (4) Eluates were separated into a filter plate by centrifugation. (5) The fluorescence of each eluate was determined and a fluorescence histogram generated. All wells containing >5000 fluorescence counts (2.5×background) were considered to contain potential hits. Soluble ATP was used as a positive control. (6) Eluate from each hit-containing well was western blotted for GFP-ZIPK and hits were refined based on band intensity. (B) Summary of screen results and structure of HS38.

Disclosed herein are methods selectively inhibiting Death Associated Protein Kinases (DAPKs) as well as PIM kinases (PIMKs), using pyrazolo[3,4-d]pyrimidinone compounds and related derivatives. The compounds that selectively inhibit these kinases may be useful in treating a variety of disorders including cancer, cardiovascular disorders, and ischemia-reperfusion injuries.

Before any embodiments of the disclosure are detailed, it is to be understood that the present disclosure is not limited in its application to the details of construction and the arrangement of components set forth in the following description or illustrated in the following drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

1. Definitions

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis,* 3$^{rd}$ Edition, Cambridge University Press, Cambridge, 1987; the entire contents of each of which are incorporated herein by reference.

The term "acyl" refers to an alkylcarbonyl, cycloalkylcarbonyl, heterocyclylcarbonyl, arylcarbonyl or heteroarylcarbonyl substituent, any of which may be further substituted (e.g., with one or more substituents).

The term "alkyl" refers to a saturated aliphatic hydrocarbon chain, which may be straight or branched. An alkyl group may have an indicated number of carbon atoms. For example, $C_1$-$C_{12}$ alkyl refers to an alkyl group having from 1 to 12 (inclusive) carbon atoms. $C_1$-$C_4$ alkyl refers to an alkyl group having 1, 2, 3 or 4 carbon atoms, such as methyl, ethyl, n-propyl, isopropyl, n-butyl, sec-butyl or tert-butyl. An alkyl group may be optionally substituted, e.g., with one or more substituents.

The term "alkylene" refers to a divalent alkyl, e.g., —$CH_2$—, —$CH_2CH_2$—, —$CH_2CH_2CH_2$— or —$CH_2CH(CH_3)CH_2$—. An alkylene may be optionally substituted, e.g., with one or more substituents.

The term "alkenyl" refers to a straight or branched hydrocarbon chain having one or more double bonds. Examples of alkenyl groups include, but are not limited to, allyl, propenyl, 2-butenyl, 3-hexenyl and 3-octenyl groups. One of the double bond carbons may optionally be the point of attachment of the alkenyl substituent. The term "alkenylene" refers to a divalent alkenyl, e.g., —CH=CH—, —CH=$CH_2CH_2$— or —CH=C=CH—. An alkenyl or alkenylene may be optionally substituted, e.g., with one or more substituents.

The term "alkynyl" refers to a straight or branched hydrocarbon chain having one or more triple bonds. Examples of alkynyl groups include, but are not limited to, ethynyl, propargyl, and 3-hexynyl. One of the triple bond carbons may optionally be the point of attachment of the alkynyl substituent. The term "alkynylene" refers to a divalent alkynyl, e.g., —C≡C— or —C≡C—$CH_2$—. An alkynyl or alkynylene may be optionally substituted, e.g., with one or more substituents.

The term "amino" refers to a group of the formula —$NR^1R^2$, wherein $R^1$ and $R^2$ are each independently selected from, for example, hydrogen, alkyl, cycloalkyl, heterocyclyl, aryl and heteroaryl, or $R^1$ and $R^2$, together with the nitrogen to which they are attached, may form a ring structure. Examples of amino groups include, but are not limited to, —$NH_2$, alkylamino groups such as —$NHCH_3$, —$NHCH_2CH_3$ and —$NHCH(CH)_2$, dialkylamino groups such as —$N(CH_3)_2$ and —$N(CH_2CH_3)_2$, and arylamino groups such as —NHPh. Examples of cyclic amino groups include, but are not limited to, aziridinyl, azetidinyl, pyrrolidinyl, piperidino, piperazinyl, perhydrodiazepinyl, morpholino, and thiomorpholino. The groups $R^1$ and $R^2$ may be optionally substituted, e.g., with one or more substituents.

The term "aryl" refers to an aromatic monocyclic, bicyclic, or tricyclic hydrocarbon ring system, wherein any ring atom capable of substitution can be substituted (e.g., with one or more substituents). Examples of aryl moieties include, but are not limited to, phenyl, naphthyl, and anthracenyl.

The term "arylalkyl" refers to an alkyl moiety in which an alkyl hydrogen atom is replaced with an aryl group. Arylalkyl includes groups in which more than one hydrogen atom has been replaced with an aryl group. Examples of arylalkyl groups include benzyl, 2-phenylethyl, 3-phenylpropyl, 9-fluorenyl, benzhydryl, and trityl groups.

The term "cycloalkyl" as used herein refers to nonaromatic, saturated or partially unsaturated cyclic, bicyclic, tricyclic or polycyclic hydrocarbon groups having 3 to 12 carbons. Any ring atom can be substituted (e.g., with one or more substituents). Cycloalkyl groups can contain fused rings. Fused rings are rings that share one or more common carbon atoms. Examples of cycloalkyl groups include, but are not limited to, cyclopropyl, cyclobutyl, cyclopentyl, cyclohexyl, cyclohexenyl, cyclohexadienyl, methylcyclohexyl, adamantyl, norbornyl and norbornenyl.

The term "cycloalkylalkyl", as used herein, refers to an alkyl group substituted with a cycloalkyl group.

The term "halo" or "halogen" as used herein refers to any radical of fluorine, chlorine, bromine or iodine.

The term "haloalkyl" as used herein refers to an alkyl in which one or more hydrogen atoms are replaced with a halogen, and includes alkyl moieties in which all hydrogens have been replaced with halogens (e.g., perfluoroalkyl such as $CF_3$).

The term "heteroaryl" as used herein refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms independently selected from O, N, S, P and Si (e.g., carbon atoms and 1-3, 1-6, or 1-9 heteroatoms independently selected from O, N, S, P and Si if monocyclic, bicyclic, or tricyclic, respectively). Any ring atom can be substituted (e.g., with one or more substituents). Heteroaryl groups can contain fused rings, which are rings that share one or more common atoms. Examples of heteroaryl groups include, but are not limited to, radicals of pyridine, pyrimidine, pyrazine, pyridazine, pyrrole, imidazole, pyrazole, oxazole, isoxazole, furan, thiazole, isothiazole, thiophene, quinoline, isoquinoline, quinoxaline, quinazoline, cinnoline, indole, isoindole, indolizine, indazole, benzimidazole, phthalazine, pteridine, carbazole, carboline, phenanthridine, acridine, phenanthroline, phenazine, naphthyridines and purines.

The term "heteroarylalkyl", as used herein, refers to an alkyl group substituted with a heteroaryl group.

The term "heterocyclyl" as used herein refers to a non-aromatic, saturated or partially unsaturated 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, S, Si and P (e.g., carbon atoms and 1-3, 1-6, or 1-9 heteroatoms of O, N, S, Si and P if monocyclic, bicyclic, or tricyclic, respectively). Any ring atom can be substituted (e.g., with one or more substituents). Heterocyclyl groups can contain fused rings, which are rings that share one or more common atoms. Examples of heterocyclyl groups include, but are not limited to, radicals of tetrahydrofuran, tetrahydrothiophene, tetrahydropyran, piperidine, piperazine, morpholine, pyrroline, pyrimidine, pyrrolidine, indoline, tetrahydropyridine, dihydropyran, thianthrene, pyran, benzopyran, xanthene, phenoxathiin, phenothiazine, furazan, lactones, lactams such as azetidinones and pyrrolidinones, sultams, sultones, and the like.

The term "heterocyclylalkyl", as used herein, refers to an alkyl group substituted with a heterocyclyl group.

The term "hydroxy" refers to an —OH radical. The term "alkoxy" refers to an —O— alkyl radical. The term "aryloxy" refers to an —O-aryl radical.

The term "oxo" refers to an oxygen atom, which forms a carbonyl when attached to carbon, an N-oxide when attached to nitrogen, and a sulfoxide or sulfone when attached to sulfur.

The term "mercapto" or "thiol" refers to an —SH radical. The term "thioalkoxy" or "thioether" refers to an —S-alkyl radical. The term "thioaryloxy" refers to an —S-aryl radical.

The term "substituents" refers to a group "substituted" on an alkyl, alkenyl, alkynyl, cycloalkyl, cycloalkylalkyl, heterocyclyl, heterocyclylalkyl, aryl, arylalkyl, heteroaryl or heteroarylalkyl group at any atom of that group. Any atom can be substituted. Suitable substituents include, without limitation: acyl, acylamido, acyloxy, alkoxy, alkyl, alkenyl, alkynyl, amido, amino, carboxy, cyano, ester, halo, hydroxy, imino, nitro, oxo (e.g., C=O), phosphonate, sulfinyl, sulfonyl, sulfonate, sulfonamino, sulfonamido, thioamido, thiol, thioxo (e.g., C=S), and ureido. In embodiments, substituents on a group are independently any one single, or any combination of the aforementioned substituents. In embodiments, a substituent may itself be substituted with any one of the above substituents.

Any of the above substituents may be abbreviated herein, for example, the abbreviations Me, Et and Ph represent methyl, ethyl and phenyl, respectively. A more comprehensive list of the abbreviations used by organic chemists of ordinary skill in the art appears in the first issue of each volume of the Journal of Organic Chemistry; this list is typically presented in a table entitled Standard List of Abbreviations. The abbreviations contained in said list, and all abbreviations used by organic chemists of ordinary skill in the art, are hereby incorporated by reference.

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

Where substituent groups are specified by their conventional chemical formulae, written from left to right, they optionally encompass substituents resulting from writing the structure from right to left, e.g., —CH$_2$O— optionally also recites —OCH$_2$—.

In accordance with a convention used in the art, the group:

is used in structural formulas herein to depict the bond that is the point of attachment of the moiety or substituent to the core or backbone structure.

It specifically is understood that any numerical range recited herein includes all values from the lower value to the upper value. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this application.

2. Compounds

Compounds disclosed herein, which may be used in pharmaceutical compositions and methods described herein, include compounds of formula (I):

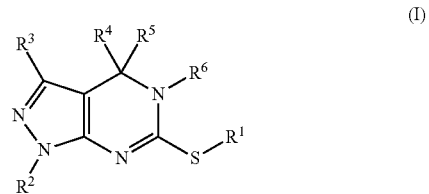

wherein:

$R^1$ is selected from the group consisting of $C_1$-$C_6$ alkyl, $C_2$-$C_6$ alkenyl, heterocyclyl, and —$(CR^aR^b)_n$—X;

$R^2$ is selected from the group consisting of $C_1$-$C_6$ alkyl, optionally substituted aryl and optionally substituted heteroaryl;

$R^3$ is selected from the group consisting of hydrogen and optionally substituted $C_1$-$C_6$ alkyl;

$R^4$ is hydrogen and $R^5$ optionally substituted $C_1$-$C_6$ alkoxy, or $R^4$ and $R^5$ together form an oxo group;

$R^6$ is selected from the group consisting of hydrogen and —$(CR^aR^b)_n$—X;

each $R^a$ and $R^b$ is independently selected from the group consisting of hydrogen and $C_1$-$C_4$ alkyl;

n is 1, 2, 3, 4, 5 or 6;

each X is independently selected from the group consisting of optionally substituted aryl, optionally substituted heteroaryl, —$OR^c$, —$COR^d$, —$COOR^e$, —$CON(R^f)(R^g)$, —CN;

each $R^c$ is independently selected from the group consisting of hydrogen, $C_1$-$C_4$ alkyl, and —$(CH_2)_m$—Y wherein m is 1, 2 or 3 and Y is selected from the group consisting of —OH, —O($C_1$-$C_4$-alkyl, —$COOR^e$ and —$CON(R^f)(R^g)$;

each $R^d$ is independently selected from the group consisting of optionally substituted aryl, optionally substituted heteroaryl and —$(CH_2)_p$—Z wherein p is 1, 2 or 3 and Z is selected from the group consisting of —OH, —$O(C_1$-$C_4$-alkyl), —$COOR^e$ and —$CON(R^f)(R^g)$; and each $R^e$, $R^f$ and $R^g$ is independently selected from the group consisting of hydrogen, $C_1$-$C_4$ alkyl and —$(CH_2)_q$—W wherein q is 1, 2 or 3 and W is selected from the group consisting of —OH, —$O(C_1$-$C_4$-alkyl), and heterocyclyl.

Compounds disclosed herein, which may be used in the pharmaceutical compositions and methods described herein, also include compounds of formula (II):

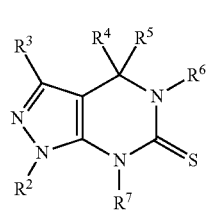

(II)

wherein:
$R^2$ is selected from the group consisting of $C_1$-$C_6$ alkyl, optionally substituted aryl and optionally substituted heteroaryl;
$R^3$ is selected from the group consisting of hydrogen and optionally substituted $C_1$-$C_6$ alkyl;
$R^4$ is hydrogen and $R^5$ optionally substituted $C_1$-$C_6$ alkoxy, or $R^4$ and $R^5$ together form an oxo group;
$R^6$ is selected from the group consisting of hydrogen and —$(CR^aR^b)_n$—X;
$R^7$ is selected from the group consisting of hydrogen and —$(CR^aR^b)_n$—X;
each $R^a$ and $R^b$ is independently selected from the group consisting of hydrogen and $C_1$-$C_4$ alkyl;
n is 1, 2, 3, 4, 5 or 6;
each X is independently selected from the group consisting of optionally substituted aryl, optionally substituted heteroaryl, —$OR^c$, —$COR^d$, —$COOR^e$, —$CON(R^f)(R^g)$, —CN;
each $R^c$ is independently selected from the group consisting of hydrogen, $C_1$-$C_4$ alkyl, and —$(CH_2)_m$—Y wherein m is 1, 2 or 3 and Y is selected from the group consisting of —OH, —$O(C_1$-$C_4$-alkyl), —$COOR^e$ and —$CON(R^f)(R^g)$;
each $R^d$ is independently selected from the group consisting of optionally substituted aryl, optionally substituted heteroaryl and —$(CH_2)_p$—Z wherein p is 1, 2 or 3 and Z is selected from the group consisting of —OH, —$O(C_1$-$C_4$-alkyl), —$COOR^e$ and —$CON(R^f)(R^g)$; and
each $R^e$, $R^f$ and $R^g$ is independently selected from the group consisting of hydrogen and $C_1$-$C_4$ alkyl.

In some embodiments, $R^2$ is unsubstituted phenyl. In some embodiments, $R^2$ is substituted phenyl. In some embodiments, $R^2$ is phenyl substituted with a halogen. In some embodiments, $R^2$ is 2-chlorophenyl, 3-chlorophenyl or 4-chlorophenyl. In some embodiments, $R^2$ is phenyl substituted with cyano. In some embodiments, $R^2$ is phenyl substituted with alkoxy. In some embodiments, $R^2$ is phenyl substituted with alkyl. In some embodiments, $R^2$ is phenyl substituted with fluoro. In some embodiments, $R^2$ is isopropyl.

In some embodiments, $R^3$ is hydrogen. In some embodiments, $R^4$ and $R^5$ together form an oxo group.

In some embodiments, $R^6$ is H. In some embodiments, $R^6$ is —$(CH_2)$—X.

In some embodiments, X is —$COR^d$. In some embodiments, $R^d$ is optionally substituted aryl.

In some embodiments, $R^7$ is H.

In some embodiments, compounds may be commercially available. In other embodiments, compounds may be synthesized using standard methods known in the art. For example, compounds may be prepared using synthetic methods described in the Examples section.

In some embodiments, compounds that may be used in compositions and methods of the disclosure may be selected from group consisting of:

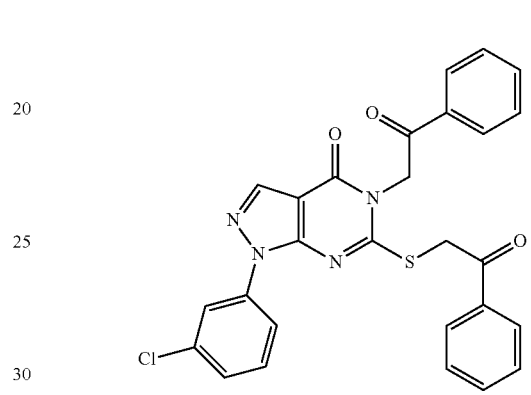

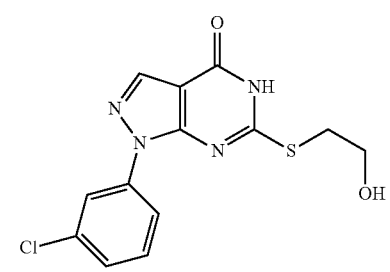

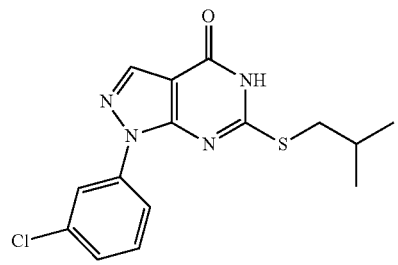

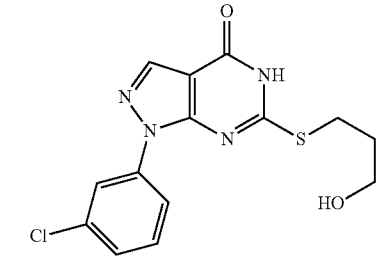

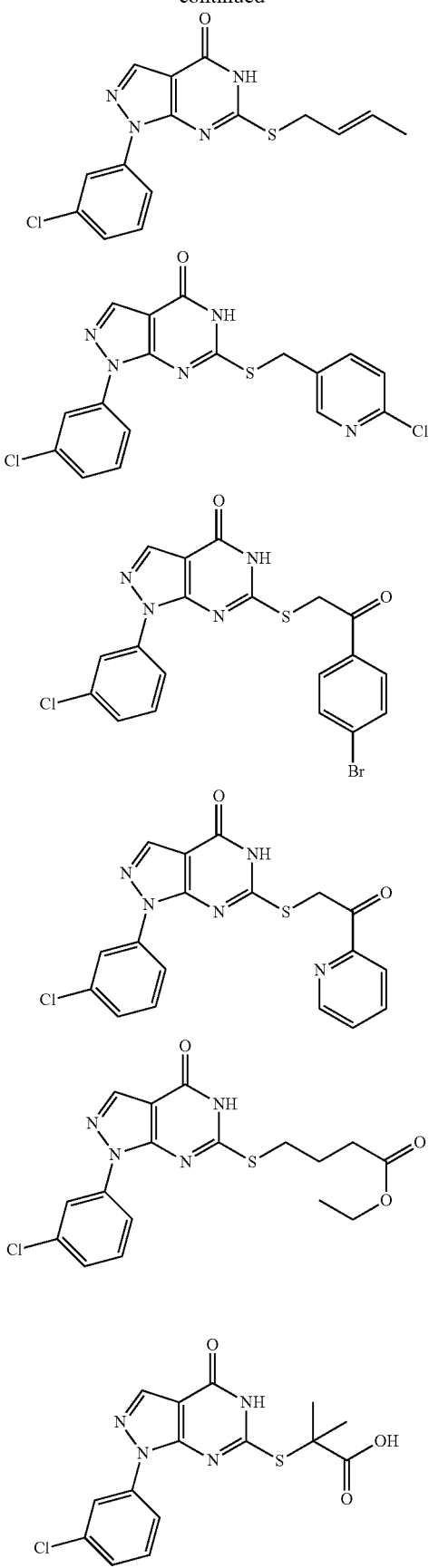
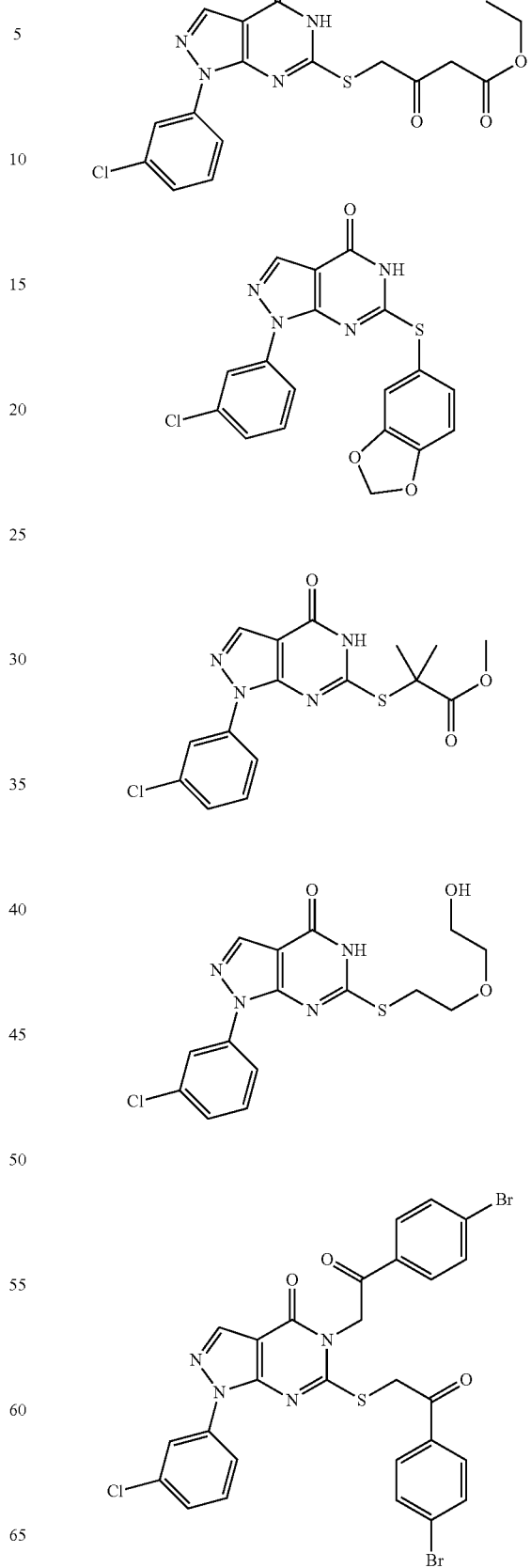

-continued
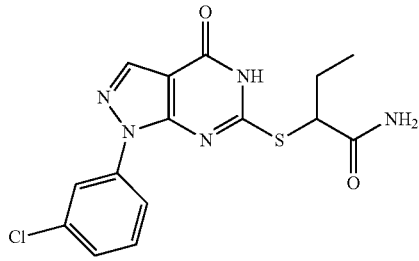
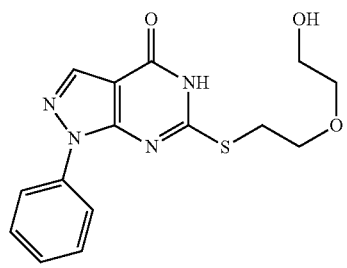
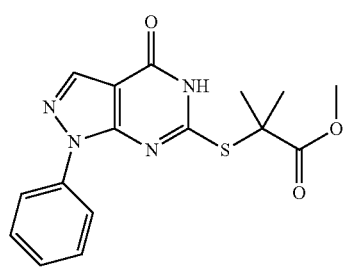
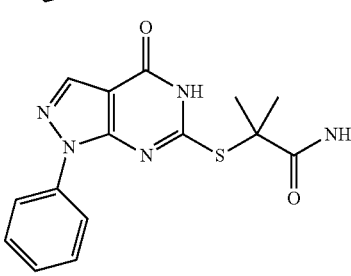
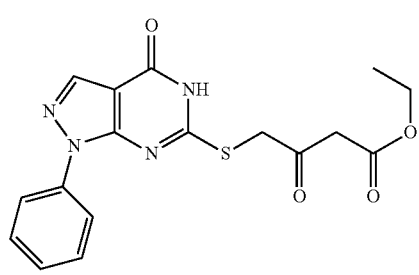
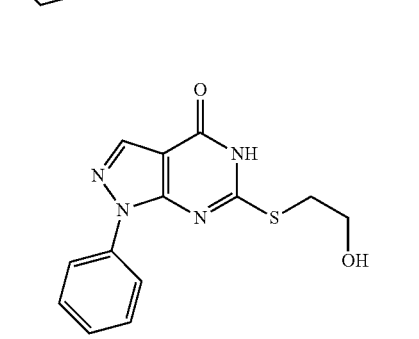
-continued
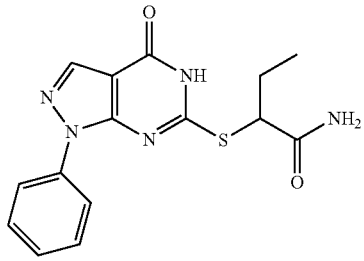
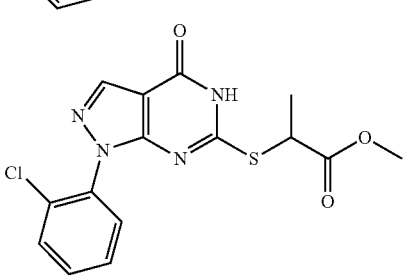
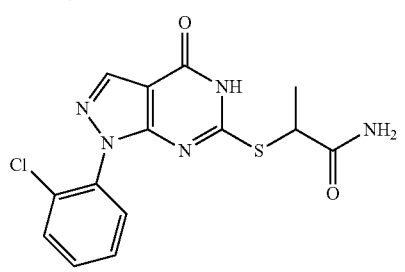
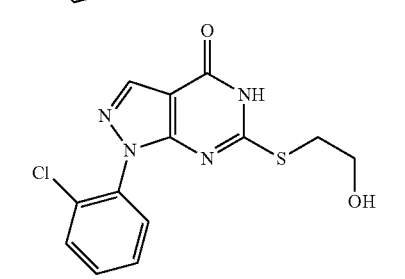
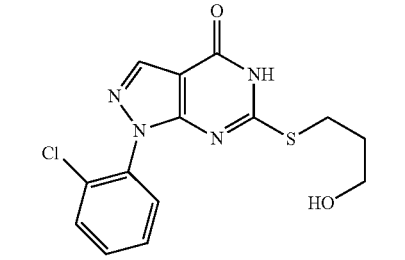
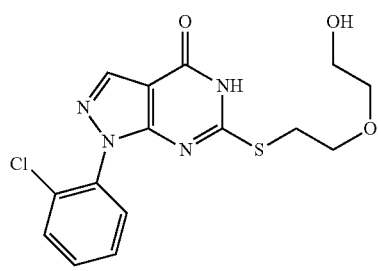

-continued
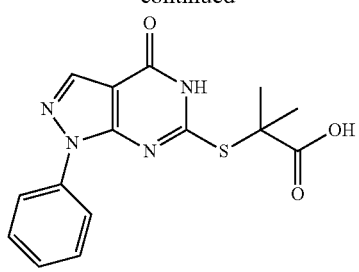
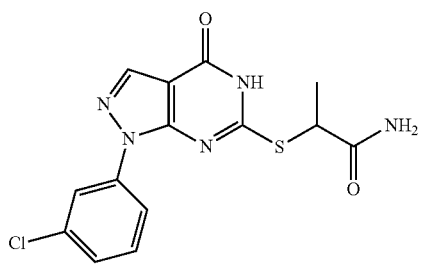
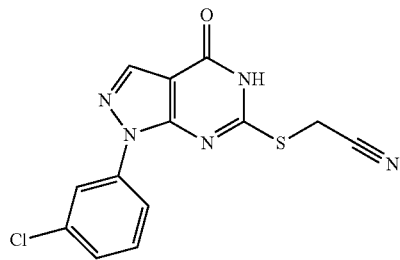
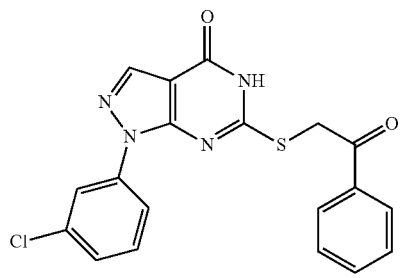
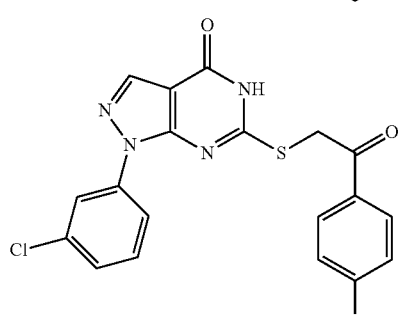
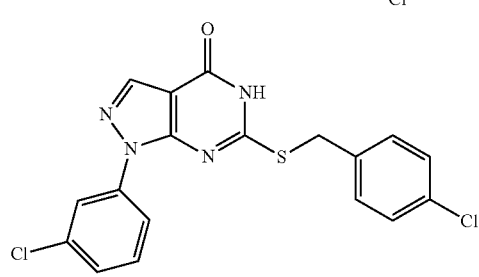
-continued
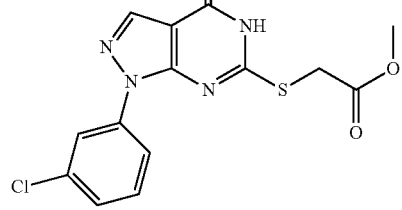
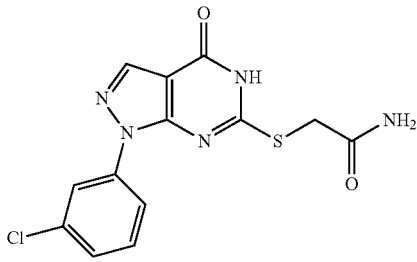
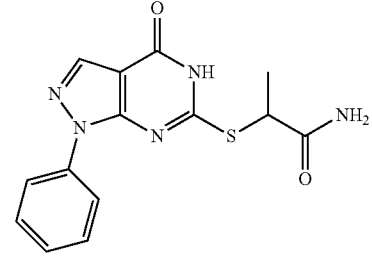
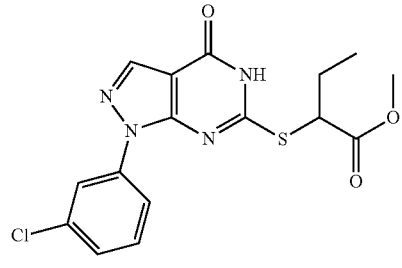
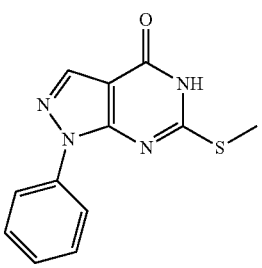
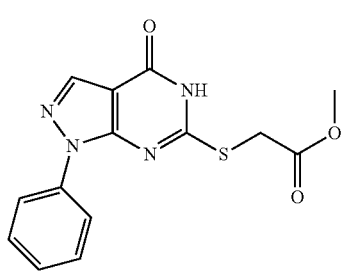

-continued
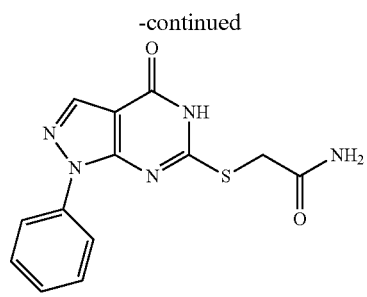
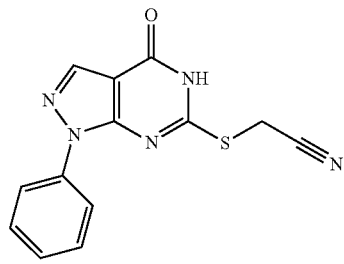
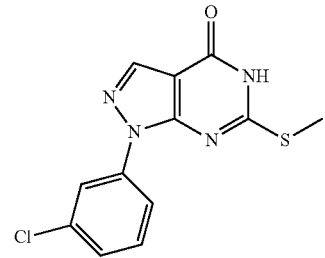
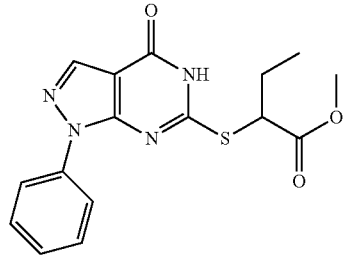
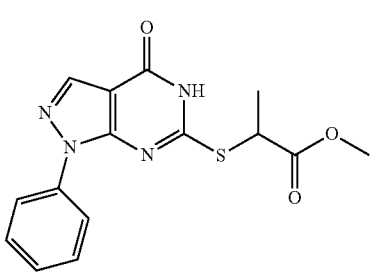
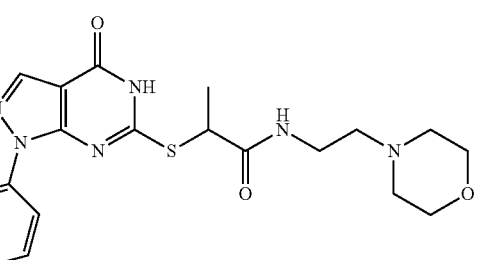
-continued
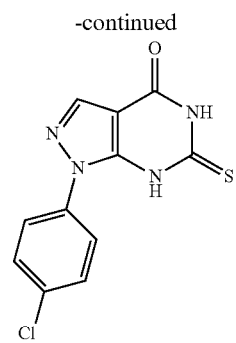
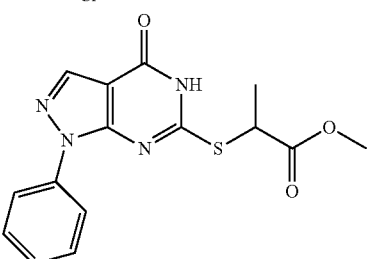
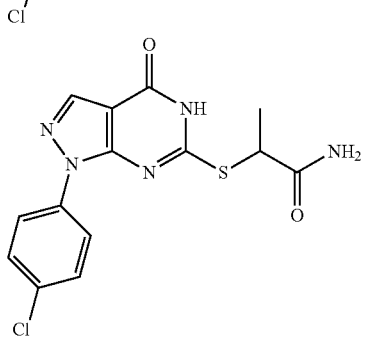
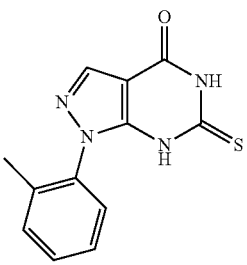
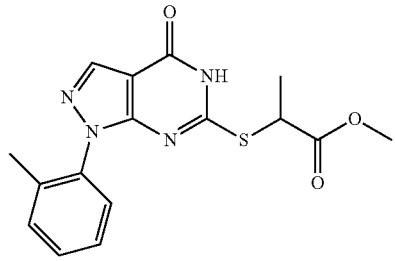
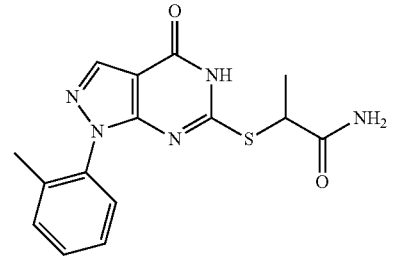

45
-continued
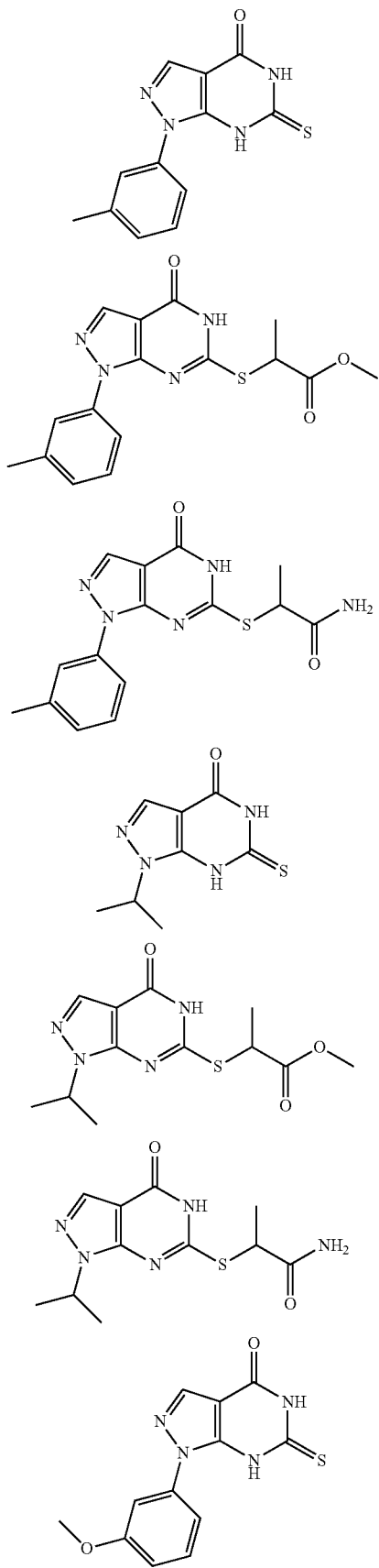
46
-continued
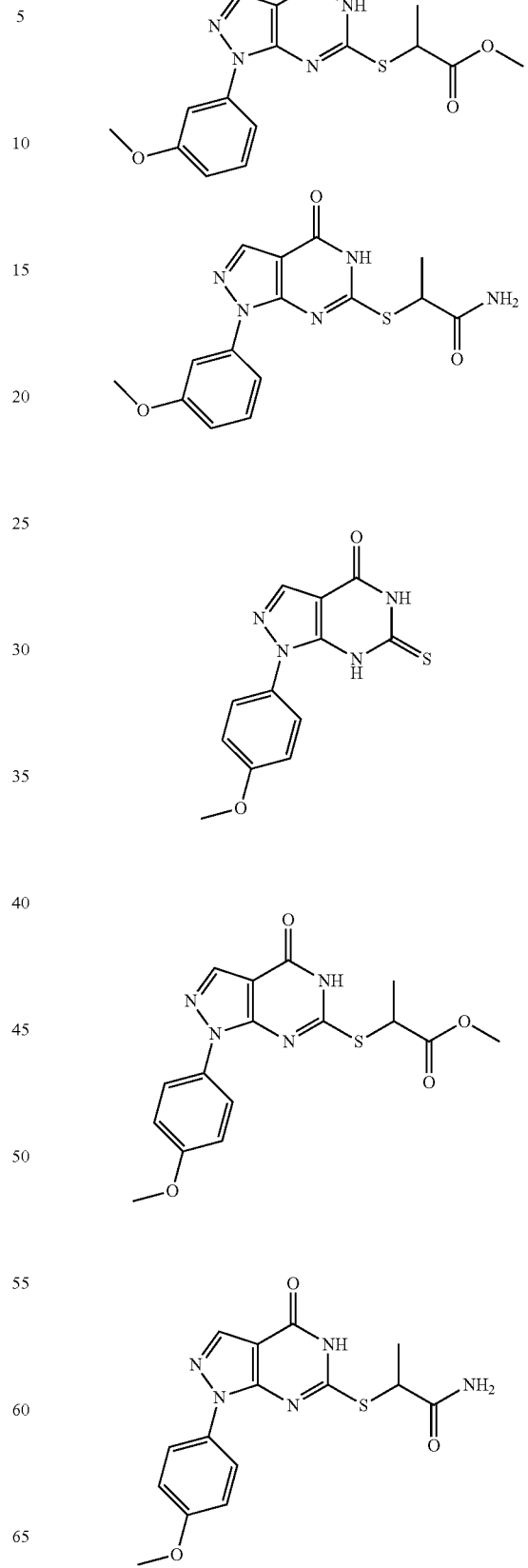

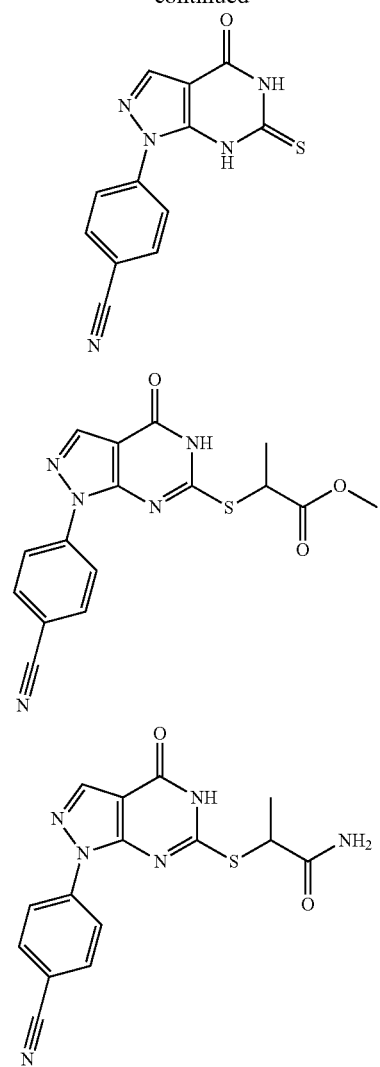
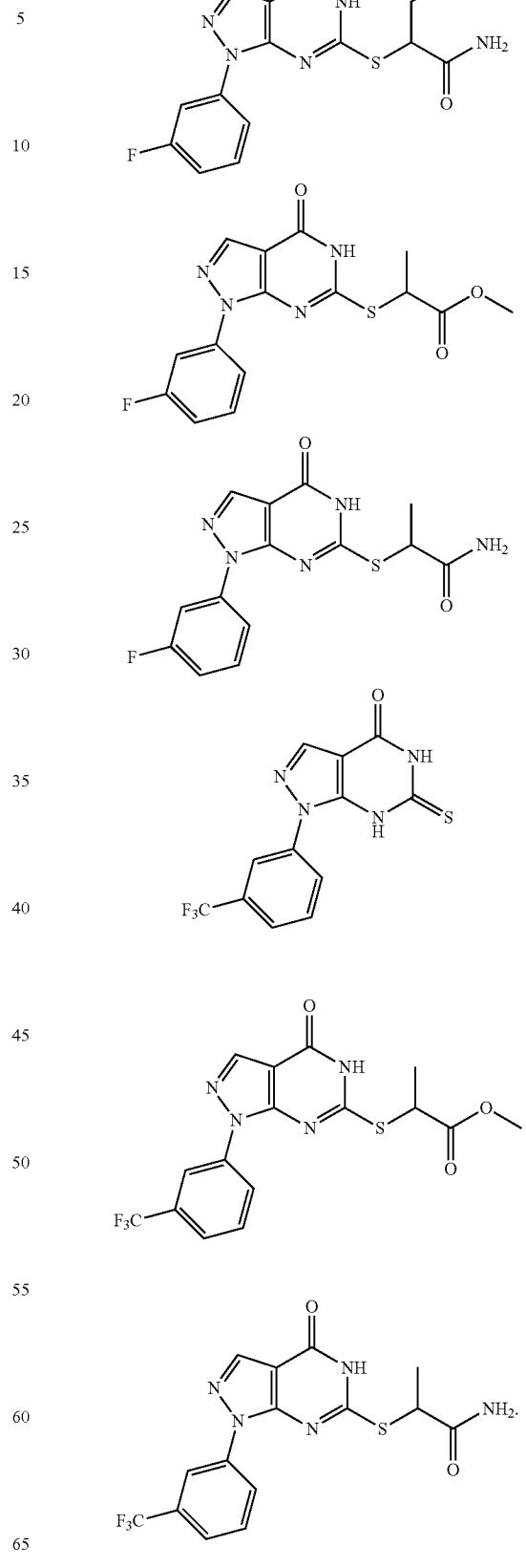

In some embodiments, the compound is not:

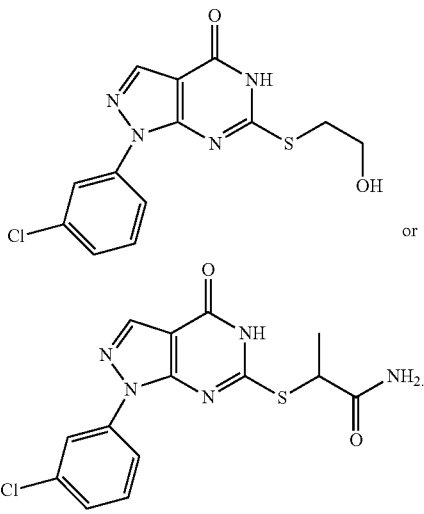

or a. Isomers

Certain compounds may exist in one or more particular geometric, optical, enantiomeric, diastereomeric, epimeric, atropic, stereoisomer, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; a- and β-forms; axial and equatorial forms; boat-, chair-, twist-, envelope-, and half chair-forms; and combinations thereof, hereinafter collectively referred to as "isomers" (or "isomeric forms").

In one embodiment, a compound described herein may be an enantiomerically enriched isomer of a stereoisomer described herein. For example, the compound may have an enantiomeric excess of at least about 10%, 15%, 20%, 25%, 30%, 35%, 40%, 45%, 50%, 55%, 60%, 65%, 70%, 75%, 80%, 85%, 90%, 95%, 96%, 97%, 98%, or 99%. Enantiomer, when used herein, refers to either of a pair of chemical compounds whose molecular structures have a mirror-image relationship to each other.

In one embodiment, a preparation of a compound disclosed herein is enriched for an isomer of the compound having a selected stereochemistry, e.g., R or S, corresponding to a selected stereocenter. For example, the compound has a purity corresponding to a compound having a selected stereochemistry of a selected stereocenter of at least about 60%, 65%, 70%, 75%, 80%, 85%, 90%, 95%, 96%, 97%, 98%, or 99%.

In one embodiment, a composition described herein includes a preparation of a compound disclosed herein that is enriched for a structure or structures having a selected stereochemistry, e.g., R or S, at a selected stereocenter. Exemplary R/S configurations can be those provided in an example described herein.

An "enriched preparation," as used herein, is enriched for a selected stereoconfiguration of one, two, three or more selected stereocenters within the subject compound. Exemplary selected stereocenters and exemplary stereoconfigurations thereof can be selected from those provided herein, e.g., in an example described herein. By enriched is meant at least 60%, e.g., of the molecules of compound in the preparation have a selected stereochemistry of a selected stereocenter. In an embodiment it is at least 65%, 70%, 75%, 80%, 85%, 90%, 95%, 96%, 97%, 98%, or 99%. Enriched refers to the level of a subject molecule(s) and does not connote a process limitation unless specified.

Compounds may be prepared in racemic form or as individual enantiomers or diastereomers by either stereo-specific synthesis or by resolution. The compounds may, for example, be resolved into their component enantiomers or diastereomers by standard techniques, such as the formation of stereoisomeric pairs by salt formation with an optically active base, followed by fractional crystallization and regeneration of the free acid. The compounds may also be resolved by formation of stereoisomeric esters or amides, followed by chromatographic separation and removal of the chiral auxiliary. Alternatively, the compounds may be resolved using a chiral HPLC column. The enantiomers also may be obtained from kinetic resolution of the racemate of corresponding esters using lipase enzymes.

Except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g., C$_3$-alkyl or propyl includes n-propyl and iso-propyl; C$_4$-alkyl or butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol, imine/enamine, amide/imino alcohol, amidine/amidine, nitroso/oxime, thioketone/enethiol, N-nitroso/hydroxyazo, and nitro/aci-nitro.

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

b. Salts

A compound described herein can be in the form of a salt, e.g., a pharmaceutically acceptable salt. The term "pharmaceutically acceptable salt" includes salts of the active compounds that are prepared with relatively nontoxic acids or bases, depending on the particular substituents found on the compounds described herein. Neutral forms of the compounds may be regenerated by contacting the salt with a base or acid and isolating the parent compound in a conventional manner. The parent form of the compound differs from the various salt forms in certain physical properties, such as solubility in polar solvents, but otherwise the salts are equivalent to the parent form of the compound for the purposes of this disclosure. Examples of pharmaceutically acceptable salts are discussed in Berge et al, 1977, "Pharmaceutically Acceptable Salts." J. Pharm. Sci. Vol. 66, pp. 1-19.

For example, if the compound is anionic, or has a functional group which may be anionic (e.g., —COOH may be —COO$^-$), then a salt may be formed with a suitable cation. Examples of suitable inorganic cations include, but are not limited to, alkali metal ions such as $Na^+$ and $K^+$, alkaline earth cations such as $Ca^{2+}$ and $Mg^{2+}$, and other cations. Examples of suitable organic cations include, but are not limited to, ammonium ion (i.e., $NH_4+$) and substituted ammonium ions (e.g., $NH_3R_1^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine.

If the compound is cationic, or has a functional group that may be cationic (e.g., —$NH_2$ may be —$NH_3$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, gluchep tonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Unless otherwise specified, a reference to a particular compound also includes salt forms thereof.

c. Chemically Protected Forms

It may be convenient or desirable to prepare, purify, and/or handle an active compound in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts; 3rd Edition; John Wiley and Sons, 1999). Unless otherwise specified, a reference to a particular compound also includes chemically protected forms thereof.

A wide variety of such "protecting," "blocking," or "masking" methods are widely used and well known in organic synthesis. For example, a compound which has two nonequivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

A hydroxy group may be protected as an ether (—OR) or an ester (—OC(O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—$OC(O)CH_3$, —OAc).

An aldehyde or ketone group may be protected as an acetal ($RCH(OR)_2$) or ketal ($R_2C(OR)_2$), respectively, in which the carbonyl group ($R_2C=O$) is converted to a diether ($R_2C(OR)_2$), by reaction with, for example, a primary alcohol. The aldehyde or ketone group is readily regenerated by hydrolysis using a large excess of water in the presence of acid.

An amine group may be protected, for example, as an amide (—NRC(O)R) or a urethane (—NRC(O)OR), for example, as: a methyl amide (—$NHC(O)CH_3$); a benzyloxy amide (—$NHC(O)OCH_2C_6H_5$, —NH-Cbz); as a t-butoxy amide (—$NHC(O)OC(CH_3)_3$, —NH-Boc); a 2-biphenyl-2-propoxy amide (—$NHCO(O)C(CH_3)_2C_6H_4C_6H_5$, —NH-Bpoc), as a 9-fluorenylmethoxy amide (—NH-Fmoc), as a 6-nitroveratryloxy amide (—NH—Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulphonyl)ethyloxy amide (—NH-Psec); or, in suitable cases (e.g., cyclic amines), as a nitroxide radical (>N—O»).

A carboxylic acid group may be protected as an ester, for example, as: an alkyl ester (e.g., a methyl ester; a t-butyl ester); a haloalkyl ester (e.g., a haloalkyl ester); a trialkylsilylalkyl ester; or an arylalkyl ester (e.g., a benzyl ester; a nitrobenzyl ester); or as an amide, for example, as a methyl amide.

A thiol group may be protected as a thioether (—SR), for example, as: a benzyl thioether; an acetamidomethyl ether (—S—$CH_2NHC(O)CH_3$)

d. Prodrugs and Other Modifications

In addition to salt forms, the present disclosure may also provide compounds that are in a prodrug form. Prodrugs of the compounds described herein are those compounds that readily undergo chemical changes under physiological conditions to provide the compounds described herein. Prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

A compound described herein can also be modified by appending appropriate functionalities to enhance selective biological properties. Such modifications are known in the art and include those that increase biological penetration into a given biological system (e.g., blood, lymphatic system, central nervous system), increase oral availability, increase solubility to allow administration by injection, alter metabolism, and/or alter rate of excretion. Examples of these modifications include, but are not limited to, esterification with polyethylene glycols, derivatization with pivolates or fatty acid substituents, conversion to carbamates, hydroxylation of aromatic rings, and heteroatom substitution in aromatic rings.

3. Pharmaceutical Compositions

The disclosure also provides pharmaceutical compositions comprising a compound of formula (1) (e.g., a compound illustrated above) and a pharmaceutically acceptable carrier.

The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of one skilled in the art of formulations.

The pharmaceutical compositions can be administered to subjects (e.g., humans and other mammals) orally, rectally, parenterally, intracisternally, intravaginally, intraperitoneally, topically (as by powders, ointments or drops), bucally or as an oral or nasal spray. The term "parenterally," as used herein, refers to modes of administration, including intravenous, intramuscular, intraperitoneal, intrasternal, subcutaneous, intraarticular injection and infusion.

Pharmaceutical compositions for parenteral injection comprise pharmaceutically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like, and suitable mixtures thereof), vegetable oils (such as olive oil) and injectable organic esters such as ethyl oleate, or suitable mixtures thereof. Suitable fluidity of the composition may be maintained, for example, by the use of a coating such as lecithin, by the maintenance of the required particle size in the case of dispersions, and by the use of surfactants.

These compositions can also contain adjuvants such as preservative agents, wetting agents, emulsifying agents, and dispersing agents. Prevention of the action of microorganisms can be ensured by various antibacterial and antifungal agents, for example, parabens, chlorobutanol, phenol, sorbic acid, and the like. It also can be desirable to include isotonic agents, for example, sugars, sodium chloride and the like. Prolonged absorption of the injectable pharmaceutical form can be brought about by the use of agents delaying absorption, for example, aluminum monostearate and gelatin.

In some cases, in order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug can depend upon its rate of dissolution, which, in turn, may depend upon crystal size and crystalline form. Alternatively, a parenterally administered drug form can be administered by dissolving or suspending the drug in an oil vehicle.

Suspensions, in addition to the active compounds, can contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations also are prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions can be formulated according to the known art using suitable dispersing or wetting agents and suspending agents. The sterile injectable preparation also can be a sterile injectable solution, suspension or emulsion in a nontoxic, parenterally acceptable diluent or solvent such as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, one or more compounds is mixed with at least one inert pharmaceutically acceptable carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols.

The solid dosage forms of tablets, dragees, capsules, pills, and granules can be prepared with coatings and shells such as enteric coatings and other coatings well-known in the pharmaceutical formulating art. They can optionally contain opacifying agents and can also be of a composition that they release the active ingredient(s) only, or preferentially, in a certain part of the intestinal tract in a delayed manner. Examples of materials useful for delaying release of the active agent can include polymeric substances and waxes.

Compositions for rectal or vaginal administration are preferably suppositories which can be prepared by mixing the compounds with suitable non-irritating carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, can contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Dosage forms for topical or transdermal administration of a compound include ointments, pastes, creams, lotions, gels, powders, solutions, sprays, inhalants or patches. A desired compound is admixed under sterile conditions with a pharmaceutically acceptable carrier and any needed preservatives or buffers as may be required. Ophthalmic formulation, eardrops, eye ointments, powders and solutions are also contemplated as being within the scope of this disclosure.

The ointments, pastes, creams and gels may contain, in addition to an active compound, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds, lactose, talc, silicic acid, aluminum hydroxide, calcium silicates and polyamide powder, or mixtures of these substances. Sprays can additionally contain customary propellants such as chlorofluorohydrocarbons.

Compounds also can be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds, stabilizers, preservatives, and the like. The preferred lipids are the natural and synthetic phospholipids and phosphatidylcholines (lecithins) used separately or together. Methods to form liposomes are known in the art. See, for example, Prescott, Ed., Methods in Cell Biology, Volume XIV, Academic Press, New York, N. Y., (1976), p 33 et seq.

Dosage forms for topical administration of a compound described herein include powders, sprays, ointments and inhalants. The active compound is mixed under sterile conditions with a pharmaceutically acceptable carrier and any needed preservatives, buffers or propellants. Ophthalmic formulations, eye ointments, powders and solutions are also contemplated as being within the scope of this disclosure. Aqueous liquid compositions may also be useful.

4. Methods of Treatment

Compounds of formula (I) and pharmaceutical compositions comprising compounds of formula (I) may be used to treat disorders associated with DAPKs and PIMKs.

For example, disclosed herein are methods of treating cardiac diseases such as hypertension and pulmonary hypertension, stroke, an ischemia-reperfusion injury (such that cerebral ischemia reperfusion injury, or a reperfusion injury of the kidney, liver or heart), erectile dysfunction, premature labor, pre-eclampsia, migraine, asthma, diarrhea, irritable bowel syndrome, and peripheral artery disease. The methods involve administering to a subject in need of treatment a therapeutically effective amount of a compound of formula (I) or a pharmaceutical composition comprising a compound of formula (I).

Also disclosed herein is a method of treating cancer in a subject in need of treatment, comprising administering to the subject a therapeutically effective amount of a compound of formula (I) or a pharmaceutical composition comprising a compound of formula (I). The compounds and compositions described herein can be used to treat a subject having any type of cancer, for example those described by the National Cancer Institute. The cancer can be a carcinoma, a sarcoma, a myeloma, a leukemia, a lymphoma or a mixed type. Exemplary cancers described by the National Cancer Institute include but are not limited to:

Digestive/gastrointestinal cancers such as anal cancer; bile duct cancer; extrahepatic bile duct cancer; appendix cancer; carcinoid tumor, gastrointestinal cancer; colon cancer; colorectal cancer including childhood colorectal cancer; esophageal cancer including childhood esophageal cancer; gallbladder cancer; gastric (stomach) cancer including childhood gastric (stomach) cancer; hepatocellular (liver) cancer including adult (primary) hepatocellular (liver) cancer and childhood (primary) hepatocellular (liver) cancer; pancreatic cancer including childhood pancreatic cancer; sarcoma, rhabdomyosarcoma; islet cell pancreatic cancer; rectal cancer; and small intestine cancer;

Endocrine cancers such as islet cell carcinoma (endocrine pancreas); adrenocortical carcinoma including childhood adrenocortical carcinoma; gastrointestinal carcinoid tumor; parathyroid cancer; pheochromocytoma; pituitary tumor; thyroid cancer including childhood thyroid cancer; childhood multiple endocrine neoplasia syndrome; and childhood carcinoid tumor;

Eye cancers such as intraocular melanoma; and retinoblastoma;

Musculoskeletal cancers such as Ewing's family of tumors; osteosarcoma/malignant fibrous histiocytoma of the bone; childhood rhabdomyosarcoma; soft tissue sarcoma including adult and childhood soft tissue sarcoma; clear cell sarcoma of tendon sheaths; and uterine sarcoma;

Breast cancer such as breast cancer including childhood and male breast cancer and breast cancer in pregnancy;

Neurologic cancers such as childhood brain stemglioma; brain tumor; childhood cerebellar astrocytoma; childhood cerebral astrocytoma/malignant glioma; childhood ependymoma; childhood medulloblastoma; childhood pineal and supratentorial primitive neuroectodermal tumors; childhood visual pathway and hypothalamic glioma; other childhood brain cancers; adrenocortical carcinoma; central nervous system lymphoma, primary; childhood cerebellar astrocytoma; neuroblastoma; craniopharyngioma; spinal cord tumors; central nervous system atypical teratoid/rhabdoid tumor; central nervous system embryonal tumors; and childhood supratentorial primitive neuroectodermal tumors and pituitary tumor;

Genitourinary cancers such as bladder cancer including childhood bladder cancer; renal cell (kidney) cancer; ovarian cancer including childhood ovarian cancer; ovarian epithelial cancer; ovarian low malignant potential tumor; penile cancer; prostate cancer; renal cell cancer including childhood renal cell cancer; renal pelvis and ureter, transitional cell cancer; testicular cancer; urethral cancer; vaginal cancer; vulvar cancer; cervical cancer; Wilms tumor and other childhood kidney tumors; endometrial cancer; and gestational trophoblastic tumor; Germ cell cancers such as childhood extracranial germ cell tumor; extragonadal germ cell tumor; ovarian germ cell tumor;

Head and neck cancers such as lip and oral cavity cancer; oral cancer including childhood oral cancer (e.g., oral squamous cell carcinoma); hypopharyngeal cancer; laryngeal cancer including childhood laryngeal cancer; metastatic squamous neck cancer with occult primary; mouth cancer; nasal cavity and paranasal sinus cancer; nasopharyngeal cancer including childhood nasopharyngeal cancer; oropharyngeal cancer; parathyroid cancer; pharyngeal cancer; salivary gland cancer including childhood salivary gland cancer; throat cancer; and thyroid cancer;

Hematologic/blood cell cancers such as a leukemia (e.g., acute lymphoblastic leukemia including adult and childhood acute lymphoblastic leukemia; acute myeloid leukemia including adult and childhood acute myeloid leukemia; chronic lymphocytic leukemia such as B Cell chronic lymphocytic leukemia; chronic myelogenous leukemia; and hairy cell leukemia); a lymphoma (e.g., AIDS-related lymphoma; cutaneous T-cell lymphoma; Hodgkin's lymphoma including adult and childhood Hodgkin's lymphoma and Hodgkin's lymphoma during pregnancy; non-Hodgkin's lymphoma including adult and childhood non-Hodgkin's lymphoma and non-Hodgkin's lymphoma during pregnancy; mycosis fungoides; Sezary syndrome; Waldenstrom's macroglobulinemia; primary mediastinal large B cell lymphoma; mantle cell lymphoma; diffuse large B cell lymphoma; and primary central nervous system lymphoma); and other hematologic cancers (e.g., chronic myeloproliferative disorders; multiple myeloma/plasma cell neoplasm; myelodysplastic syndromes; and myelodysplastic/myeloproliferative disorders);

Lung cancer such as non-small cell lung cancer; and small cell lung cancer;

Respiratory cancers such as adult malignant mesothelioma; childhood malignant mesothelioma; malignant thymoma; childhood thymoma; thymic carcinoma; bronchial adenomas/carcinoids including childhood bronchial adenomas/carcinoids; pleuropulmonary blastoma; non-small cell lung cancer; and small cell lung cancer;

Skin cancers such as Kaposi's sarcoma; Merkel cell carcinoma; melanoma; and childhood skin cancer;

AIDS-related malignancies;

Other childhood cancers, unusual cancers of childhood and cancers of unknown primary site;

and metastases of the aforementioned cancers can also be treated or prevented in accordance with the methods described herein.

In some embodiments, the cancer may be a cancer associated with a PIM kinase, such as PIM1 or PIM3. See, for example, Magnuson et al. *Future Oncol.* 2010 6(9) 1461-1478, and Mukaida et al. *Cancer Sci.* 2011, 102(8) 1437-1442. The methods described herein may be suited for lymphomas, myelomas, leukemias, prostate cancer, breast cancer, non-small cell lung cancer, colorectal cancer, pancreatic cancer, head and neck cancer, gastric cancer, liver cancer or stomach cancer. For example, the methods may be suited for squamous cell carcinoma of the head or neck, nasopharyngeal cancer, oral squamous cell carcinoma, Ewing's sarcoma, acute myeloid leukemia, B Cell chronic lymphocytic leukemia, primary mediastinal large B cell lymphoma, mantle cell lymphoma or diffuse large B cell lymphoma.

The following examples are intended to be illustrative, and should be considered to be non-limiting.

EXAMPLES

Materials and Methods.

All reagents were purchased from commercial sources and used without further purification. $^1$H NMR experiments were performed on a Varian 500 MHz instrument.

Kinase Assay procedure: All kinase assays (whether including ZIPK, MLCK or ROK) were initiated by addition to LC20 substrate and protein kinase of 5×ATP solution (1.5 mM ATP, 10 µCi/[β-$^{32}$P]-ATP (only for radioactive assays), 5 mM MgCl$_2$, 125 mM HEPES, pH 7.4). The phosphorylation of LC20 was initiated by addition of protein kinase and incubated at 30° C. Incubation times varied and were chosen to ensure a linear time course of phosphorylation. Reactions were quenched with 20 mM H$_3$PO$_4$ and spotted onto P81 phosphocellulose disks (Whatman). After extensive washing with 20 mM H$_3$PO$_4$, radioactivity on the P81 disk was quantified by Čerenkov counting.

Example 1. Library Construction and Screening

The screen is generally illustrated in FIG. 1A and summarized in FIG. 1B.

A collection of 10000 compounds was initially selected from commercially available compounds using a previously described set of filters (Fadden et al. (2010) *Chem. Biol.* 17, 686-694). Two experienced medicinal chemists further refined the set down to 4000 compounds in order to remove structural liabilities not easily reduced to algorithmic analysis. Drug candidates (3379 compounds) were purchased from sources associated with emolecules.com and were dissolved in DMSO as 10 mM solutions.

Expression of GFP Fusion Proteins.

HEK293 cells were plated in 15-cm tissue culture plates and incubated overnight at 37° C. under 5% CO$_2$. GFP fusion constructs were transfected into cells at a 1:3 ratio with Fugene HD (Roche) transfection reagent. After 24-48 hours, cell culture media was aspirated, and cells were scraped off the plate using PBS. Cells were pelleted by centrifugation (2,000 rpm, 2 min) and pellets were flash frozen in an EtOH/dry ice bath and stored at −80° C. GFP fusion protein was extracted from cell pellets using mammalian lysis buffer (0.1% Triton; NaCl, 150 mM; MgCl$_2$, 60 mM; Tris HCl, pH 7.5, 25 mM; Microcystin, 1 µM; protease inhibitor tablet) for 30 min over ice. Supernatant was isolated from cell debris by centrifugation (4,000 rpm, 5 min). The supernatant was then used for all subsequent screening and titration experiments.

Preparation of γ-Linked ATP Sepharose Media.

Dry CNBr-Activated Sepharose 4B media (28.6 g, GE Healthcare) was equilibrated in HCl (1 mM, 333 mL) for 5-15 min, isolated by filtration, and then washed with HCl (1 mM, 600 mL) followed by H$_2$O (333 mL). The media was combined with reaction mixture A (NaHCO$_3$, 0.97 g; NaCl, 3.4 g; H$_2$O, 115 mL; 1,4-dioxane, 29 mL; 1,10-diaminodecane, 3.6 g; ethanolamine, 3.6 mL) and shaken for 2 h. Meanwhile, reaction mixture B (H$_2$O, 143 mL; ATP, disodium salt, 7 g; 1-methylimidazole, 5.2 mL; EDC, 12 g) was stirred for 1 h. Mixture A was removed by filtration and the media washed with HCl (1 mM, 600 mL) and then H$_2$O (333 mL). Mixture B and media were combined and shaken for 24 h. The resulting ATP Sepharose media was isolated by filtration and washed with HCl (1 mM, 600 mL) and then H$_2$O (333 mL). The media was stored at 4° C. in phosphate buffer (0.1 M, pH 7.4) containing NaN$_3$ (3 mM).

Drug Candidate Screening and Titrations.

Crude lysates containing recombinant purinomic GFP fusion proteins were combined with ATP Sepharose media (1:1 slurry, >50,000 fluorescence counts per 50 µL of slurry) in lysis buffer (0.1% Triton; NaCl, 150 mM; MgCl$_2$, 60 mM; Tris HCl, pH 7.5, 25 mM; Microcystin, 1 µM; protease inhibitor tablet) for 0.5 h at 4° C. The buffer was removed by filtration and the media was washed with high salt wash buffer (Tris, 50 mM; NaCl, 1 M; MgCl$_2$, 60 mM; DTT, 1 mM) (3×resin volume) followed by low salt wash buffer (LSWB) (Tris, 50 mM; NaCl, 150 mM; MgCl$_2$, 60 mM; DTT, 1 mM) (3×resin volume). LSWB (1×resin volume) was then added to the resin and the resulting 1:1 slurry was partitioned into a 96-well filter plate (Corning 3504) (50 µL per well). Positive control: to each well was added 50 µL of ATP solution (2-200 mM in LSWB with 10% DMSO). Drug candidate screen: to each well was added 50 µL of drug candidate (900 µM in LSWB with 10% DMSO). Drug candidate titrations: to each well was added 50 µL of HS38 or ML-7 (Sigma Aldrich) solution (0.1-300 µM in LSWB with 10% DMSO). After 10 min of incubation at room temperature, the filtrates were isolated by centrifugation (1000 rpm, 2 min) into a black 96-well catch plates (Costar 3915). Fluorescence in each well was determined using a plate reader (Perkin Elmer Victor X2 Multilabel Reader, Lamp filter 485 nm, Emission filter 535 nm).

Calculation of Z' Factor for Assay Development.

The average fluorescence signal from the 70 mM ATP control defined maximum ZIPKΔ-eGFP displacement from the ATP-Sepharose resin, and average of 10% DMSO in buffer controls defined minimum displacement. These parameters were used to determine the Z' factor:

$$Z' \text{ factor} = 1 - \frac{3 \times (\sigma_p + \sigma_n)}{|\mu_p - \mu_n|}$$

where $\mu_p$ is the mean for maximum displacement, $\mu_p$ is standard deviation for maximum displacement, $\mu_n$ is the mean for minimum displacement, and $\mu_n$ is the standard deviation for minimum displacement. The Z' factor for this screen is 0.53, which is above the threshold (0.5) for an excellent assay (Zhang et al. (1999) *J. Biomol. Screen.* 4, 67-73).

Results.

Screening:

HS38 competitively eluted GFP-ZIPK resulting in >4-fold increase in fluorescence above background (FIG. 1A (5)). Significant elution of GFP-ZIPK by 15 members of the library was confirmed by western blot analysis. Of these 15 hits, HS38 was the most potent (FIG. 1A (6)).

Figure 2:
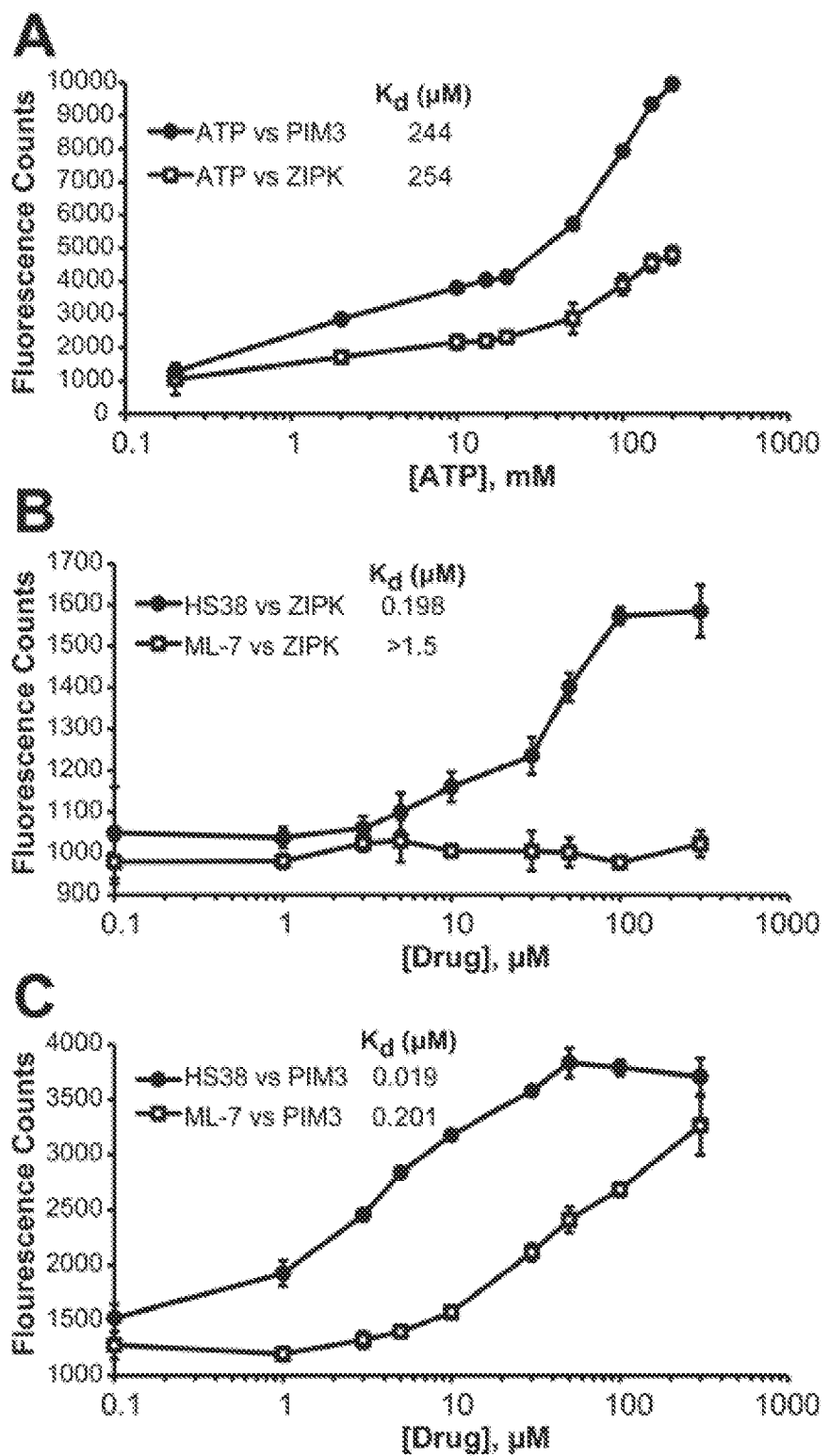
FIG. 2 shows titration curves generated by elution of GFP-ZIPK and PIM3-GFP from γ-linked ATP sepharose media using soluble ATP, HS38, and ML-7 and corresponding apparent K$_d$ values (mean S.D., n=3). A. ATP elutions. B. HS38 eluted GFP-ZIPK while ML-7 did not. C. Both HS38 and ML-7 eluted PIM3-GFP.

Titrations:

Titration curves were generated from the systematic elution of GFP-ZIPK and PIM3 with C-terminal GFP tag (PIM3-GFP) from γ-linked ATP Sepharose media with solution phase ATP (positive control), HS38, and the commercially available non-selective kinase inhibitor ML-7 (FIG. 2). ML-7 was previously identified as a potential hit during the process of screen optimization while screening a truncated form of ZIPK, with C-terminal GFP tag (ZIPKΔ$^{13-289}$-GFP), against commercially available libraries (Lopac™ Library, Sigma, 1280 members and BioFocus™ Library, BioFocus DPI, 3120 members). Apparent dissociation constants describing the affinity of GFP-ZIPK and PIM3-GFP for small molecule inhibitors (HS38 and ML-7) were calculated using a previously described method (Haystead (2006) *Curr. Top. Med. Chem.* 6, 1117-1127). Briefly, binding isotherms were generated by titration of GFP fusion proteins from ATP Sepharose media with inhibitor solutions as described above (Drug Screening and Titrations). The concentrations of inhibitor that eluted 50% of each target protein (EC$_{50}$ values) were derived from binding isotherms. Values for K$_d$ were calculated from the following equation $$K_d = \frac{EC_{50}}{1 + \frac{[\text{resin ligand}]}{K_m}}$$

where [resin ligand] is the local concentration of immobilized ATP (~10 mM) and K$_m$ is the Michaelis constant describing the ATP dependence of purine utilizing proteins (~50 µM).

Sigmoidal isotherms generated by elution of GFP-ZIPK and PIM3-GFP with soluble ATP confirm that both were bound to the ATP media through non-covalent association with their ATP binding pockets. Interestingly, while HS38 elution of GFP-ZIPK produced a sigmoidal curve and an apparent K$_d$ of 198 nM, ML-7 failed to elute full length GFP-ZIPK. This suggests that, although ML-7 binds ZIPKΔ$^{13-289}$-GFP in an ATP competitive manner, this activity is not recapitulated with the full length construct. A possible explanation is that the presence of a C-terminal regulatory domain on full length ZIPK, which is essential for regulating and targeting its activity in vivo, but not present in the truncate, renders ML-7 affinity insufficient to displace full length ZIPK from immobilized ATP (Weitzel et al. (2011) *Cell. Signal.* 23, 297-303). This finding demonstrates that full length constructs should be screened whenever possible. In contrast, both HS38 and ML-7 eluted PIM3-GFP from ATP affinity media (apparent K$_d$=19 nM, and 201 nM respectively).

Example 2. Synthesis of (2-((1-(3-chlorophenyl)-4-oxo-4,5-dihydro-1H-pyrazolo[3,4-d]pyrimidin-6-yl) thio)propanamide 1-(3-chlorophenyl)-6-mercapto-1,3a,7,7a-tetrahydro-4H-pyrazolo[3,4-d]pyrimidin-4-one (500 mg, 1.8 mmol, Enamine EN300-27274) was dissolved in $CH_2Cl_2$ (5 mL) and treated with diisopropylethylamine (630 µL) and methyl 2-bromopropionate (329 mg, 1.97 mmol). After stirring for 24 h, the mixture was adsorbed onto silica (4 g) and added to a silica gel column (18×2.5 cm), flushed with $CH_2Cl_2$ (150 mL), and chromatographed (10% MeOH in $CH_2Cl_2$, 400 mL). The resulting solid was triturated with water and filtered to give methyl 2-((1-(3-chlorophenyl)-4-oxo-3a,4,7,7a-tetrahydro-1H-pyrazolo[3,4-d]pyrimidin-6-yl)thio)propanoate (574 mg, 88%) as a white powder.

Example 3. Kinome Profiling

HS38 was evaluated using a $^{33}$P-ATP filter-binding assay by the International Centre for Kinase Profiling (University of Dundee) against 124 purified protein kinases representing all gene family members within the human kinome, using previously described methods (Bain et al. (2007) *Biochem. J.* 408, 297-315). See FIG. 3A. These studies showed HS38 to be highly specific for DAPK1 ($IC_{50}$=200 nM, 89% inhibition at 10 µM) and the closely related PIM3 kinase ($IC_{50}$=200 nM, 76% inhibition at 10 µM). HS38 displayed no activity against Src or Abl kinase (0% inhibition at 10 µM) and little activity against EGFR-TK (41% inhibition at 10 µM), suggesting that structural components of HS38 at the thioether and aryl regions around the pyrazolo[3,4-d]pyrimidinone core are important for DAPK and PIM3 affinity and are sufficient to distinguish the selectivity profile of HS38 from other inhibitors.

Figure 3:
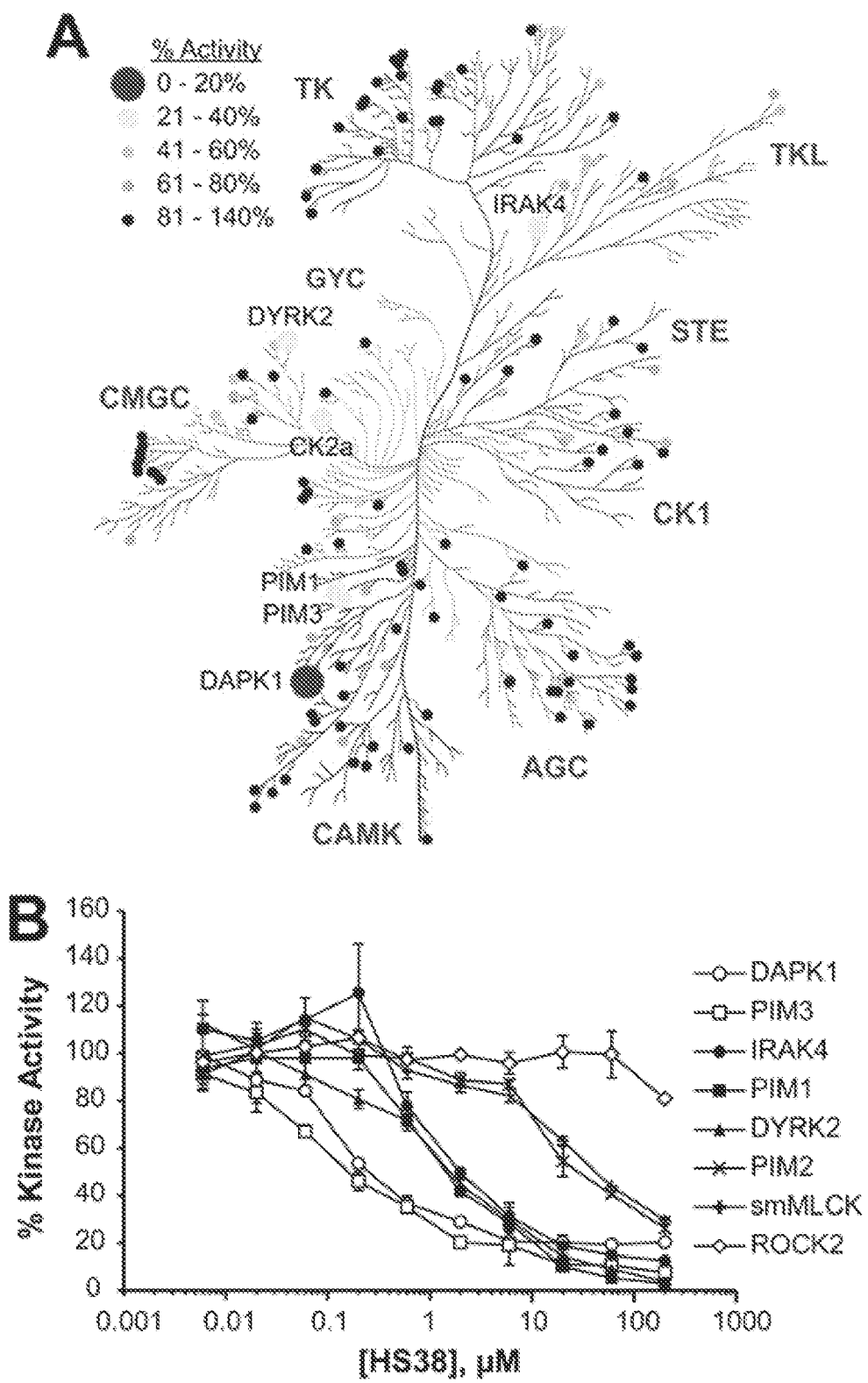
FIG. 3 shows: (A) Kinome dendrogram showing selectivity of HS38. Circles signify residual % enzyme activity in the presence of HS38 (10 μM). Dendrogram was created using the RBC Kinase Activity Mapper (Reaction Biology Corp.). (B) Kinase inhibition isotherms generated from radioactive ($^{33}$P-ATP) filter-binding assay of HS38 against eight kinases. HS38 was most potent against DAPK1 and PIM3 (mean±S.D., n=2).

The results of the initial kinome profile were validated in duplicate against eight kinases (FIG. 3B). HS38 was most potent against DAPK1 and PIM3, ~10 fold less potent against IRAK4 and PIM, ~100 fold less potent against PIM2 and SM myosin light chain kinase (smMLCK), and completely inactive against ROK2 (Table 1). These two latter kinases are significant in the context of SM contractility because $Ca^2$ sensitization is linked to increased RLC20 phosphorylation by smMLCK, by ZIPK itself, or by ROK induced deactivation of MYPT1 either directly or indirectly by activation of ZIPK.[3] Therefore it was important to establish that HS38 does not act upon ROK or smMLCK. This being the case, it is unlikely that activity of HS38 on SM contractility would be due to off-target inhibition of ROK or smMLCK.

TABLE 1

$IC_{50}$ values (mean ± S.D., n = 2) and residual % activity derived from kinase inhibition isotherms (FIG. 3B).

| Kinase | $IC_{50}$ (µM) | % Activity (10 µM HS38) |
|---|---|---|
| DAPK1 | 0.20 ± 0.02 | 11 |
| PIM3 | 0.20 ± 0.06 | 24 |
| IRAK4 | 1.4 ± 0.4 | 20 |
| PIM1 | 1.7 ± 0.1 | 23 |
| DYRK2 | 1.8 ± 0.6 | 21 |
| PIM2 | 18 ± 8 | 64 |
| smMLCK | 19 ± 3 | 71 |
| ROK2 | >200 | 91 |

Example 4. Effects of HS38 on SM Contractility and Phosphorylation of RLC20 and MYPT1

Tissue Preparation and Force Measurements. All protocols and procedures for tissue harvest were carried out according to protocols approved by the Animal Care and Use Committees at the University of Virginia and Duke University. Helical strips of mouse aorta or strips of rabbit ileum were dissected, (~400 µm wide, 2 mm long) and mounted between two tungsten hooks on a bubble plate for force measurements (Horiuti (1988) *J. Physiol.—London* 398, 131-148). Isometric force measurements were performed on mouse aortas as previously described (Lontay et al. (2010) *J. Biol. Chem.* 285, 29357-29366). Intact strips of mouse abdominal aorta were challenged with phenylephrine following pretreatment with HS38 or diluent, DMSO or HS38 and DMSO were added after maximal phenylephrine-induced force was achieved and force output measured. For evaluation of HS38 on $Ca^2$ sensitized force, after measurements of contractions induced by high K+(154 mM), ileum strips were permeabilized with either *Staphylococcus aureus*-toxin (500 U $ml^{-1}$ for rabbit) for 40 min at room temperature in relaxing solution (G1) containing MgATP (4.5 mM) and EGTA (1 mM) as described previously (Kitazawa et al. (1991) *Proc. Natl. Acad. Sci. U.S.A* 88, 9307-9310) or b-escin (75 µM, Sigma-Aldrich) for 10 min. $Ca^{2+}$ stores were depleted in muscle strips with the addition of Ca-ionophore A23187 (10 µM, Calbiochem) for 10 min in G1 solution. For $Ca^{2+}$ activating solutions, EGTA (10 mM) and a calculated amount of Ca-methanesulfonate was added to give the desired free $Ca^{2+}$ concentration ((Horiuti (1988). *J. Physiol.—London* 398, 131-148).

To examine the effect of ZIPK inhibition on sensitized force, muscle strips were stimulated with an intermediate calcium concentration solution (pCa 6.5). Once force reached a plateau, strips were $Ca^{2+}$-sensitized by the addition of the agonist carbachol (5 µM). Up to 2 µM of GTP was added together with the sensitizing agonist to compensate for possible loss of GTP during permeabilization. At the plateau of Ca-sensitized force (5-10 min upon stimulation), the ZIPK inhibitor, HS38 (50 µM) or diluent (0.1% DMSO) was added and the force relaxation time course was recorded. Tissue samples were frozen 20 min after the addition of HS38 for biochemical assays of RLC20 and MYPT1 phosphorylation.

To examine the $Ca^{2+}$-independent kinase activity of ZIPK, strips were pre-incubated with either HS38 (50 µM) or DMSO (0.1%) for 5 min in relaxing (G1) solution followed by addition of microcystin-LR (10 µM) for 35 min.

MYPT1 and RLC20 phosphorylation: To examine the phosphorylation of MYPT1 and RLC20, rabbit ileum SM strips were treated as described above and previously reported. (Gong et al. (1995) *J. Physiol.—London* 486, 113-122; Kitazawa et al. (1989) *J. Biol. Chem.* 264, 5339-5342; Kobayashi et al. (1991) *Am. J. Physiol.* 260, C364-C370). Following the stimulation protocols, muscle strips were immediately frozen by immersion in −80° C. acetone with trichloroacetic acid (10% w/v) and stored at −80° C. Frozen strips were then washed in acetone and dried, homogenized in sample buffer in a glass-glass, hand-operated homogenizer. Phosphorylation of MYPT1 Thr696 and of RLC20 was determined by SDS-PAGE and Western blotting.

For Western blots, tissues and cultured cells were lysed in 1% SDS, NaCl (300 mM), Tris-HCl (50 mM, pH 7.5), subjected to SDS-PAGE, transferred to polyvinylidene difluoride membrane (Millipore) and visualized using the Odyssey System (Li-Cor). For Odyssey imaging, the membranes were blocked with Odyssey Blocking Buffer and then subjected to anti-MYPT1 (1:2,000) (BD Transduction), phospho-MYPT1 (Thr696) (1:1,000) (Millipore), RLC20 (1:2000) (Sigma) and phospho-RLC20 (1:1000) (Cell Signaling Technology) antibodies. Antibodies were diluted in appropriate blocking buffer. The membranes were washed in TBS with 0.05% Tween 20. Primary antibodies were visualized using secondary antibodies conjugated to Alexa 680 (Invitrogen) or IRDye800 (Li-Cor).

Cell Culture:

Mouse aortic SM cells were prepared. The cell line was cultured in AmnioMax medium (Gibco) supplemented with 10% embryonic stem cell-qualified fetal bovine serum (Invitrogen) and penicillin-streptomycin (Invitrogen). Cultured cells were maintained at 37° C. in a humidified chamber supplemented with 5% $CO_2$. Cells were seeded on 100 mm culture dishes. Prior to experimental conditions, cells were starved for 16 h with serum free medium. Subconfluent, serum-starved smooth muscle cells were treated with sphingosine-1-phosphate (0.25 µM) for 5 min followed by treatment with HS38 (50 µM) or diluent (0.1% DMSO) for 30 min.

Figure 4:
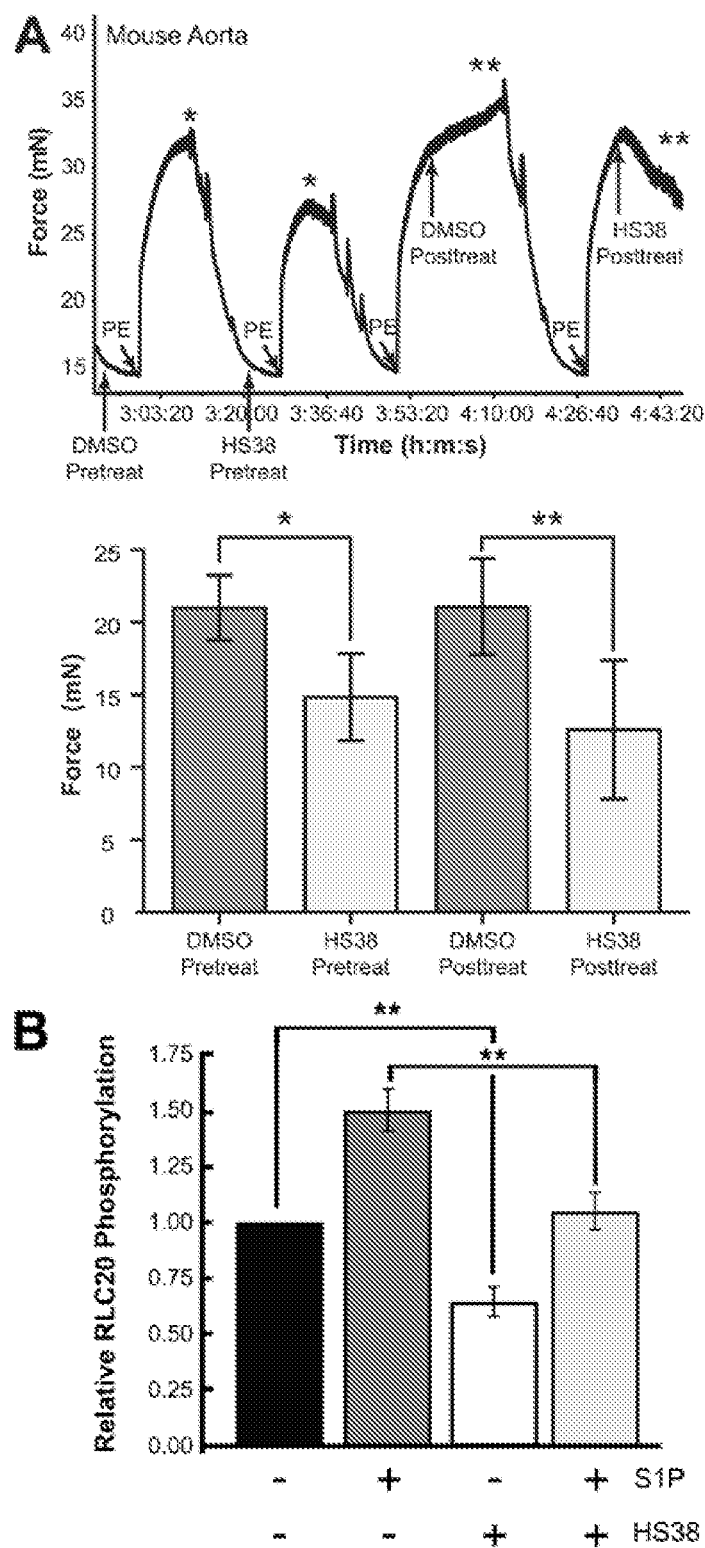
FIG. 4 shows that HS38 reduced contractile forces generated by intact mouse aorta and decreased RLC20 phosphorylation in aortic smooth muscle cells. A. Typical myograph force trace showing the effect of HS38 on intact mouse aorta contractility. The maximum contractile force of PE-induced contraction was reduced by approximately 30% when HS38 (10 μM) was added five minutes prior to PE addition and by approximately 40% when added ten minutes after PE addition. B. Serum-starved aortic SM cells were treated with SIP (0.25 μM) and HS38 (50 μM) for 30 min. HS38 significantly decreased RLC20 phosphorylation at the basal (unstimulated) state (p<0.0002, n=8) and SIP stimulated state (p<0.004, n=8).

Results:

When administered before contraction, HS38 decreased the maximum contractile force achieved from application of the $\alpha_1$-adrenergic receptor agonist, phenylephrine (PE), in a reversible manner. HS38 also decreased force maintenance when administered after PE-induced contraction (FIG. 4A). Additionally, incubation of human aortic SM cells in HS38 significantly reduced relative RLC20 phosphorylation in both the basal and sphingosine 1-phosphate (SIP) activated states (FIG. 4B) (Watterson et al. (2005) *Cell. Signal.* 17, 289-298).

Figure 5:
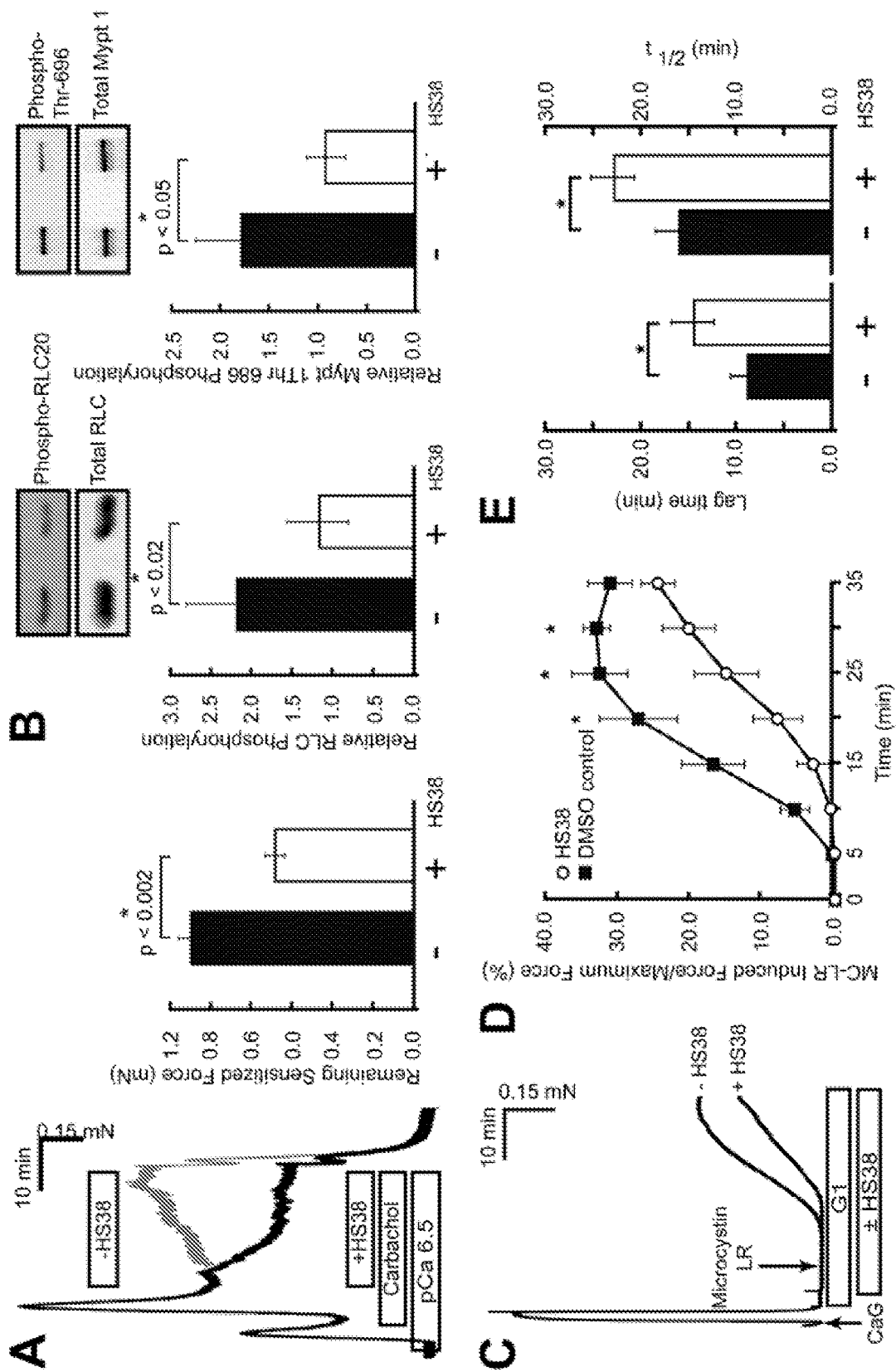
FIG. 5 shows that HS38 reduced the contractile force, RLC20 phosphorylation, and MYPT1 phosphorylation in Ca$^{2+}$ sensitized rabbit ileum (A-B) and decreased the kinetics of Ca$^{2+}$ independent force development (C-D). A. Typical force trace and graphical representation showing the effect of HS38 (50 μM) on carbachol-induced, Ca$^{2+}$ sensitized force in α-toxin permeabilized rabbit ileum. HS38 induced an approximate 30% decrease in the plateaued force at 20 min. (mean S.E., n=7). B. Western blot analysis of RLC20 and MYPT1 Thr696 phosphorylation following treatment with HS38 (50 μM). HS38 significantly reduced both RLC20 and MYPT phosphorylation levels associated with sensitized force maintenance in ileum samples (mean±S.E., n=7). C. Typical force trace showing the effect of HS38 on Ca$^{2+}$-independent force production in rabbit ileum smooth muscle. D. HS38 markedly decreased the kinetics of force development at pCa=9.0 in response to phosphatase inhibition by MC-LR (10 μM). E. Both the lag time to the onset of force (p<0.05, n=3) and the rate of force development (t$_{1/2}$) (p<0.02, n=3) were increased following the addition of MC-LR in the presence of HS38 (mean S.E., n=3).

In addition to its effect on mouse aortic SM, HS38 relaxed carbachol-induced,[35] $Ca^{2+}$-sensitized force and decreased RLC20 and MYPT1 phosphorylation in permeabilized rabbit ileum (FIG. 5A-B). HS38 induced an approximate 30% decrease in carbachol-induced force exerted by α-toxin permeabilized rabbit ileum in the presence of $Ca^{2+}$ (pCa 6.5). Western blot analysis of RLC20 and MYPT1 from these tissues showed that HS38 significantly reduced phosphorylation levels of both.

The rate of $Ca^{2+}$-independent (non-smMLCK-mediated) force production in permeabilized rabbit ileum was also affected by HS38 (FIG. 5C-E). The kinetics of force development in response to the phosphatase inhibitor, microcystin-LR (MC-LR) were significantly affected by HS38. Both lag time to the onset of force and rate of force development were increased following the addition of MC-LR in the presence of HS38.

Initial Western blot analysis failed to detect significant expression of PIM3 within rabbit ileum and mouse aortic SM tissues (data not shown), supporting the hypothesis that H38 acts through inhibition of ZIPK only.

Example 5. Effect of ROK and ZIPK Inhibition on Ca2+ Sensitization of RTA Smooth Muscle Contraction Additional experiments were completed to examine the specificity of HS-38 on the ZIPK- and ROK-dependent contractility of rat caudal arterial smooth muscle (RTA) strips in situ. Data were collected to support the lack of ROK inhibition by HS-38 in the isolated RTA strips in normal HEPES extracellular solution (NH).

Tissue preparation and Force Measurement for RTA smooth muscle: Caudal arteries were removed from male Sprague-Dawley rats (300-350 g) that had been anesthetized and euthanized according to protocols approved by the University of Calgary Animal Care and Use Committee. The arteries were cleaned of excess adventitia, de-endothelialized and cut into helical strips (1.5 mm×6 mm). Muscle strips were mounted on a Grass isometric force transducer (FT03C), and force was recorded. Intact tissues were treated with calyculin A (CLa, 10 µM). At selected sampling points, muscle strips were flash-frozen in 10% (w/v) TCA, 10 mM DTT in acetone followed by 3×10 s washes in 10 mM DTT in acetone. Tissues were then lyophilized overnight. Protein was extracted from each arterial strip by incubation (16 h, 5° C.) in 0.5 mL of SDS-PAGE sample buffer.

Western blot analysis: For the analysis of protein phosphorylation, samples of in vitro kinase assays or tissue homogenates were resolved by 10% SDS-PAGE. Proteins were transferred to 0.2 µm nitrocellulose membranes in a Tris/glycine transfer buffer containing 10% methanol. Non-specific binding sites were blocked with 5% (w/v) non-fat dry milk in TBST (25 mM Tris, 137 mM NaCl, 3 mM KCl, 0.05% Tween-20). Membranes were washed and incubated overnight (5° C.) with primary antibody at 1:1,000 dilution in 1% (w/v) non-fat dry milk in TBST. Membranes were incubated for 1 h with HRP-conjugated secondary antibody (1:10,000 dilution) in TBST and developed with SuperSignal West Femto Chemiluminescence reagent. α-actin levels were quantified to ensure equal protein loading and to normalize the signal obtained with phospho-MYPT1/LC20/Par-4 antibodies.

For analysis of $LC_{20}$ phosphorylation, samples were resolved by Phos-tag SDS-PAGE, as previously described [J Biol Chem (2012) 287, 36356-69]. Proteins were transferred to polyvinylidene difluoride membranes at 25 V for 16 h at 4° C. and fixed on the membrane with 0.5% glutaraldehyde in phosphate-buffered saline. Nonspecific binding sites were blocked with 5% (w/v) non-fat dry milk in TBST. Membranes were washed with TBST and incubated overnight with anti-$LC_{20}$ at 1:500 dilution in 1% (w/v) non-fat dry milk in TBST. Membranes were incubated for 1 h with HRP-conjugated secondary antibody (1:10,000 dilution) and developed with ECL reagent.

All Western blots were visualized with a LAS4000 Imaging Station (GE Healthcare), ensuring that the representative signal occurred in the linear range. Quantification was performed by densitometry with ImageQuant TL software (GE Healthcare).

Figure 6:
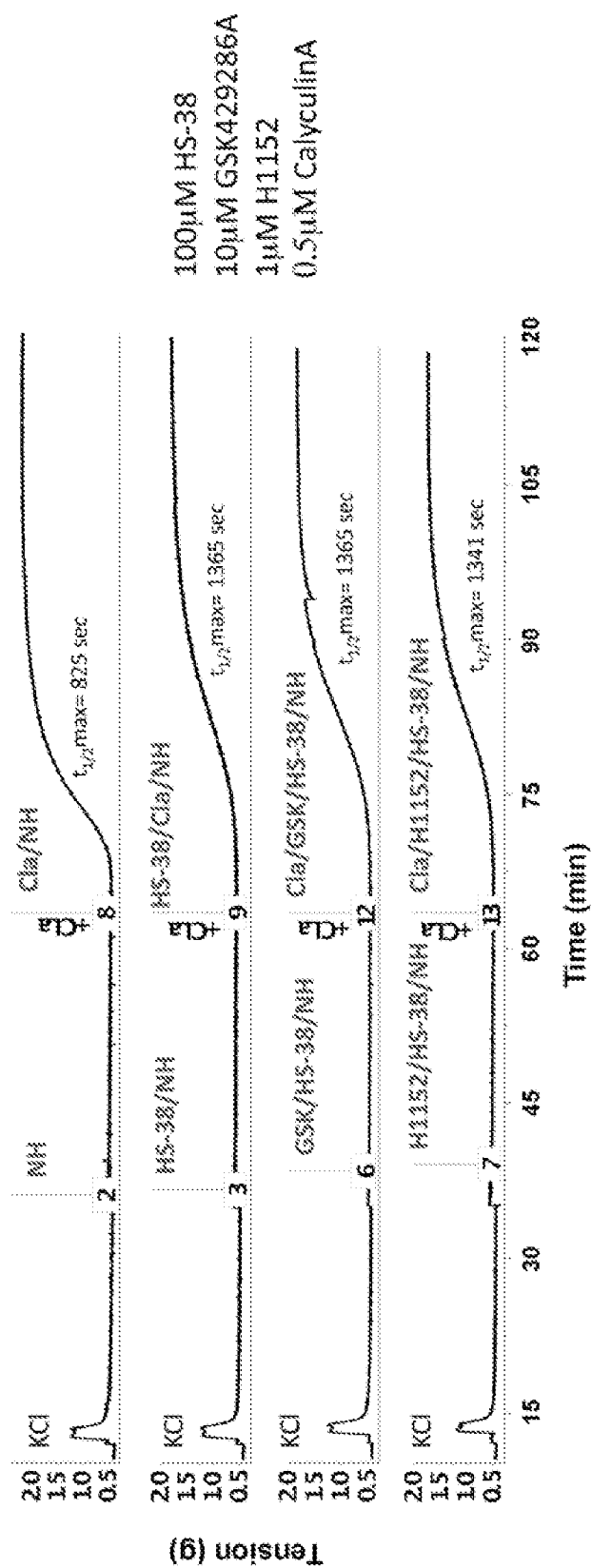
FIG. 6 shows the results of measurements to determine the effect of ROK and ZIPK inhibition on Ca2+ sensitization of RTA smooth muscle contraction. Calyculin A (CLa, 10$^{-7}$M)-induced contractions were used since inhibition of myosin phosphatase activity in RTA unmasks endogenous Ca2+-independent LC20 kinase activities, including ZIPK and ROK. Experiments were performed with addition of a ROK inhibitor (GSK-429286A, 10$^{-5}$M) in combination with HS-38. Combining ROK and ZIPK inhibitors had no additional effect on force generation during Ca2+-sensitization (maximal or t½ max).
Figure 7:
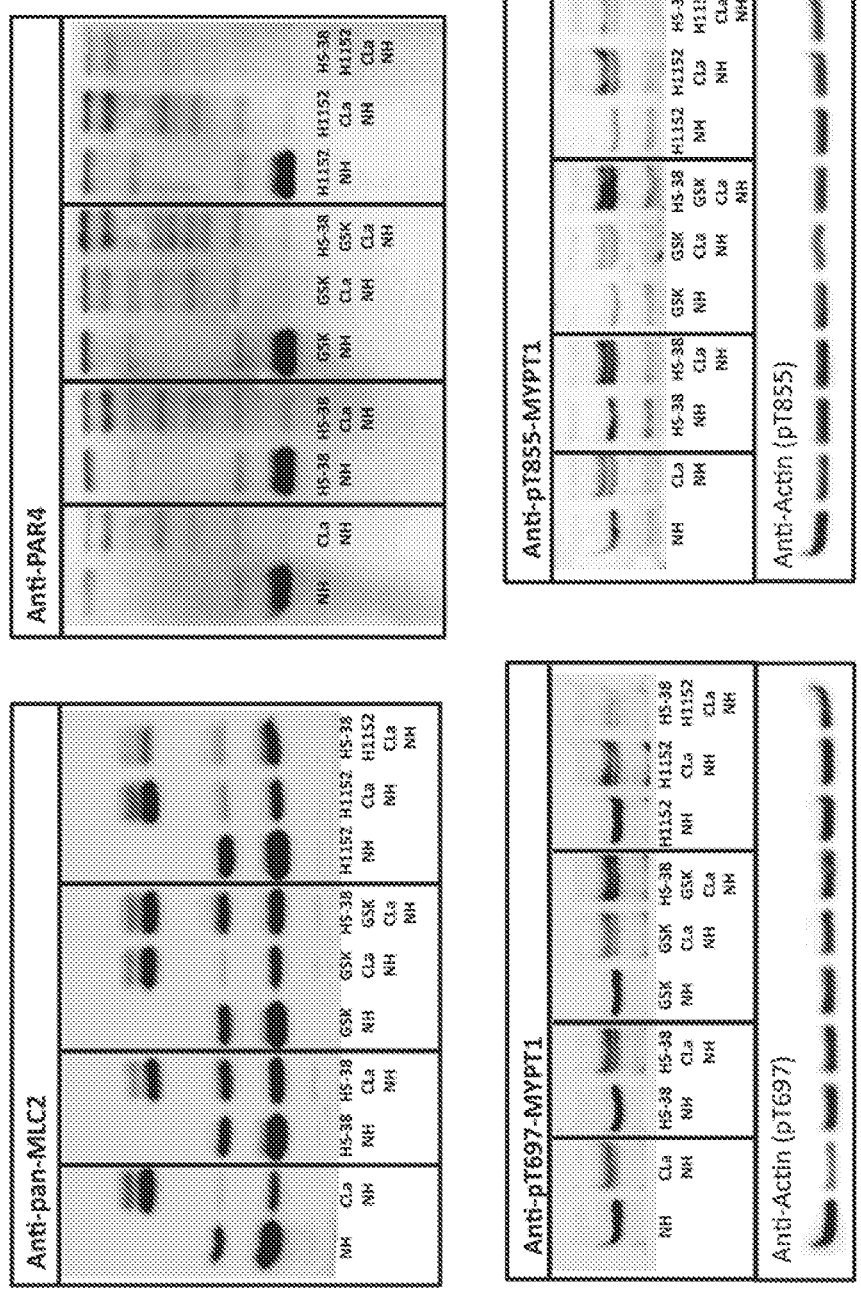
FIG. 7 shows the results of measurements to determine the effect of ROK and ZIPK inhibition on Ca2+ sensitization of RTA smooth muscle contraction. The phosphorylation of putative downstream ZIPK targets LC20 and Par-4 (Phos-Tag analyses) as well as MYPT1 (phosphospecific Abs: Thr-697 and Thr-855) was examined (n=1). In this case the phosphorylation levels of the targets were unaltered by application of HS-38 in combination with the ROK inhibitor, suggesting that HS-38 does not act via ROK

In this case, calyculin A (CLa, $10^{-7}$M)-induced contractions were used since inhibition of myosin phosphatase activity in RTA unmasks endogenous $Ca^{2+}$-independent LC20 kinase activities, including ZIPK. Experiments were performed with addition of inhibitors for ROK (HA-1152, $10^{-6}$M; GSK429286A, $10^{-5}$M) in combination with HS-38. Combining ROK and ZIPK inhibitors had no effect on $Ca^{2+}$-sensitization (force generation or downstream ZIPK target phosphorylation). These results are suggestive of a lack of off-target effects for HS-38 toward ROK in situ. See FIGS. 6 and 7.

Figure 8:
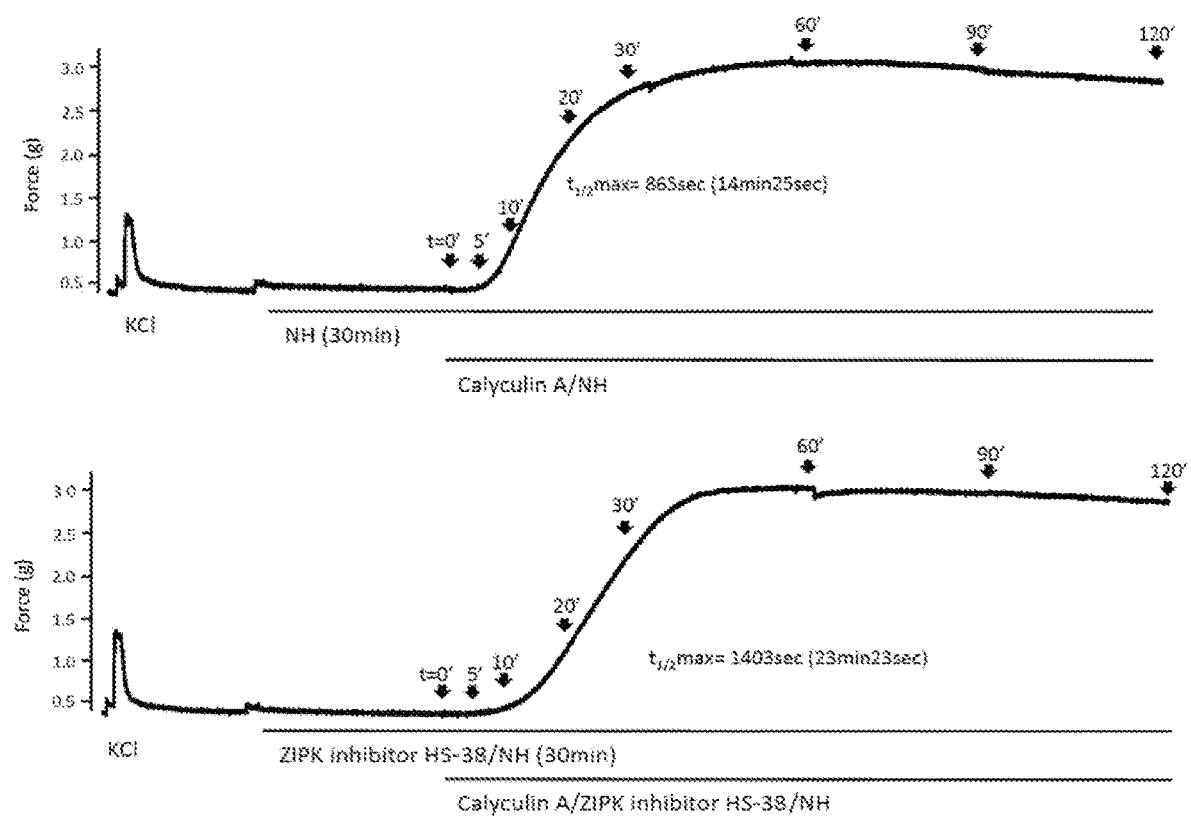
FIG. 8 shows the results of measurements to determine the effect of HS-38 on contractile force development during Ca2+ sensitization of RTA smooth muscle contraction ex vivo. Representative contractile responses of intact rat caudal arterial smooth muscle strips to calyculin A (CLa, 0.5 μM) in the presence of: vehicle control (DMSO) and HS-38 (100 μM).
Figure 9:
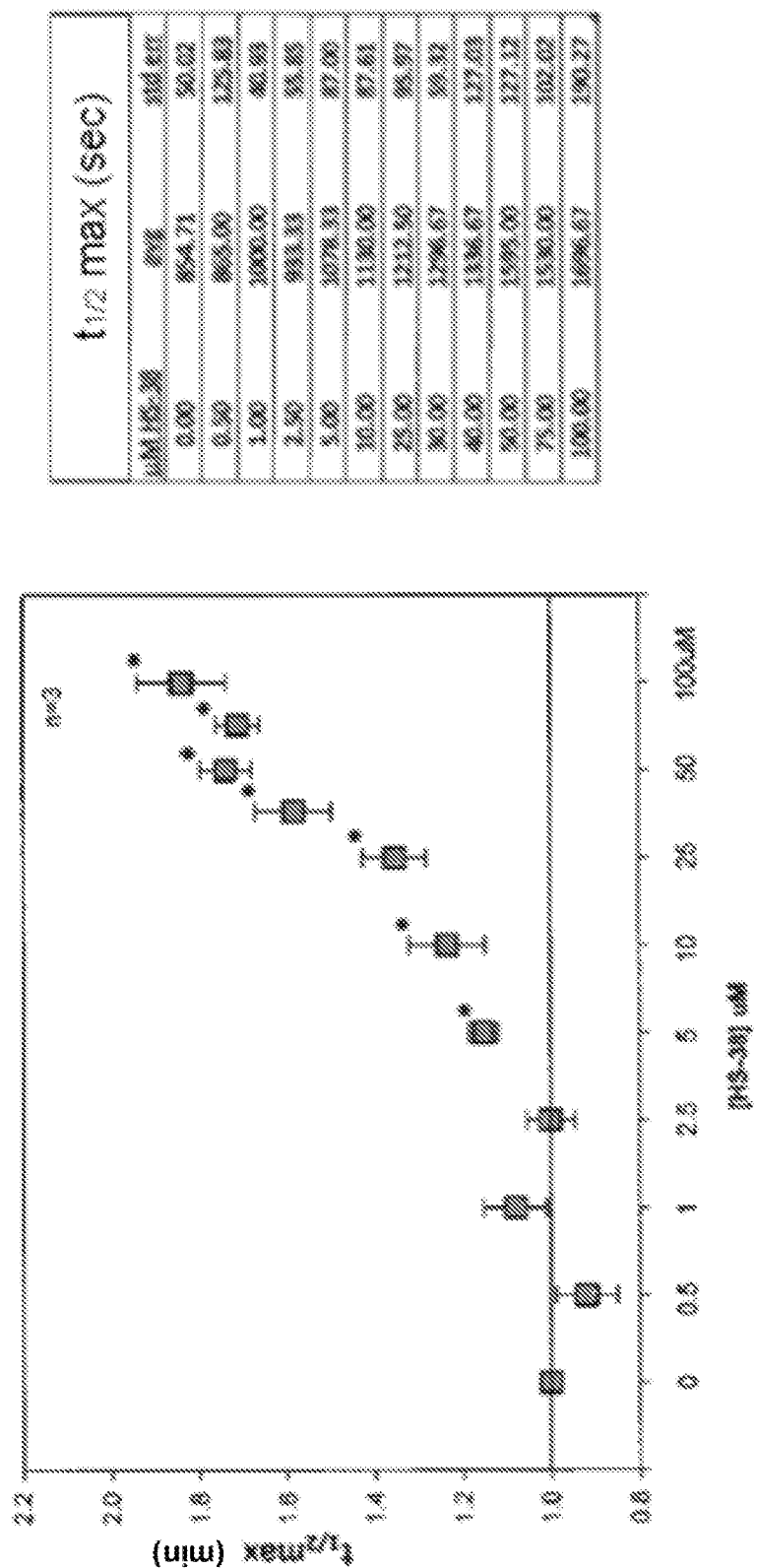
FIG. 9 shows the results of measurements to determine the effect of HS-38 on Ca2+ sensitization of RTA smooth muscle contraction ex vivo. Calyculin A (CLa, 10$^{-7}$M)-induced contractions in the presence and absence of increasing concentrations of HS-38. The data illustrate concentration-dependent increases in the contractile response of RTA (i.e., t½max; time to reach 50% of maximal contractile force) with exposure to HS-38 during the Ca2+ sensitization process.

Example 6. Effect of HS-38 on Ca2+ Sensitization of RTA Smooth Muscle Contraction Ex Vivo Data were collected for RTA smooth muscle contraction in the presence and absence of HS-38, including measurements of contractile force development and the concentration dependency of these effects. The data show HS-38 concentration-dependent attenuation of contractile force during the $Ca^{2+}$ sensitization process. The t1/2 max value is defined as the time required for contractile force to reach 50% of maximal tone. See FIGS. 8 and 9.

Figure 10:
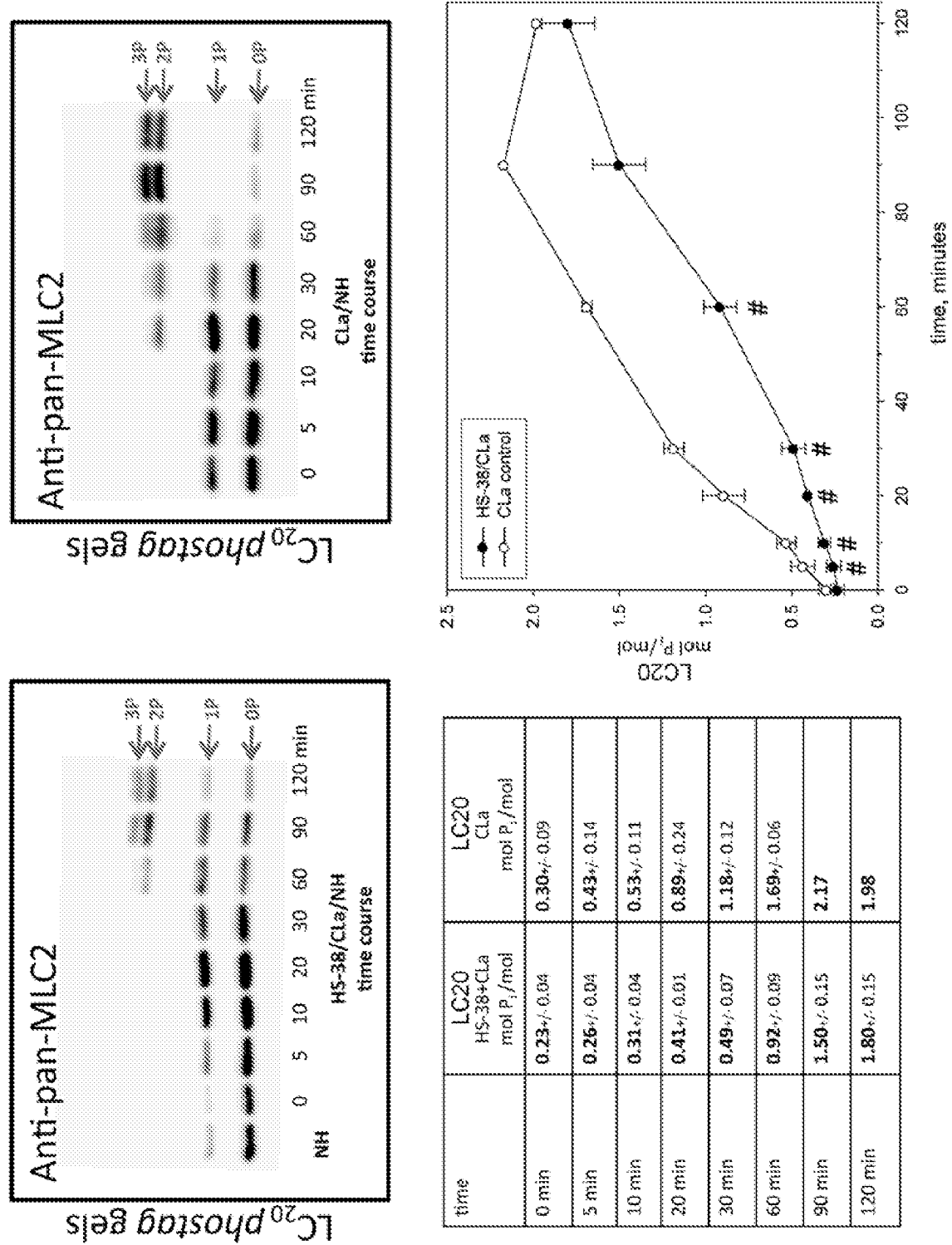
FIG. 10 shows the results of experiments to determine the effect of HS-38 on LC20 phosphorylation during Ca2+ sensitization of RTA smooth muscle contraction. Calyculin A (CLa, 10$^7$M)-induced contractions in the presence and absence of HS-38 (50 μM), including measurements of LC20 (anti-panMLC2 antibody) mono- and diphosphorylation by PhosTag gel analysis as well as the time-dependency of these effects. The data illustrate time-dependent attenuations of LC20 phosphorylation by HS-38 during the Ca2+ sensitization process.
Figure 11:
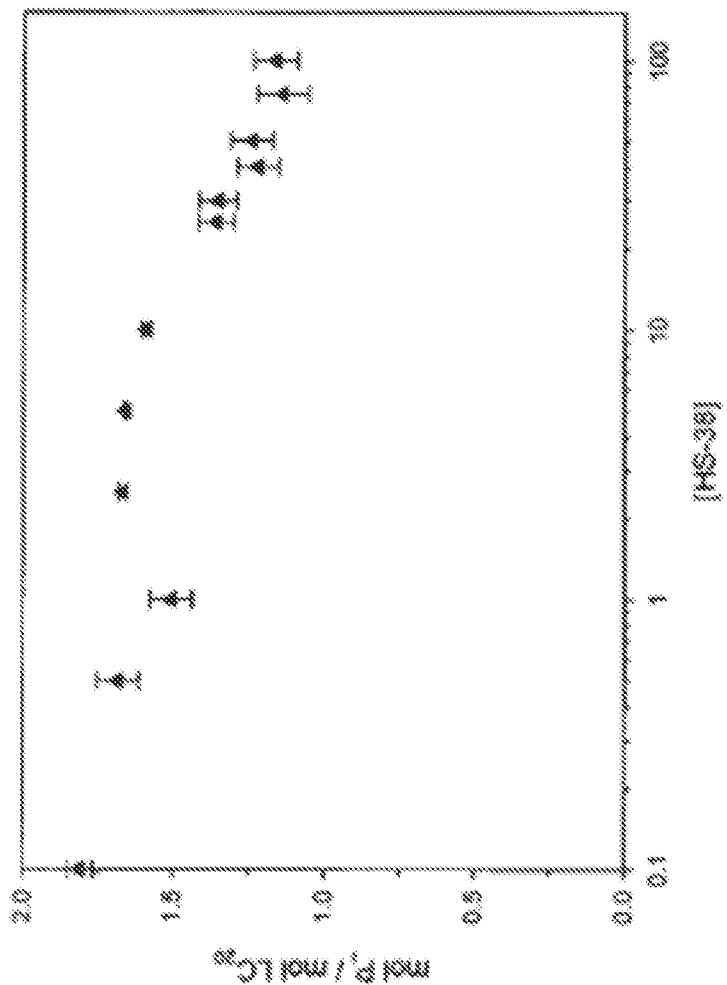
FIG. 11 shows the results of experiments to determine the concentration-dependent effect of HS-38 on LC20 phosphorylation during Ca2+ sensitization of RTA smooth muscle contraction. Tissue lysates from calyculin A (CLa, $10^{-7}$M)-induced contractions in the presence and absence of HS-38 (50 µM) were analyzed for LC20 (anti-panMLC2 antibody) mono- and diphosphorylation by PhosTag gels. The data illustrate time-dependent attenuations of LC20 phosphorylation by HS-38 during the Ca2+ sensitization process.

Example 7. Effect of HS-38 on LC20 Phosphorylation During Ca2+ Sensitization of RTA Smooth Muscle Contraction The RTA was used as a model vessel to collect a wealth of evidence to support a mechanistic role for ZIPK in $Ca^{2+}$ sensitizing mechanisms for the regulation of VSM contractile tone. Data were collected from calyculin A (CLa, $10^{-7}M$)-induced contractions in the presence and absence of HS-38 (50 uM), including measurements of LC20 mono- and diphosphorylation as well as the time- and concentration-dependency of these effects. See FIGS. 10 and 11.

LC20 phosphorylation is provided as a stoichiometric value—i.e. the # of moles of phosphate incorporated into each mole of LC20 protein. mol Pi/mol LC20=(y+2z+3q)/(x+y+z+q), where x, y, z and q are the signals of unphosphorylated and mono-, di-, and triphosphorylated LC20 bands, respectively.

Figure 12:
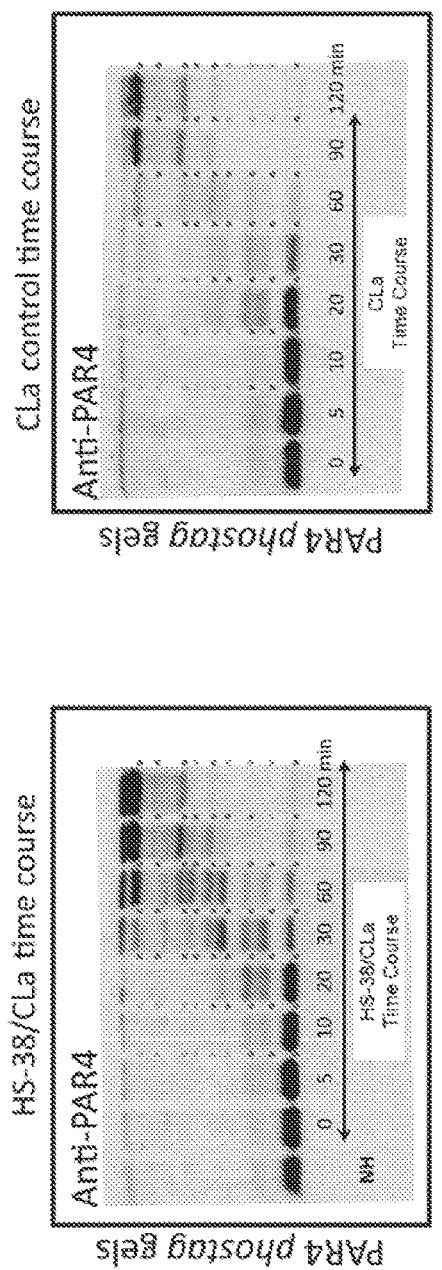
FIG. 12 shows the results of experiments to determine the effect of HS-38 on prostate-apoptosis response (Par)-4 protein phosphorylation during $Ca^{2+}$ sensitization of RTA smooth muscle contraction. Calyculin A (CLa, $10^{-7}$M)-induced contractions of isolated RTA smooth muscle in the presence and absence of HS-38 (50 µM), including measurements of LC20 mono- and diphosphorylation as well as the time-dependency of these effects. ZIPK effects on contractile force during Ca2+ sensitization do not appear to act through Par-4 in RTA.
Figure 12:
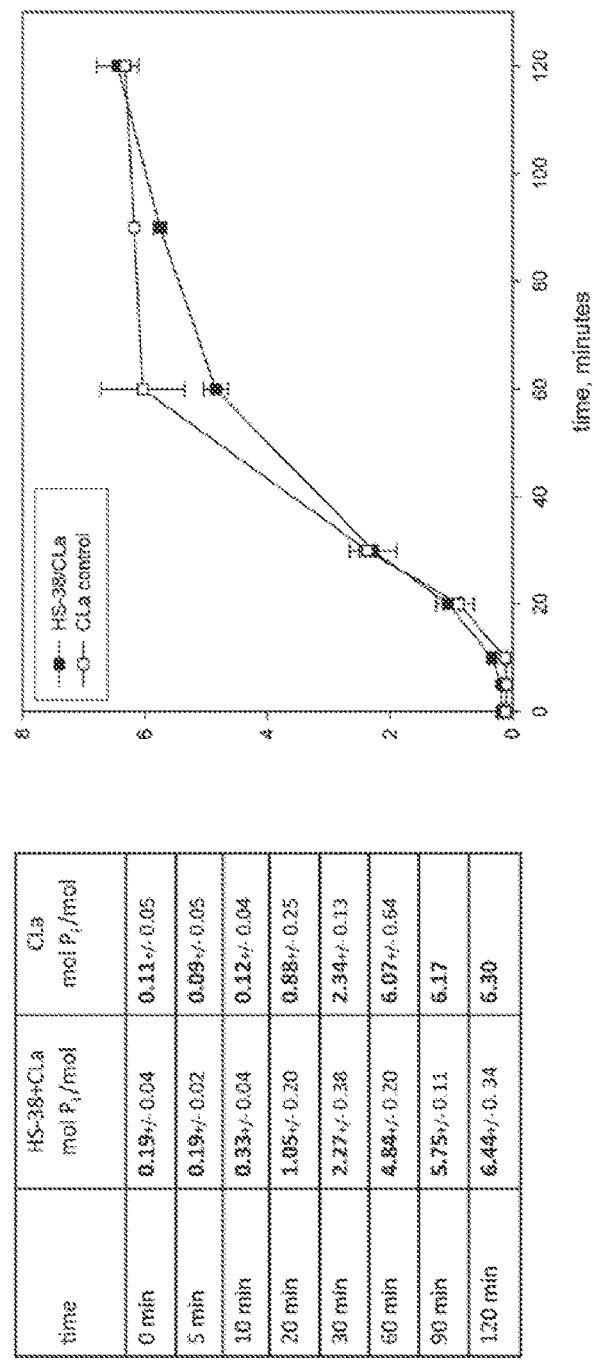

Example 8. Effect of HS-38 on Prostate-Apoptosis Response (Par)-4 Protein Phosphorylation During $Ca^{2+}$ Sensitization of RTA Smooth Muscle Contraction Data were collected from calyculin A (CLa, $10^{-7}M$)-induced contractions of RTA smooth muscle in the presence and absence of HS-38 (50 uM), including measurements of LC20 mono- and diphosphorylation as well as the time-dependency of these effects. ZIPK effects on contractile force during $Ca^{2+}$ sensitization do not act through Par-4 in RTA smooth muscle. See FIG. 12.

For analysis of Par-4 phosphorylation, samples were resolved by Phos-tag SDS-PAGE. Conditions were modified from those previously described [J Biol Chem (2012) 287, 36356-69] to ensure separation of Par-4 proteins. Proteins were transferred to polyvinylidene difluoride membranes at 25 V for 16 h at 4° C. and fixed on the membrane with 0.5% glutaraldehyde in phosphate-buffered saline. Nonspecific binding sites were blocked with 5% (w/v) non-fat dry milk in TBST. Membranes were washed with TBST and incubated overnight with anti-Par-4 at 1:1000 dilution in 1% (w/v) non-fat dry milk in TBST. Membranes were incubated for 1 h with HRP-conjugated secondary antibody (1:10,000 dilution) and developed with ECL reagent.

The Par-4 phosphorylation is provided as a stoichiometric value—i.e, the # of moles of phosphate incorporated into each mole of Par-4 protein.

Figure 13:
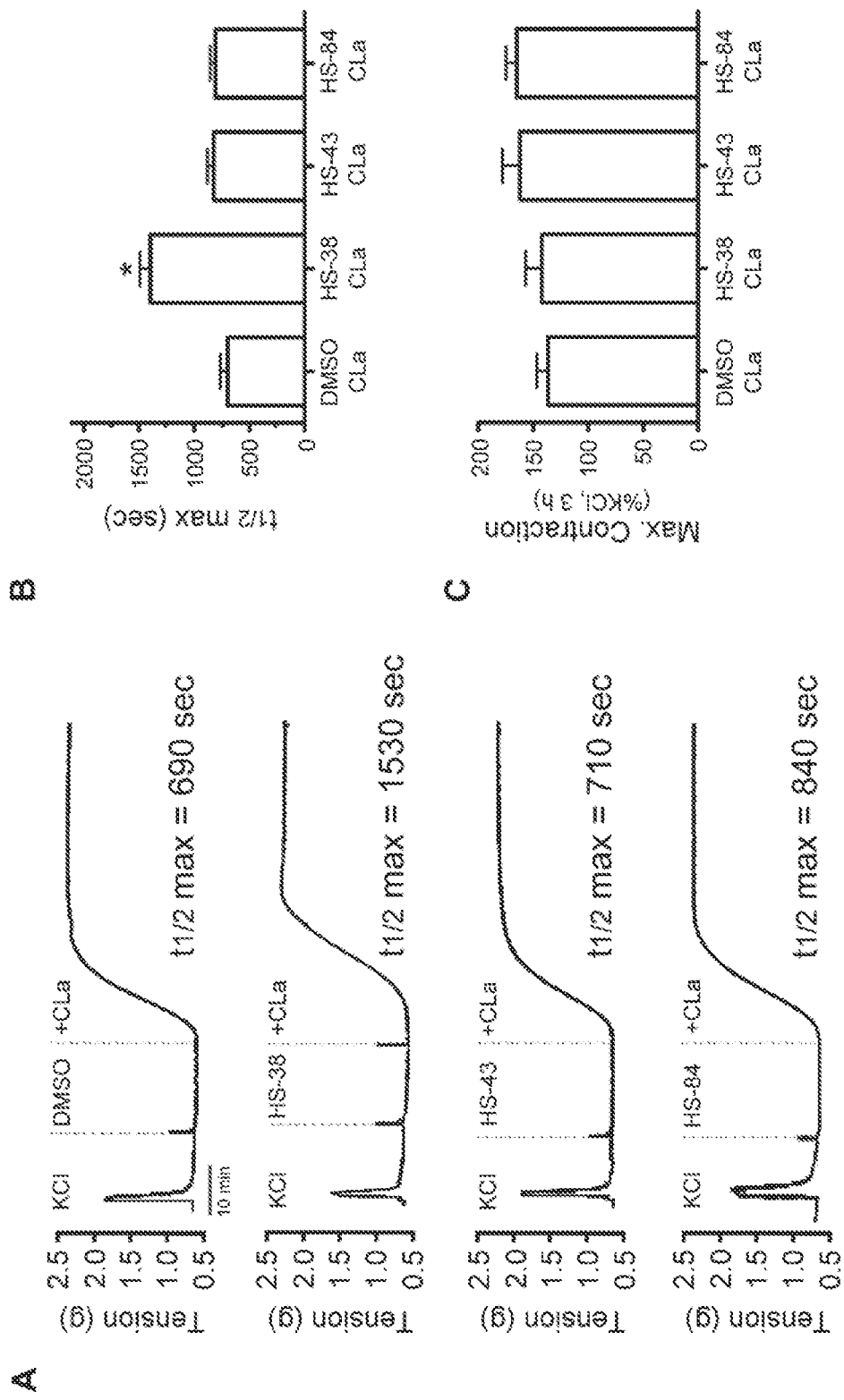
FIG. 13 shows the results of experiments to determine the effect of HS-43 and HS-84 on Ca2+ sensitization of RTA smooth muscle contraction. A, representative contractile responses of intact rat caudal arterial smooth muscle strips to calyculin A (CLa, 0.5 µM) in the presence of: vehicle control (DMSO), HS-38 (100 µM), HS-43 (100 µM) or HS-84 (100 µM). B, the time (sec) required to reach 500% of maximal contraction after application of CLa was calculated. C, the maximal contractile force developed with CLa exposure (0.5 µM, 3 h) was expressed as a % of an initial reference contraction to KCl. *—significantly different from CLa (DMSO) treatment (ANOVA with Dunnett's post hoc test, $p<0.05$, n=5).
Figure 14:
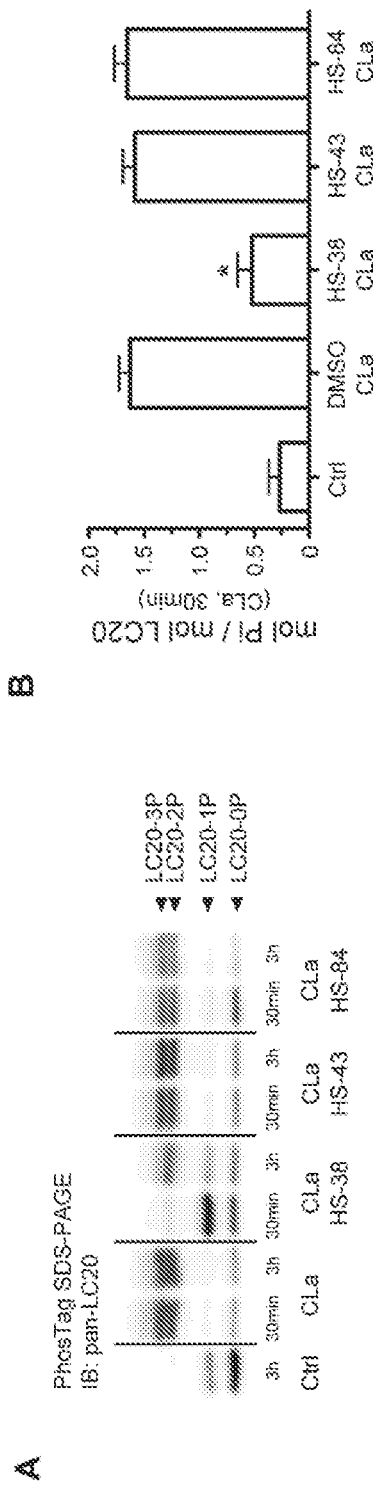
FIG. 14 shows the results of experiments to determine the effect of HS-43 and HS-84 on the phosphorylation of LC20 during Ca2+ sensitization of RTA smooth muscle contraction. A, LC20 phosphorylation was analysed by Phos-tag SDS-PAGE with detection of unphosphorylated, mono (1P)-, di (2P)- and tri (3P)-phosphorylated forms by western blotting with anti-panLC20. B, The LC20 bands were quantified by scanning densitometry, and the data are expressed as phosphorylation stoichiometry (mol Pi/mol LC20; 30 min CLa exposure). *—significantly different from CLa (DMSO) treatment (ANOVA with Dunnett's post hoc test, $p<0.05$, n=5).

Example 9. Effect of HS-43 and HS-84 on Ca2+ Sensitization of RTA Smooth Muscle Contraction The effects of additional compounds HS-84 & HS-43, which display potent Pimk inhibition without activity toward ZIPK) were also assessed with RTA smooth muscle. In this case, the HS-84 and HS-43 compounds confirm that there were no contributions of Pimk1/3 to the contractile processes. See FIGS. 13 and 14.

Figure 15:
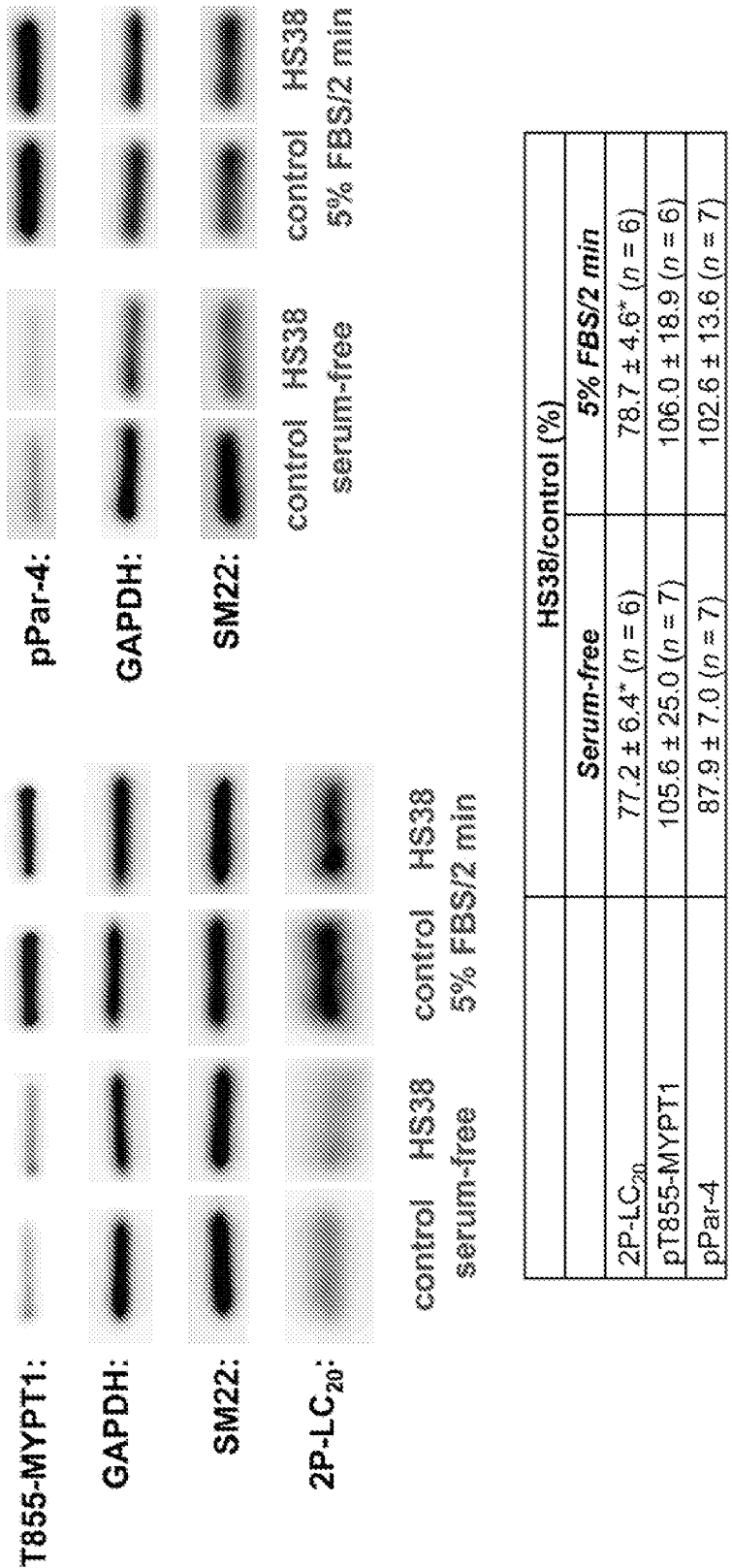
FIG. 15 shows the results of experiments to determine the effect of HS-38 on protein phosphorylation in human coronary artery smooth muscle cells (hCA-VSMC, Lonza Inc #CC-2583; passage 12). Cells were serum-starved overnight, incubated for 40 min with HS-38 (10 µM) or vehicle and treated (or not) with 5% FBS for 2 min prior to lysis in SDS-gel sample buffer for SDS-PAGE and western blotting with anti-diphospho(T8/S19)-LC20, anti-phosphoT855-MYPT1 or anti-phosphoT155-Par-4. Phosphorylated bands were quantified by scanning densitometry and normalized to the loading control (SM22). Phosphorylation levels in the presence of HS-38 are expressed as a percentage of control (absence of ZIPK inhibitor). Values represent means±S.E.M. (n values are indicated in parentheses).

Example 10. Effect of ZIPK Inhibitor HS-38 on Protein Phosphorylation in Human Coronary Artery Smooth Muscle Cells Human coronary artery smooth muscle cells (hCA-VSMC) were serum-starved overnight, incubated for 40 min with HS-38 (10 µM) or vehicle and treated (or not) with 5% fetal bovine serum (FBS) for 2 min prior to lysis in SDS-gel sample buffer for SDS-PAGE and western blotting with anti-2P-$LC_{20}$, anti-pT855-MYPT1 or anti-pPar-4. Phosphorylated bands were quantified by scanning densitometry and normalized to the loading control (SM22 or GAPDH). Phosphorylation levels in the presence of HS-38 are expressed as a percentage of control (absence of ZIPK inhibitor). Values represent means S.E.M. (n values are indicated in parentheses). See FIG. 15. The hCA-VSMC (#CC-2583) cells were from Lonza Inc. Cells were grown to passage 1.

Conclusions:

(i) FBS treatment for 2 min induced significant phosphorylation of MYPT1 at T855, Par-4 at T155 and LC20 at T18 and S19; (ii) ZIPK inhibition with HS-38 had no significant effect on MYPT1-T855 phosphorylation or Par-4-T155 phosphorylation in serum-free medium or after 2-min treatment with 5% FBS; (iii) ZIPK inhibition causes a significant reduction in $LC_{20}$ diphosphorylation under serum-free conditions and after 2-min treatment with 5% FBS ($*p<0.01$).

Figure 16:
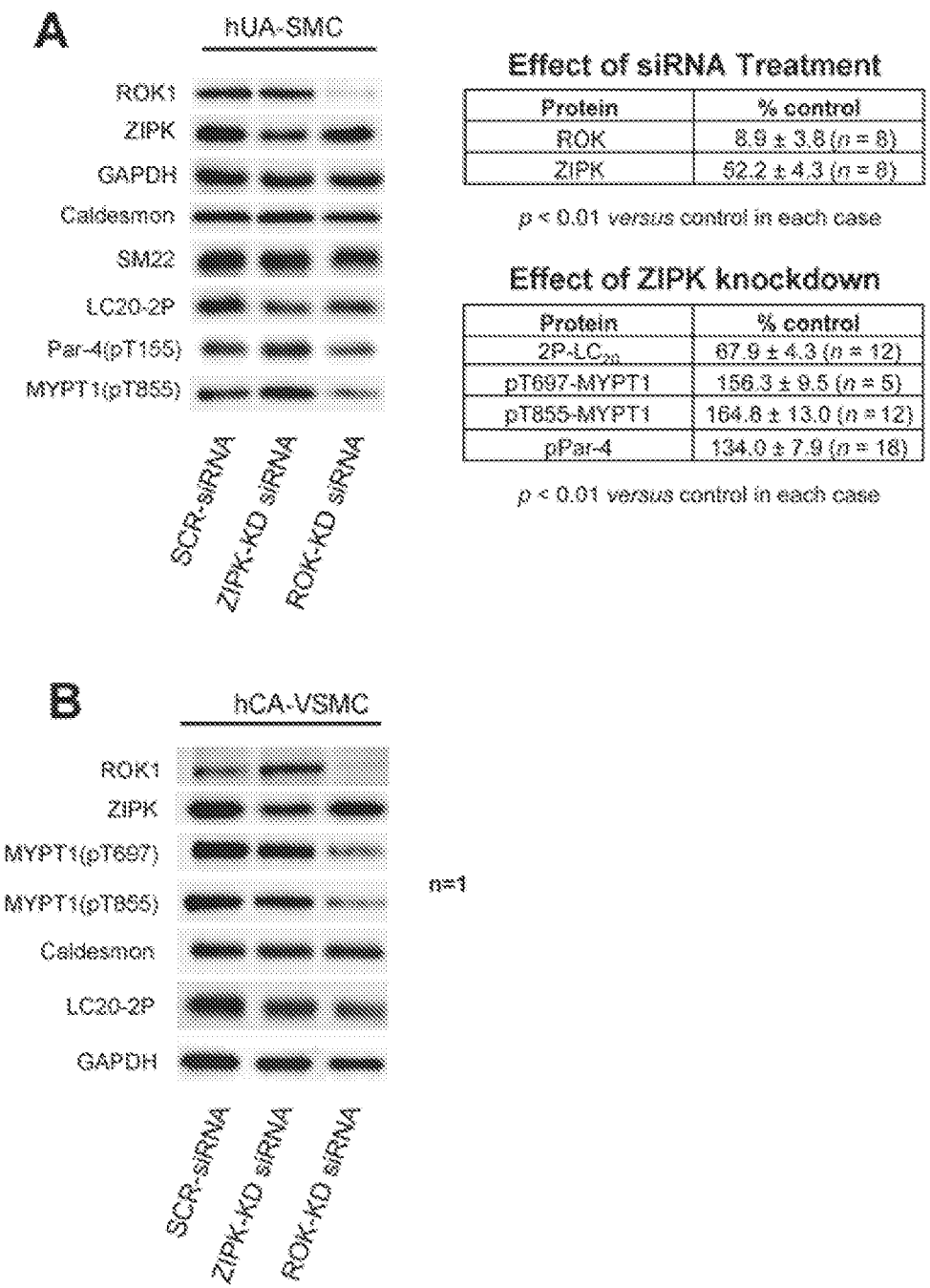
FIG. 16 shows the results of ROK and ZIPK siRNA knockdown experiments in human umbilical artery (hUA-VSMC) and human coronary artery cells (hCA-VSMC) and the effects on various protein phosphorylations. The (A) hUA-VSMC (#CC-2579) and (B) hCA-VSMC (#CC-2583) cells were from Lonza Inc. Cells were grown to passage 12, and various smooth muscle parker proteins are still expressed (e.g., caldesmon and SM22). ZIPK and ROK proteins were downregulated by siRNA treatment (ZIPK-KD and ROK-KD). Controls were treated identically, but with scrambled siRNA. Cells were grown in the presence of 1% FBS and lysed for SDS-PAGE and western blotting. ZIPK protein downregulation resulted in reduced LC20 diphosphorylation at Ser19 and Thr18 (LC20-2P) and increased phosphorylation of MYPT1 (Thr697 & Thr855), and of Par-4 (Thr155). GAPDH was used as a loading control. For the hUA-VSMCs, values indicate means±S.E.M. of n independent experiments. For the hCA-VSMCs, values are representative of a single experiment.

Example 11. ROK and ZIPK siRNA Knockdown Experiments in Human Umbilical Artery (hUA-VSMC) and Human Coronary Artery Cells (hCA-VSMC) and the Effects on Various Protein Phosphorylations hUA-VSMC (#CC-2579) and hCA-VSMC (#CC-2583) cells were from Lonza Inc. Cells were grown to passage 12, and various smooth muscle parker proteins are still expressed (e.g., caldesmon and SM22). ZIPK and ROK proteins were down-regulated by siRNA treatment (ZIPK-KD and ROK-KD). Controls were treated identically, but with scrambled siRNA. Cells were grown in the presence of 1% FBS and lysed for SDS-PAGE and western blotting. ZIPK downregulation resulted in reduced $LC_{20}$ diphosphorylation at Ser19 and Thr18 (LC20-2P) and increased phosphorylation of MYPT1 (Thr697 & Thr855), and of Par-4 (Thr155). GAPDH was used as a loading control. Results are shown in FIG. 16. For the hUA-VSMCs (see FIG. 16A), values indicate means S.E.M. of n independent experiments. For the hCA-VSMCs (see FIG. 16B), values are representative of a single experiment.

Example 12. HS-38 can Suppress Intrinsic Myogenic Tone Development in Posterior Cerebral Arteries from Sprague Dawley Rats Posterior cerebral arteries (PCAs) from male Sprague-Dawley rats were isolated and mounted/cannulated for pressure myography. Briefly, 2-3 mm arterial segments are mounted across glass canuli in an arteriograph chamber attached to a pressure myograph (Living Systems, Burlington, Vt., USA) and tied in place using silk suture. Endothelial cells are removed by passing a stream of air bubbles through the vessel lumen (this methodology was confirmed by loss of dilatory response to acetylcholine). Mounted arteries are pressurized to low luminal pressure (20 mmHg) and warmed to 37° C. by circulating heated, aerated Krebs, through the bath at a rate of 2-3 ml/min. After a 30 min equilibration time, luminal pressure is increased to 80 mmHg and to allow tone to develop over 20 minutes. All vessels are then subjected to two additional 5 min pressure steps down to 10 mmHg and back to 80 mmHg to ensure stable pressure-dependent myogenic constriction. Vessels that exhibit cannuli blockage (as determined by no change in diameter in response to pressure changes) or leaks (as determined by inability to stably maintain pressure) are discarded. After this, arteriole myogenic responses (i.e., vessel diameter) to increasing luminal pressure were monitored ex vivo in the absence or presence of HS-38. Vessels are subjected to pressure steps from 10-120 mmHg, allowing a stable diameter to be reached after each step (~5 min). This series of steps is repeated in normal Krebs buffer, with the addition of ZIPK inhibitor (i.e., 10 μM HS-38) and finally in $Ca^{2+}$ free Krebs (same constitution as normal Krebs with no $CaCl_2$ and added EGTA (2 mM). Data are collected as average vessel diameter over stable region of each step and expressed as a percentage of the maximal passive vessel diameter (120 mmHg, $0Ca^{2+}$) to standardize for variation in size of $3^{rd}$ order mesenteries.

Figure 17:
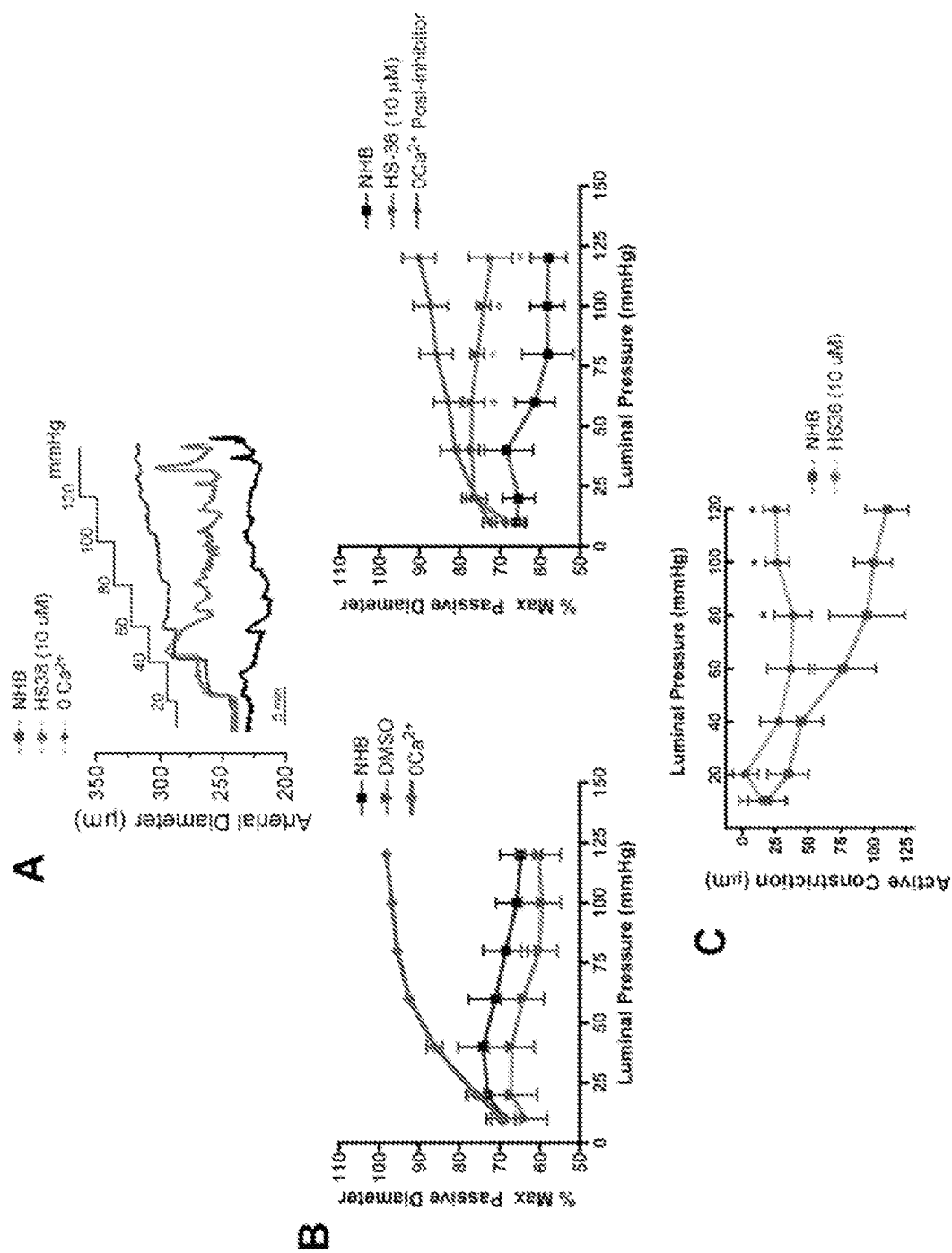
FIG. 17 shows the results of experiments to determine the effect of HS-38 on intrinsic myogenic tone development in posterior cerebral arteries from Sprague Dawley rats. Posterior cerebral arteries (PCAs) were subjected to increasing pressure steps (10-120 mmHg) in normal Krebs' saline solution (NHB) and zero extracellular Ca2+ saline (0 Ca2+) as well as active constriction-pressure relationships in the presence of HS-38 (10 µM) or vehicle control (DMSO). Data are means (n=5 animals) for size-matched vessels from 10-wk, male Sprague-Dawley rats. The average maximum passive diameters at 120 mmHg were 329±18.7 µm. Representative pressure-induced changes in arteriole diameter (A) as well as mean diameter-pressure relationships (B) and active myogenic constriction (C) are shown.

Results are shown in FIG. 17. Pressure-induced changes in mean arterial diameter are shown for 10-120 mmHg in normal Krebs' saline solution (NHB, black) and zero extracellular $Ca^{2+}$ saline (0 $Ca^{2+}$, blue) as well as active constriction-pressure relationships in the presence of HS-38 (10 uM or vehicle DMSO control, red). The $Ca^{2+}$ saline condition is associated with a loss of myogenic control of arterial diameter and forced dilation of the vessel. Inhibition of ZIPK activity with HS-38 was observed to influence myogenic tone development across the pressure range 25-120 mmHg.

Figure 18:
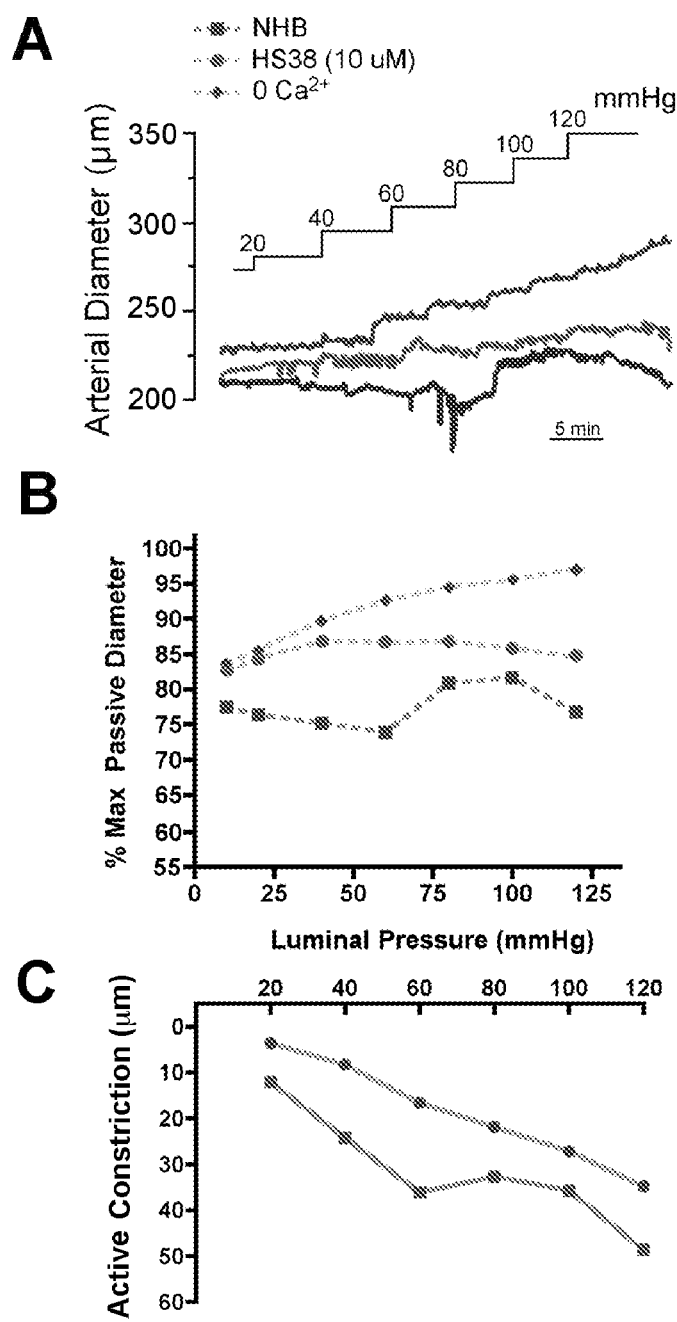
FIG. 18 shows the results of experiments to determine the effect of HS-38 on enhanced myogenic tone associated with hypertension in the spontaneous hypertensive rat (SHR) model. Posterior cerebral arteries (PCAs) were subjected to increasing pressure steps (10-120 mmHg) in normal Krebs' saline solution (NHB) and zero extracellular Ca2+ saline (0 Ca2+) as well as active constriction-pressure relationships in the presence of HS-38 (10 µM). Data are means (n=2 animals) for size-matched vessels from 10-wk SHR rats. The average maximum passive diameters at 120 mmHg were 280 µm. Representative pressure-induced changes in arteriolar diameter (A) as well as mean diameter-pressure relationships (B) and active myogenic constriction (C) are shown.
Figure 19:
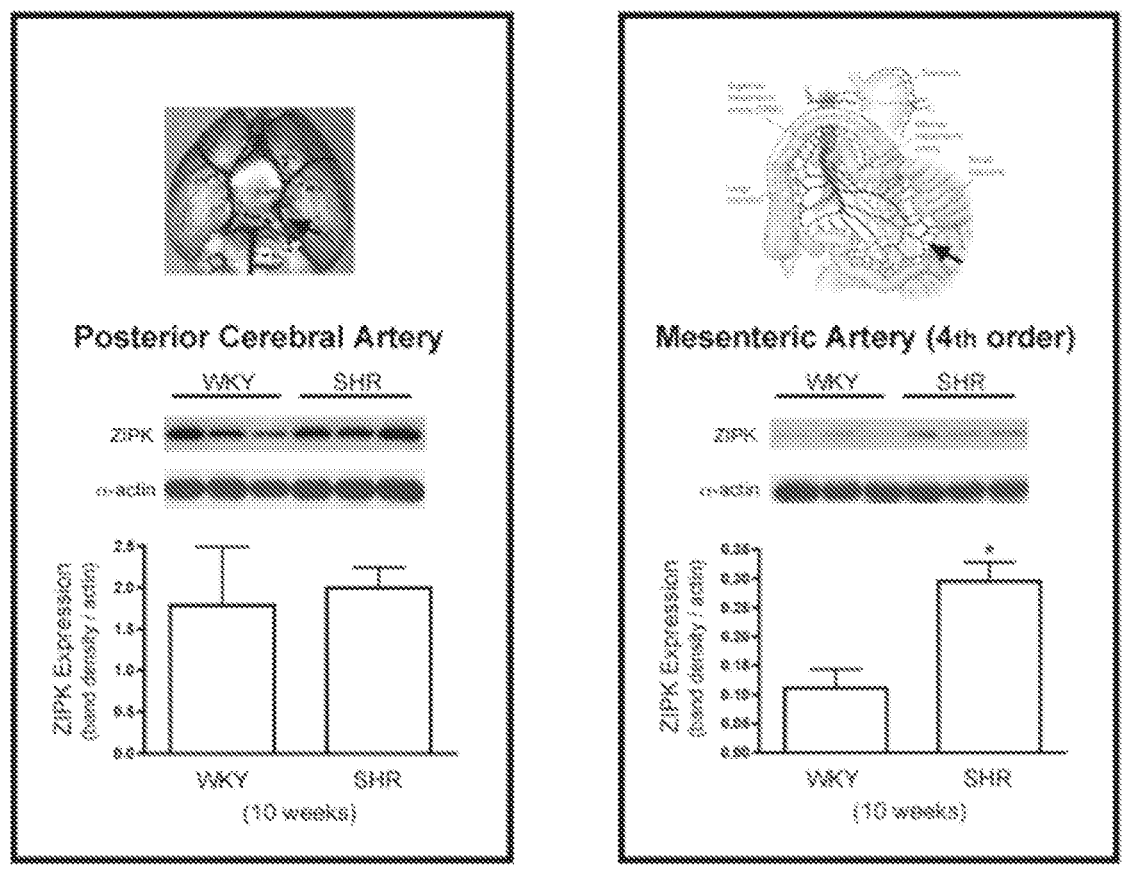
FIG. 19 shows the results of experiments to determine the expression levels of ZIPK in resistance vessels collected from posterior cerebral and 4th order mesenteric arteries of the spontaneous hypertensive rat (SHR) model. Posterior cerebral arteries (PCAs) and mesenteric arteries (4th order) were collected from 10-wk SHR or Wistar-Kyoto (strain control) animals for biochemical analysis. Immunoreactive bands were quantified with a LAS4000 gel analyzer, and densitometry was normalized to the loading control (SMC α-actin). Data are means S.E.M. (n=3 animals). Samples were all run on a single SDS-PAGE gel for quantitative analysis.

Example 13. HS-38 can Suppress the Enhanced Myogenic Tone Associated with Hypertension in the Spontaneous Hypertensive Rat (SHR) Model The spontaneously hypertensive (SHR) and normotensive Wistar Kyoto (WKY) rat at the early stage of hypertension (10-wks) were employed to determine the specific changes in ZIPK signaling that lead to dysfunctional VSM tone. Ex vivo studies of isolated $4^{th}$-order posterior cerebral arteries (PCAs, endothelium denuded) suggest a significant contribution of ZIPK to the enhanced myogenic tone that is observed in these vessels early in the development of hypertension. Enhanced myogenic tone at low basal luminal pressures can be attenuated with application of the HS-38 compound. Modulation of ZIPK activity may be a prime determinant for development of hypertension, and recent studies provide evidence for up-regulation of ZIPK in this model of primary (essential) hypertension. See FIG. 18. Pressure-induced changes in arterial diameter (mean+/−S.D., n=2) are shown for 10-120 mmHg in normal Krebs' saline solution (NHB, blue) and zero extracellular $Ca^{2+}$ saline (0 $Ca^{2+}$, green) as well as active constriction-pressure relationships in the presence of HS-38 (10 uM, red). The $Ca^{2+}$ saline condition is associated with a loss of myogenic control of arterial diameter and forced dilation of the vessel. Posterior cerebral arteries (PCAs) and mesenteric arteries ($4^{th}$ order) were also collected from 10-wk SHR and WKY rats for biochemical analysis. Immunoreactive bands were quantified with a LAS4000 gel analyzer, and densitometry was normalized to the loading control (SMC α-actin). Data are means±S.E.M. (vessels from n=3 animals). See FIG. 19. *—Significantly different from WKY, p<0.05 by Student's t-test.

Example 14. HS-38 can Suppress Myogenic Tone Development in Isolated Human Cerebral Arterioles A human cerebral artery (CA) was harvested during a tumor removal. Cerebral tissue was obtained from a 55 year woman with metastatic adenocarcinoma from lung. Surface vessels of the anterior cerebral artery off the midline over the left anterior frontal lobe were dissected for analysis. Consent for studies on human tissue was obtained as per a human ethics review protocol accepted by the Conjoint Health Research Ethics Board (CHREB) of the University of Calgary and Alberta Health Services.

Figure 20:
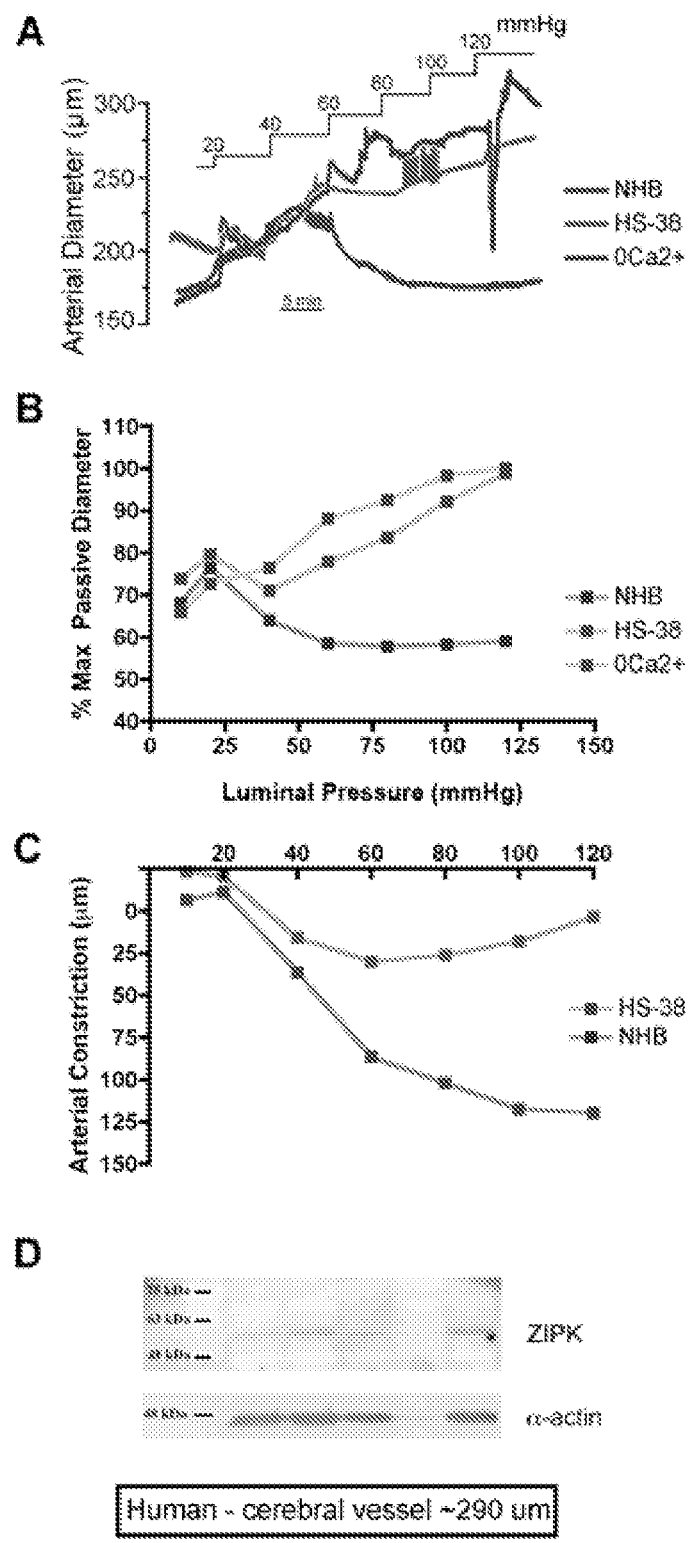
FIG. 20 shows the results of experiments to determine the effect of HS-38 on myogenic tone development in isolated human cerebral arterioles. A human cerebral artery (CA) was harvested during a tumour removal. Cerebral tissue was obtained from a 55 yr woman with metastatic adenocarcinoma from lung. Surface vessels of the anterior cerebral artery off the midline over the left anterior frontal lobe were dissected for analysis. A vessel was subjected to increasing pressure steps (10-120 mmHg) in normal Krebs' saline solution (NHB) and zero extracellular Ca2+ saline (0 Ca2+) as well as active constriction-pressure relationships in the presence of HS-38 (10 µM). Pressure-induced changes in arteriolar diameter (A) as well as diameter-pressure relationships (B) and arterial constriction (C) are shown. Data are from n=1 vessel. The passive diameter at 120 mmHg was ~290 µm. Vessels of similar diameter were isolated, proteins were extracted with SDS-PAGE buffer and immunoblotted (D) for ZIPK and α-actin as a loading control.

See FIG. 20. A vessel was subjected to increasing pressure steps (10-120 mmHg) in normal Krebs' saline solution (NHB, blue) and zero extracellular $Ca^{2+}$ saline (0 $Ca^{2+}$, green) as well as active constriction-pressure relationships in the presence of HS-38 (10 μM, red). Pressure-induced changes in arteriole diameter (A) as well as diameter-pressure relationships (B) and arterial constriction (C) are shown. Data are from n=1 vessel. The passive diameter at 120 mmHg was ~300 μm. Vessels of similar diameter were isolated, proteins were extracted and immuno-blotted (D) for ZIPK and α-actin as a loading control. Bands were quantified with a LAS4000 gel analyzer.

The $Ca^{2+}$ saline condition is associated with a loss of myogenic control of arterial diameter and forced dilation of the vessel. Inhibition of ZIPK activity with HS-38 appeared to attenuate myogenic tone development in the ex vivo human vessel. Our preliminary data supports a role for ZIPK in the molecular mechanism of myogenic tone regulation in human vessels. The role of $Ca^{2+}$-sensitization mechanisms in regulation of cerebral vascular resistance/caliber and myogenic tone in general suggest that this regulatory process is at least as, if not more important than $Ca^{2+}$-dependent mechanisms which might explain the lack of clinical efficacy for $Ca^{2+}$-channel blockers in treatment of vasospasm. HS-38 may be useful for cerebral vasospasm post-subarachnoid hemorrhage (SAH) and in Call-Fleming/reversible cerebral vasoconstriction syndrome (RCVS).

Example 15. HS-38 Attenuates Contractile Force Development of Isolated Rat Ileal Smooth Muscle Small intestine (ileum) was removed from male Sprague-Dawley rats anesthetized and euthanized according to protocols approved by the University of Calgary Animal Care and Use Committee. Ileal smooth muscle sheets were dissected and cut into longitudinal smooth muscle strips (250 μm×2 mm). For force measurement, muscle strips were tied with silk monofilaments to the tips of two fine wires. One wire was fixed, and the other was connected to a force transducer (SensoNor, AE801). The strip was mounted in a well on a stir plate to allow rapid solution exchange. Strips were stretched in the longitudinal axis to 1.3×resting length and equilibrated for 30 min in normal extracellular solution (NES) containing: 150 mM NaCl, 4 mM KCl, 2 mM calcium methanesulfonate ($CaMS_2$), 1 mM magnesium methanesulfonate ($MgMS_2$), 5.5 mM glucose, and 5 mM 4-(2-hydroxyethyl)-1-piperazine-ethanesulfonic acid (HEPES) pH 7.3. After obtaining a good contractile response with high [$K^+$] extracellular solution (KES; replacement of NaCl in NES solution with equimolar potassium methanesulfonate (KMS)), muscle strips were returned to NES and Ca2+-sensitization of muscle contraction was stimulated with application of a protein phosphatase inhibitor calyculin A (CLa, $10^{-7}$M). In this case, CLa-induced contractions were used since inhibition of myosin phosphatase activity in unmasks endogenous $Ca^{2+}$-independent LC20 kinase activities, including ZIPK. The force levels obtained with NES and an initial exposure to 10 μM carbachol (CCh, acetylcholine mimetic to set a reference constriction) were designated as 0% and 100%, respectively. All contractile measurements were carried out at room temperature (23° C.).

Figure 21:
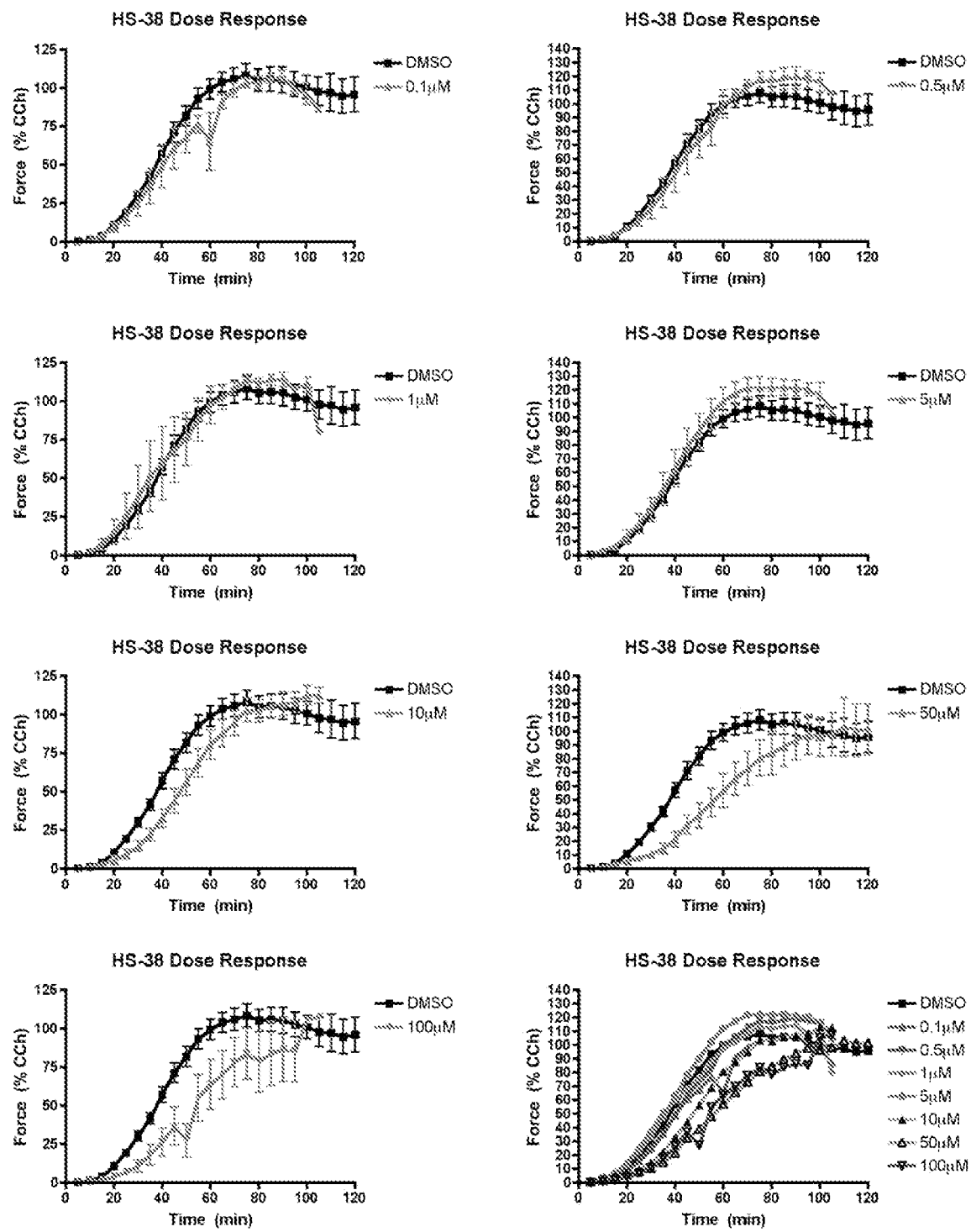
FIG. 21 shows the results of experiments to determine the effect of HS-38 on contractile force development of isolated rat ileal smooth muscle. The data are isometric contractile responses of ileal longitudinal smooth muscle isolated from male Sprague-Dawley rats. Forces generated during calyculin A (10 µM) administration were measured, and data are expressed as the absolute force found for HS-38 treatments normalized to an initial contraction with carbachol (% CCh). HS-38 was provided 30 min prior to the addition of calyculin A.

Results: HS-38 attenuated GI smooth muscle (i.e., ileum) contractile force development during the $Ca^{2+}$ sensitization process in a concentration-dependent manner. See FIG. 21.

Figure 22:
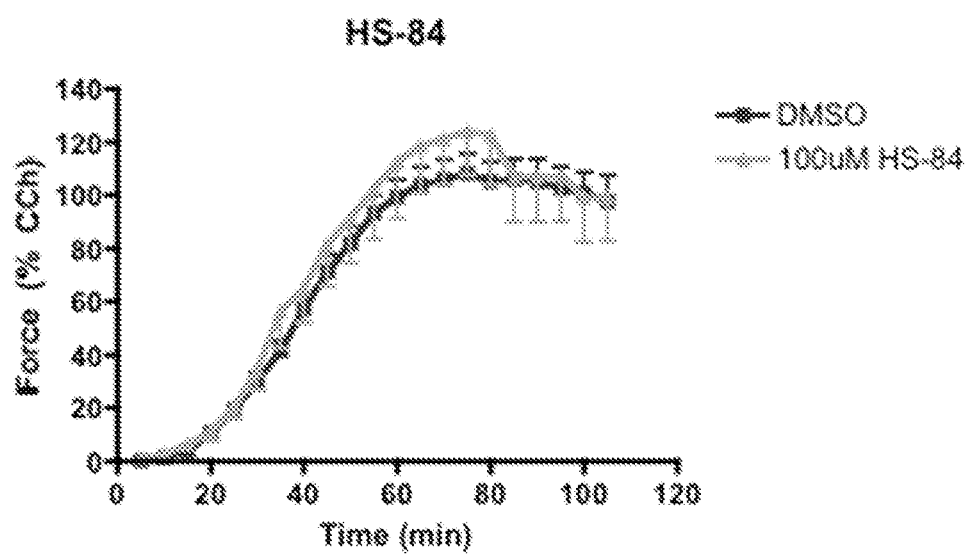
FIG. 22 shows the results of experiments to determine the effect of HS-84 on the contractile force development of isolated rat ileal smooth muscle. The data are isometric contractile responses of ileal longitudinal smooth muscle isolated from male Sprague-Dawley rats. Forces generated during calyculin A (10 µM) administration were measured, and data are expressed as the absolute force found with HS-84 treatment normalized to an initial contraction with carbachol (% CCh). HS-38 was provided 30 min prior to the addition of calyculin A.

Example 16. HS-84 has No Effect on the Contractile Force Development of Isolated Rat Ileal Smooth Muscle Compounds on the HS-38 pyrimidinone backbone (e.g., HS-84) display potent Pimk inhibition without any activity toward ZIPK. These molecules were used with isolated rat (male, Sprague-Dawley) ileum to confirm that there are no contributions of Pimk1/3 to contractile processes in this GI smooth muscle. Muscle experiments were performed as described in Example 15. See FIG. 22.

Example 17. Synthesis of HS38

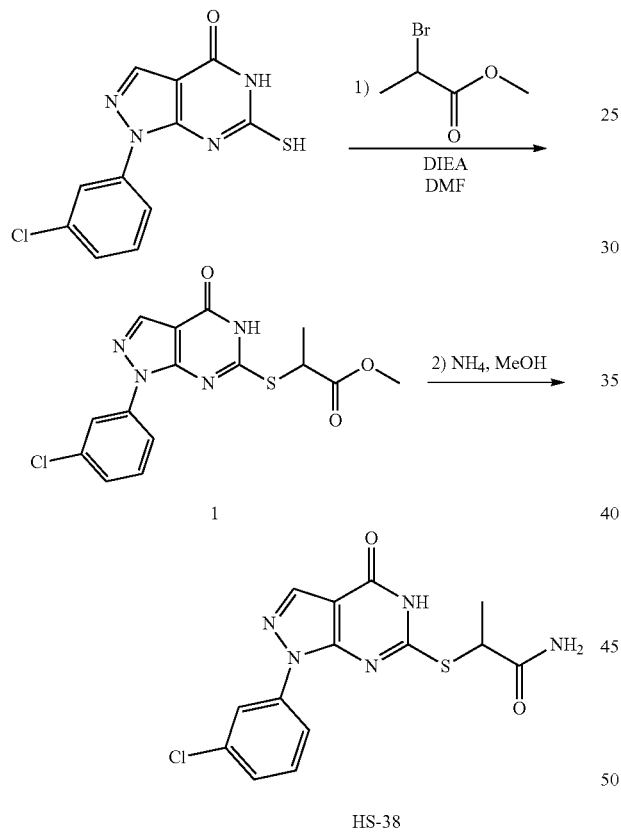

Synthesis of methyl 2-((1-(3-chlorophenyl)-4-oxo-4,5-dihydro-1H-pyrazolo[3,4-d]pyrimidin-6-yl)thio)propanoate (1)

1-(3-chlorophenyl)-6-mercapto-1,3a,7,7a-tetrahydro-4H-pyrazolo[3,4-d]pyrimidin-4-one (500 mg, 1.8 mmol) was dissolved in $CH_2Cl_2$ (5 mL) and treated with diisopropylethylamine (630 μL) and methyl 2-bromopropionate (329 mg, 1.97 mmol). After stirring for 24 h, the mixture was adsorbed onto silica (4 g) and added to a silica gel column (18×2.5 cm), flushed with $CH_2Cl_2$ (150 mL), and chromatographed (10% MeOH in $CH_2C2$, 400 mL). The resulting solid was triturated with water and filtered to give 2-((1-(3-chlorophenyl)-4-oxo-4,5-dihydro-H-pyrazolo[3,4-d]pyrimidin-6-yl)thio)propanoate (1) (574 mg, 88%) as a white powder.

Synthesis of (2-((1-(3-chlorophenyl)-4-oxo-4,5-dihydro-1H-pyrazolo[3,4-d]pyrimidin-6-yl)thio)propanamide (HS38)

To the methyl ester (1) (100 mg, 275 μmol) was added 7 N ammonia in methanol (3 mL) and the mixture was heated to 65° C. in a sealed vial. After 12 h, the reaction was condensed to dryness and the resulting solid was triturated with methanol in dichloroethane (1:1, 5 mL) and heated to 65° C. Upon cooling, the solid was filtered and washed with methanol (5 mL) to give HS38 (77 mg, 80%) as a white powder. Proton NMR matched that of the commercially available material. $^1H$ NMR (500 MHz, dmso-$d_6$) δ 12.84 (s, 1H), 8.28 (s, 1H), 8.15 (s, 2H), 7.76 (s, 1H), 7.60 (t, J=8.0 Hz, 1H), 7.46 (d, J=7.8 Hz, 1H), 7.29 (s, 1H), 4.48 (q, J=7.0 Hz, 1H), 1.62 (d, J=6.8 Hz, 3H). MS (EI) m/z 350 $[M+H]^+$.

Example 18. Synthesis of m-Chlorophenyl, o-Chlorophenyl and Phenyl Compounds

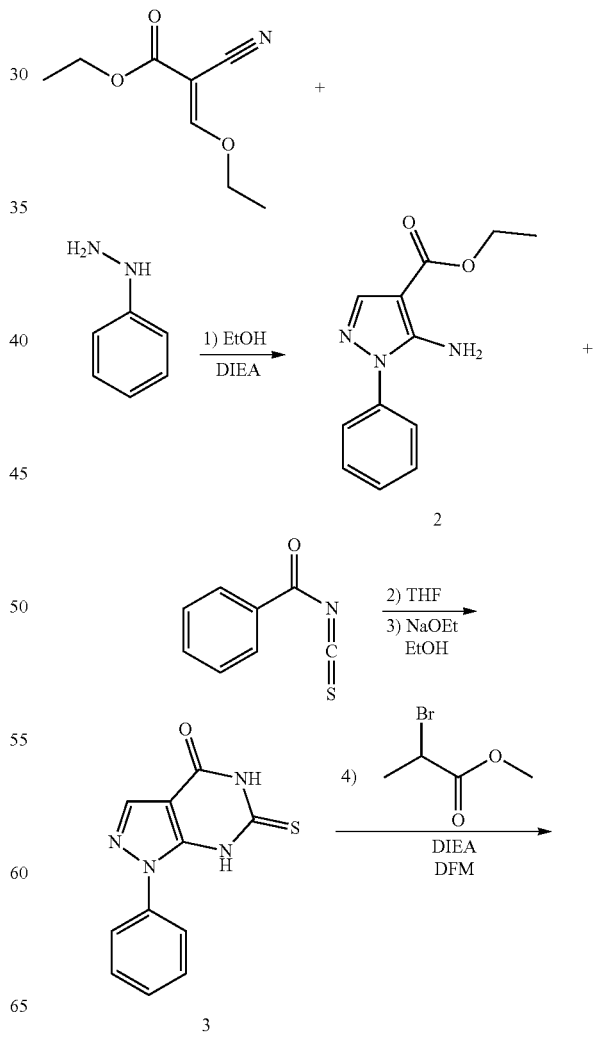

71

-continued

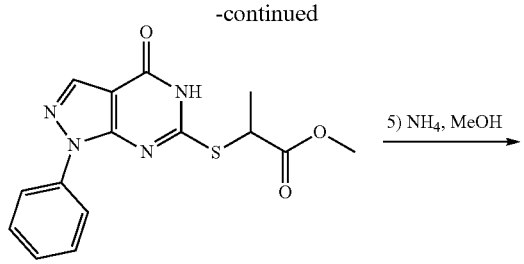

HS87

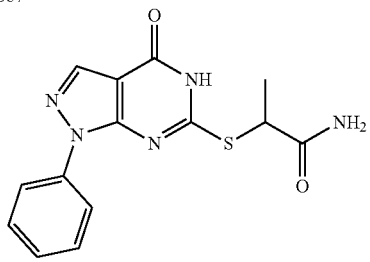

HS92

Compounds were prepared according to Scheme 1 using an appropriate electrophile for step 2 (either alkyl bromide or alkyl chloride).

Synthesis of Ethyl
5-amino-1-phenyl-H-pyrazole-4-carboxylate (2)

Ethyl-2-cyano-3-ethoxyacrylate (1.5 g, 8.9 mmol, 1 eq.) was dissolved in ethanol (10 mL) with N,N-diisopropylethylamine (0.74 mL, 9.8 mmol, 1.1 eq.) and phenylhydrazine (0.96 mL, 9.8 mmol, 1.1 eq.) and the solution was heated to 85° C. with stirring for 12 h. The reaction was condensed to dryness and dissolved in a minimal amount of dichloromethane and chromatographed on silica gel (20-30% ethyl acetate in hexane) to give ethyl 5-amino-1-phenyl-1H-pyrazole-4-carboxylate (2) as an orange solid (2.0 g, 96% yield). MS (EI) m/z 232 [M+H]$^+$.

Synthesis of 1-phenyl-6-thioxo-1,5,6,7-tetrahydro-4H-pyrazolo[3,4-d]pyrimidin-4-one (3)

Ethyl 5-amino-1-phenyl-1H-pyrazole-4-carboxylate (2) (1.0 g, 4.3 mmol, 1 eq.) was dissolved in THF (50 mL) and heated to reflux for 6 h. The mixture was cooled to room temperature and condensed to ~20 mL and then added dropwise to a refluxing mixture of anhydrous ethanol (65 mL) with sodium ethoxide (10 mL of a 21% solution in ethanol). The reaction was refluxed for 20 min and then removed from heat and neutralized with acetic acid (2 mL). The cloudy mixture was condensed, dissolved in DMSO/water (1:1) and purified by preparative HPLC (Agilent Prep C18 column, 21.2 mm I.D.) using 5-100% methanol in water (0.2% formic acid modifier) to give 1-phenyl-6-thioxo-1,5, 6,7-tetrahydro-4H-pyrazolo[3,4-d]pyrimidin-4-one (3) as a white solid (0.92 g, 73% yield). MS (EI) m-z 245 [M+H]$^+$.

Synthesis of methyl 2-((4-oxo-1-phenyl-4,5-dihydro-1H-pyrazolo[3,4-d]pyrimidin-6-yl)thio)propanoate (HS87)

The pyrimidone thione 2 (0.050 g, 0.2 mmol, 1 eq.) was dissolved in DMF (1 mL) with N,N-diisopropylethylamine (0.107 mL, 0.61 mmol, 3 eq) and methyl 2-bromopropionate (0.025 mL, 0.23 mmol, 1.1 eq) and stirred for 12 h. Water (0.2 mL) and acetic acid (0.050 mL) were added and the

72 mixture was injected directly onto a preparative HPLC (Agilent Prep C18 column, 21.2 mm I.D.) using 5-100% methanol in water (0.2% formic acid modifier) to give HS87 as a white solid (0.038 g, 56% yield). MS (EI) m/z 331 [M+H]$^+$.

Synthesis of 2-((4-oxo-1-phenyl-4,5-dihydro-1H-pyrazolo[3,4-d]pyrimidin-6-yl)thio)propanamide (HS92)

To the methyl ester (HS87) (0.016 g, 0.045 mmol) was added 7 N ammonia in methanol (2 mL) and the mixture was heated to 65° C. in a sealed vial fort 12 h. The reaction was condensed and placed on high vacuum to give HS92 (0.017 g, 100% yield) as a white solid. MS (EI) m/z 316 [M+H]$^+$.

General Procedure for Preparation of Phenyl Analogs.

Compounds were prepared according to Scheme 2 using an appropriate electrophile for step 4 (either alkyl bromide or alkyl chloride).

General Procedure for Preparation of o-Chlorophenyl Analogs.

Compounds were prepared according to Scheme 2 using (2-chlorophenyl)hydrazine in step 1 and an appropriate electrophile in step 4 (either alkyl bromide or alkyl chloride).

Example 19. Compound Screening Against ZIPK, PIM1 and PIM3

Additional compounds were synthesized and tested against ZIPK1, PIM1 and PIM3. Compounds and their EC50 values are shown in the table in FIG. 23. All of the compounds shown FIG. 23 were synthesized according to Example 18, and structures were verified using standard methods known in the art. The compounds have the following structures:

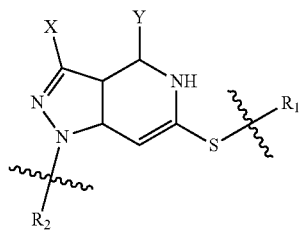

wherein in each case, X is H and Y is =O.

Figure 24:
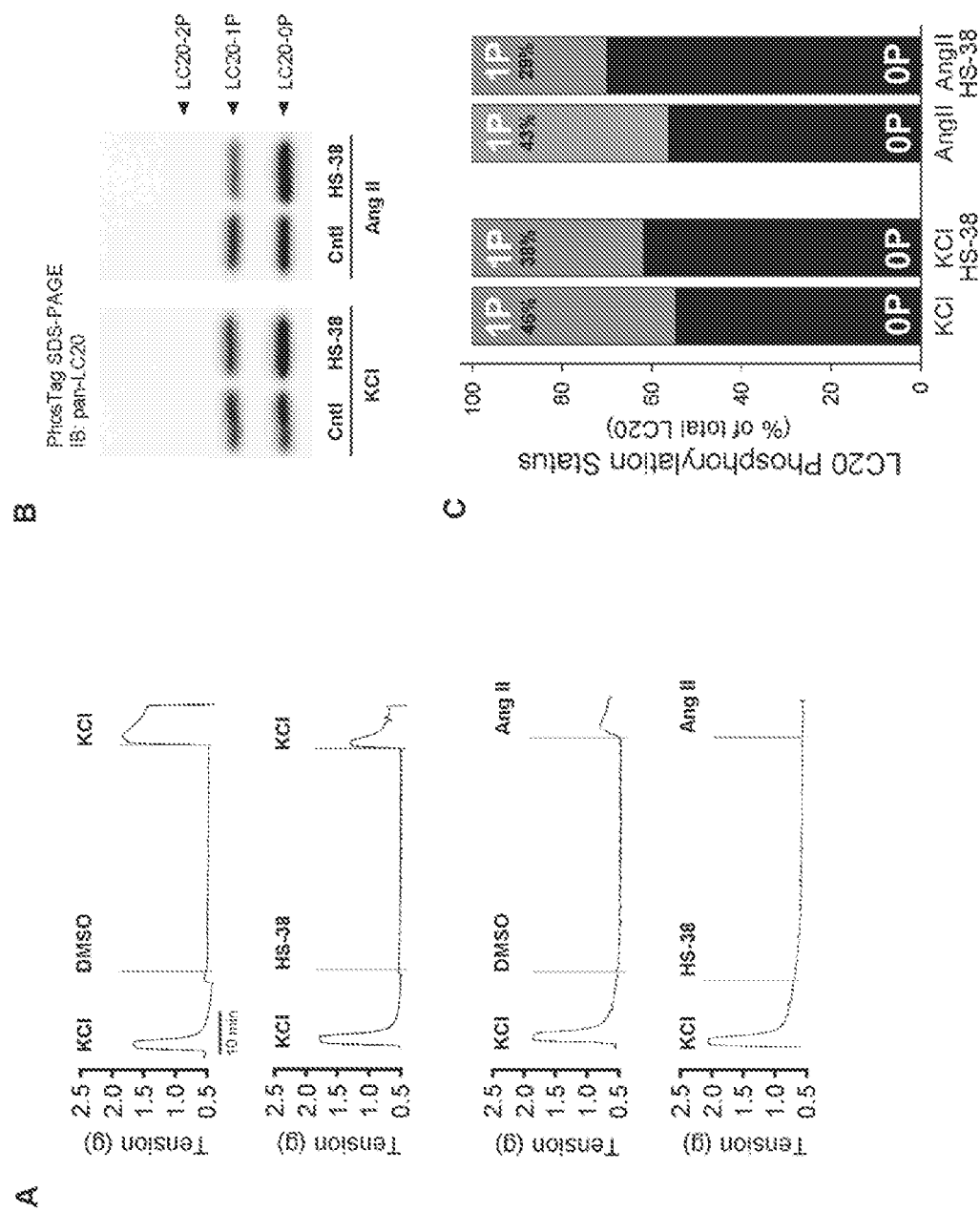
FIG. 24 shows the results of experiments to determine the effect of HS-38 on KCl and Ang II-dependent contraction and LC20 phosphorylation of isolated RTA. A, intact RTA strips were stimulated to contract with exposure to high-extracellular K+ solution (KCl) or Ang II (10 µM) in normal HEPES extracellular solution. Experiments were also performed with addition of the ZIPK inhibitor (HS-38, 50 µM). There are major differences in the sensitivity of RTA to contractile agonists. In this case, Ang II elicits a slower and weaker response than KCl. The addition of HS-38 decreased maximal force generated by either stimulus. For the KCl stimulated contraction, exposure to HS-38 had a greater effect on the sustained, tonic contraction ($Ca^{2+}$-sensitization) than on the initial phasic contraction ($Ca^{2+}$-dependent). The Ang II-dependent contraction was completely inhibited with HS-38, suggesting a greater dependence on $Ca^{2+}$-sensitization pathways. Vessels were flash-frozen at the peak of contraction, and LC20 phosphorylation was assessed with PhosTag gels. B, HS-38 could attenuate the levels of LC20 monophosphorylation induced by KCl and Ang II. C, data are n=1 for RTA vessels from Sprague-Dawley rats.

Example 20. Effect of HS-38 Administration on KCl and Ang H-Dependent Contraction and LC20 Phosphorylation of Isolated RTA Intact RTA strips were stimulated to contract with exposure to high-extracellular K+ solution (KCl) or Ang II (10 μM) in normal HEPES extracellular solution. Experiments were also performed with addition of the ZIPK inhibitor (HS-38, 50 μM). There are major differences in the sensitivity of RTA to contractile agonists. In this case, Ang II elicits a slower and weaker response than KCl. The addition of HS-38 decreased maximal force generated by either stimulus. For the KCl stimulated contraction, exposure to HS-38 had a greater effect on the sustained, tonic contraction (Ca$^{2+}$-sensitization) than on the initial phasic contraction (Ca$^{2+}$-dependent). As seen in FIG. 24, the Ang II-dependent contraction was completely inhibited with HS-38, suggesting a greater dependence on Ca2$^+$-sensitization pathways. Vessels were flash-frozen at the peak of contraction, and LC20 phosphorylation was assessed with PhosTag gels (B).

HS-38 could attenuate the levels of LC20 monophosphorylation induced by KCl and Ang II (C). Data are n=1 for RTA vessels from Sprague-Dawley rats.

Figure 25:
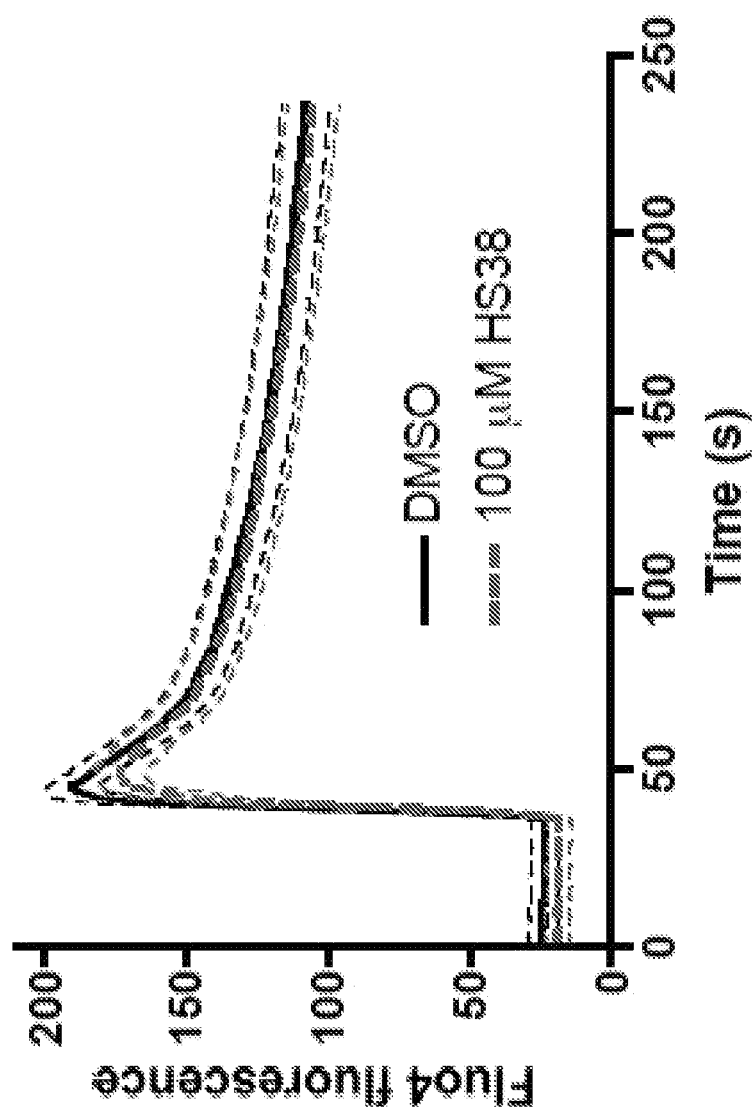
FIG. 25 is a graph of time versus Fluo4 fluorescence for control (DMSO) and HS-38-treated rat caudal arteries.

Example 21. HS38 Showed No Effect on Intracellular [Ca2+] in Rat Caudal Artery Tissue Rat caudal arteries were isolated. The intracellular Ca2+ concentration was measured in medial smooth muscle of the caudal artery using Fluo-4. KCl was injected to a final concentration of 100 µM after 45 confocal frame scans (i.e., at 35 sec). Results are shown in FIG. 25, wherein traces represent the mean S.E.M. of the raw fluorescence from control (DMSO, black line) and HS-38-treated (red line) preparations (N=13 preparations and 6 animals per condition). The results support the absence of any off-target effect of HS-38 on Ca2+ levels in vascular smooth muscle tissue.

The latency period, i.e. the time from addition of calyculin A to the onset of contraction, and the half-time from the initiation of contraction to the plateau of the contractile response, were determined, in addition to the t1/2 values (the half-time from addition of calyculin A to the plateau of the contractile response) determined previously, in the absence and presence of HS-38. The results, presented TABLE 2, show that all 3 parameters were significantly increased by the ZIPK inhibitor. On the other hand, the steady-state level of force induced by calyculin A was unaffected by ZIPK inhibition. The results support the ability of HS38 to suppress the initiation and rate of contractile tone without altering the total force potential of the muscle.

TABLE 2

| Parameter | Control (n = 94) | +HS-38 (n = 28) |
| --- | --- | --- |
| Latency (s) | 361.0 ± 15.1 (146.1) | *654.7 ± 60.6 (320.4) |
| t1/2 from stimulation (s) | 1082.9 ± 37.9 (367.0) | *1792.0 ± 110.8 (586.1) |
| t1/2 from contraction (s) | 702.0 ± 25.6 (248.5) | *1170.1 ± 64.0 (338.9) |
| % KCl contraction | 159.3 ± 5.1 (49.0) | **161.7 ± 8.4 (44.7) |

"Control" denotes calyculin A alone,
"+HS-38" denotes cayculin A with HS-38;
values indicate mean ± SEM (SD);
*significantly different from control (p < 0.0001 by Student's unpaired t test);
**p = 0.81.

Example 22. Application of HS38 in Animal (Rat) Models of Vascular Myopathy

Figure 26:
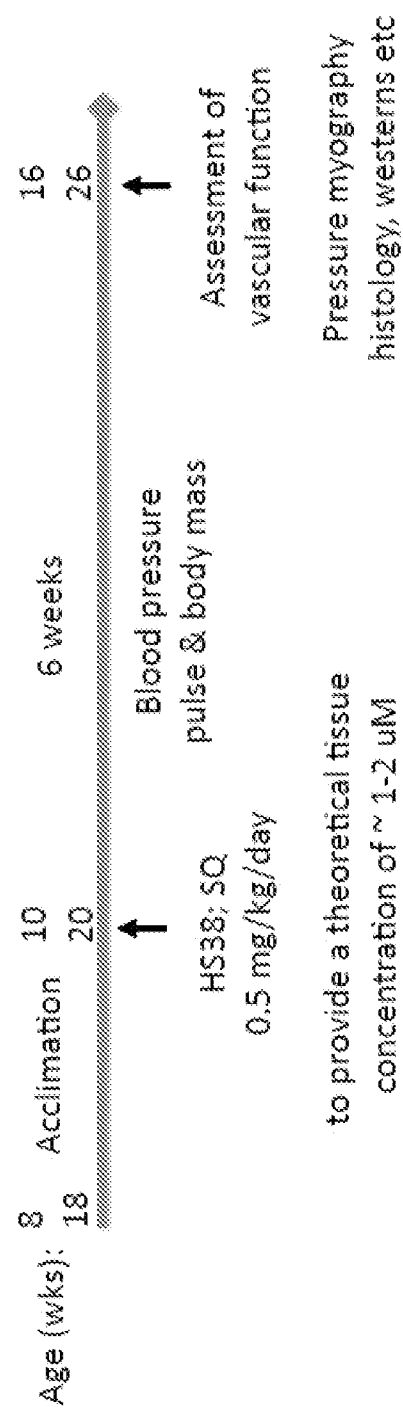
FIG. 26 is a schematic of the experiment to examine the myogenic response and ZIP-dependency of pressure autoregulation with HS-38 treatment.
Figure 27:
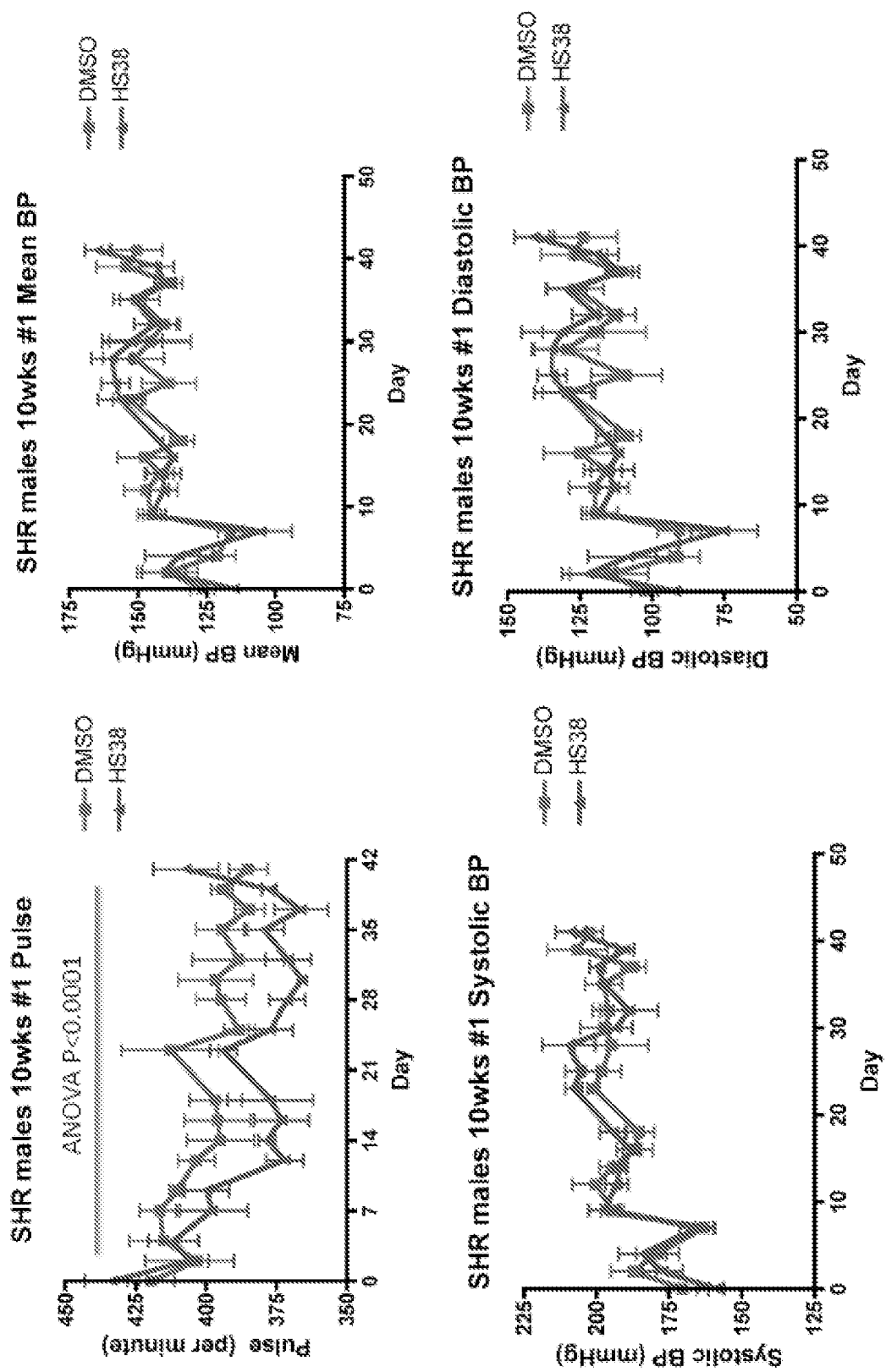
FIG. 27 are graphs of pulse, mean blood pressure, systolic blood pressure, and diastolic blood pressure over time in 10-week spontaneous hypertensive rats with control (DMSO) and HS-38 treatment.
Figure 28:
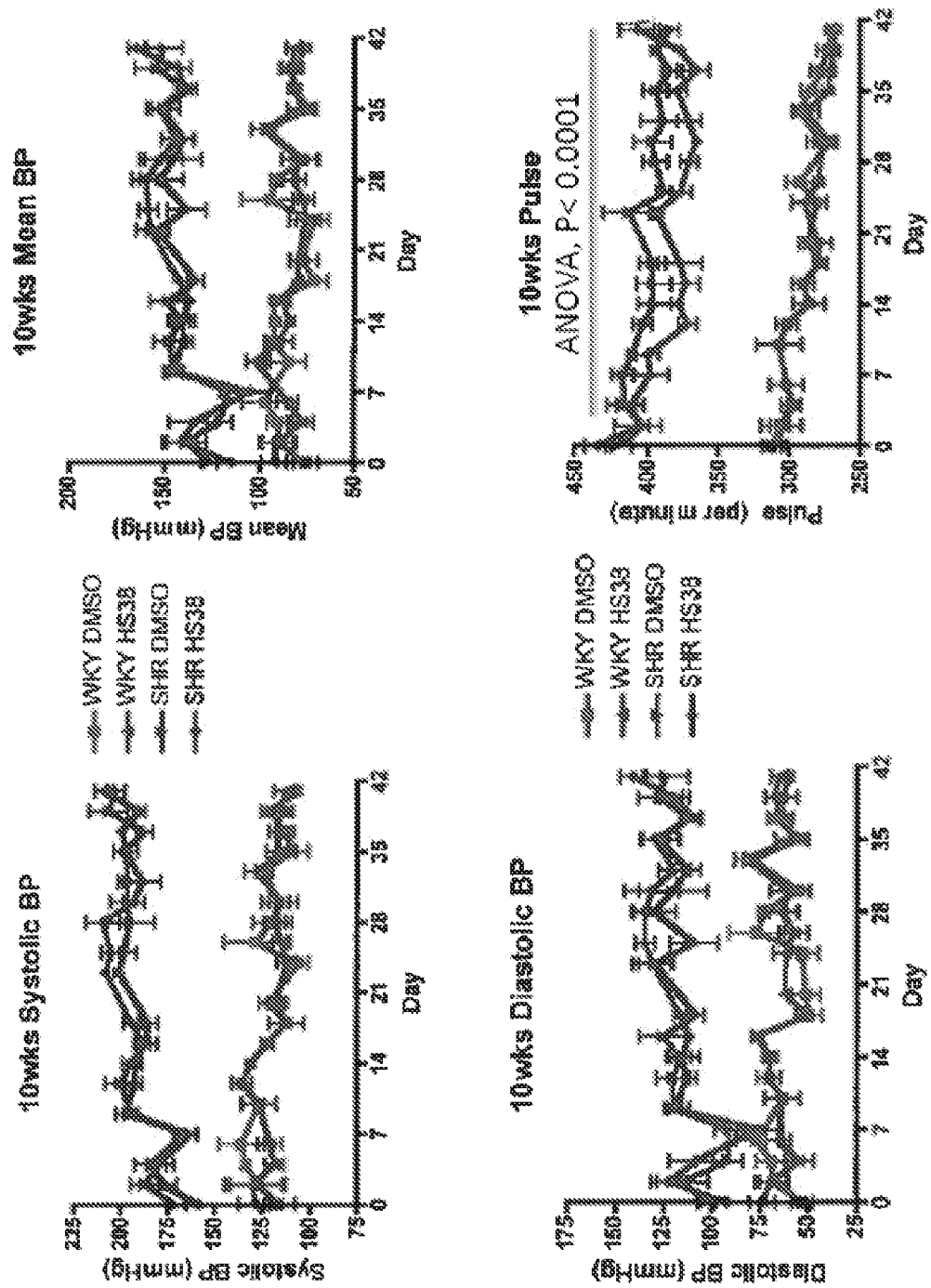
FIG. 28 are graphs of pulse, mean blood pressure, systolic blood pressure, and diastolic blood pressure over time in 10-week spontaneous hypertensive rats and Wistar Kyoto rats with control (DMSO) and HS-38 treatment.
Figure 29:
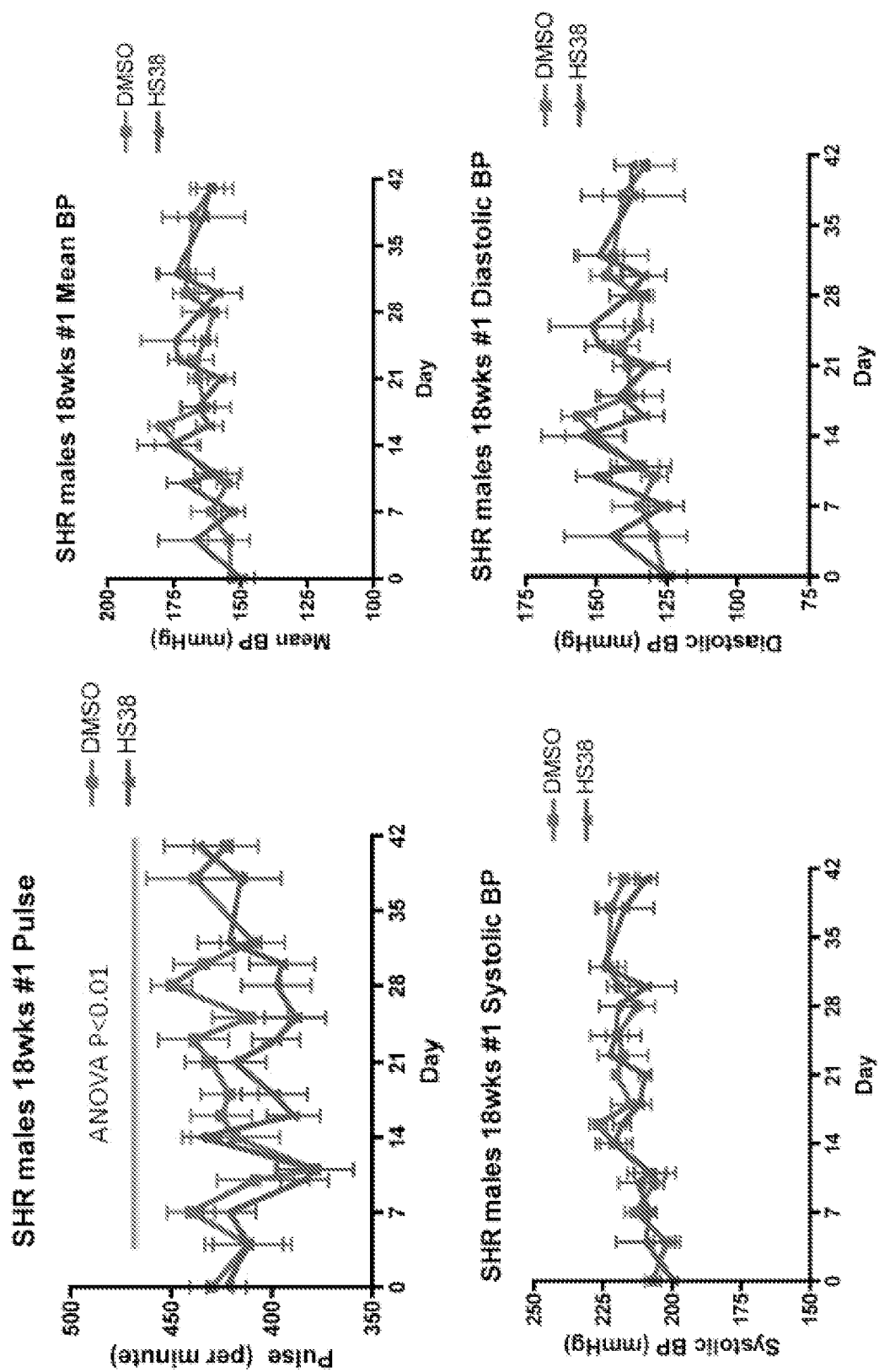
FIG. 29 are graphs of pulse, mean blood pressure, systolic blood pressure, and diastolic blood pressure over time in 10-week spontaneous hypertensive rats with control (DMSO) and HS-38 treatment.
Figure 30:
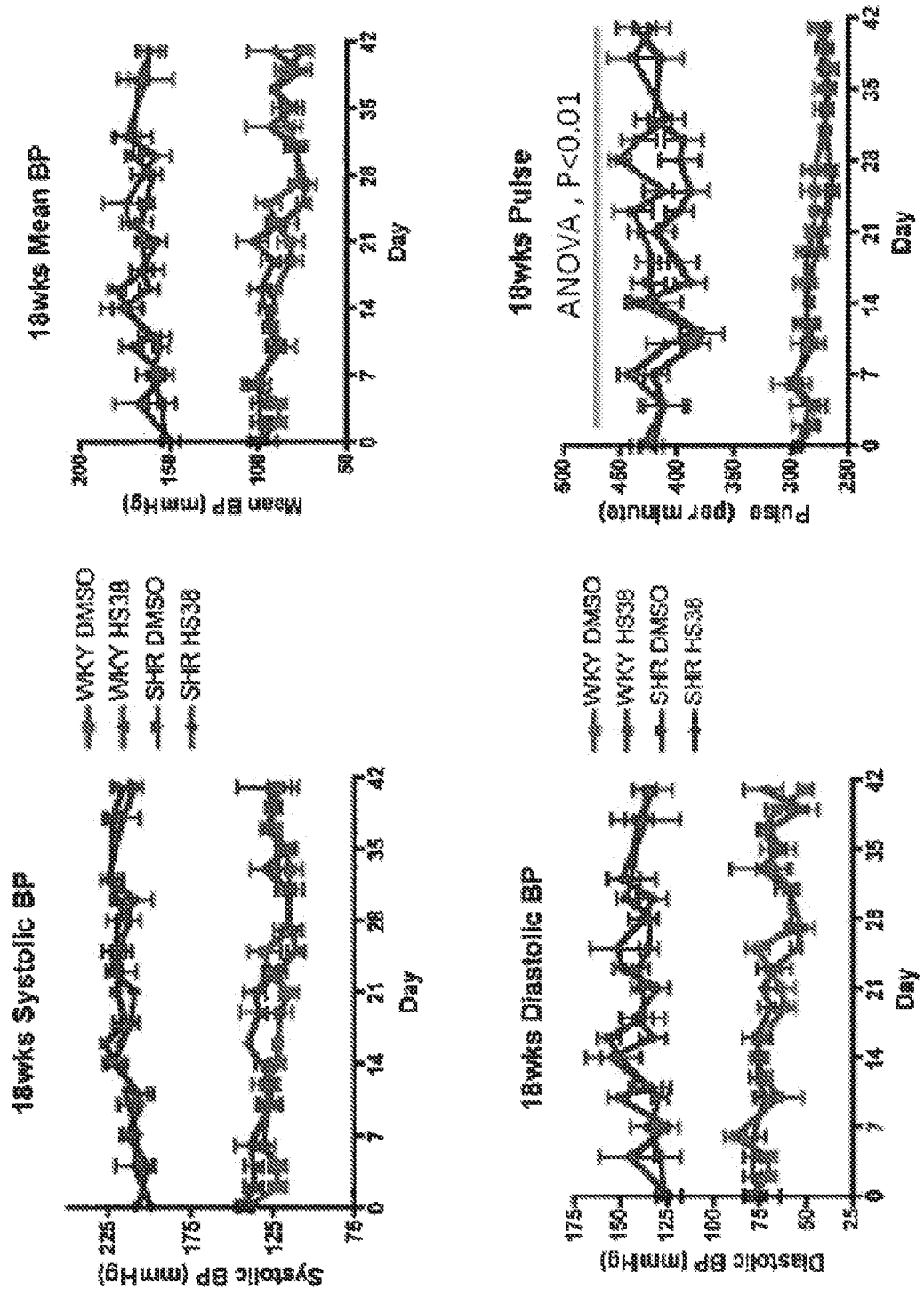
FIG. 30 are graphs of pulse, mean blood pressure, systolic blood pressure, and diastolic blood pressure over time in 18-week spontaneous hypertensive rats and Wistar Kyoto rats with control (DMSO) and HS-38 treatment.
Figure 31:
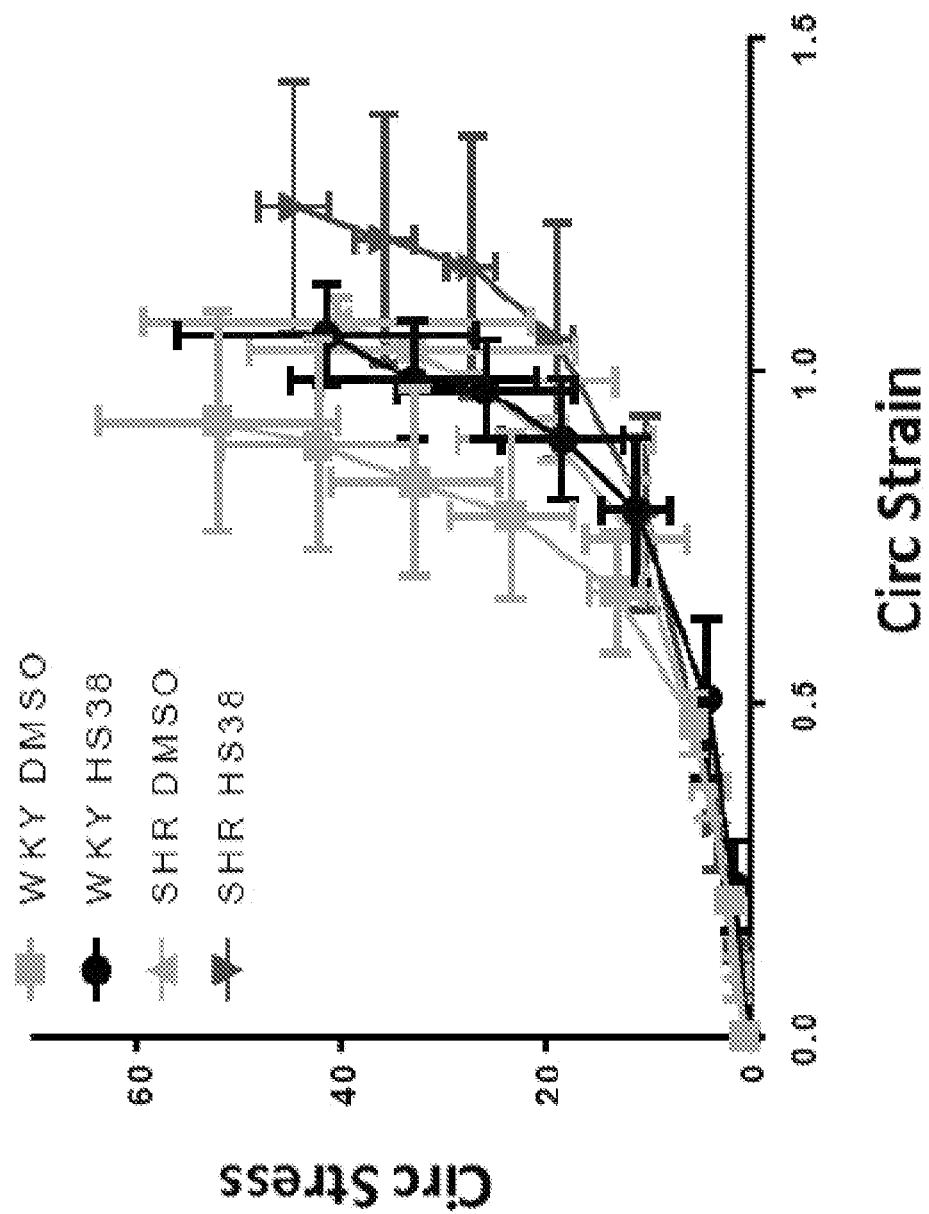
FIG. 31 is a graph of circumferential strain versus circumferential stress for spontaneous hypertensive rats and Wistar Kyoto rats with control (DMSO) and HS-38 treatment.
Figure 32:
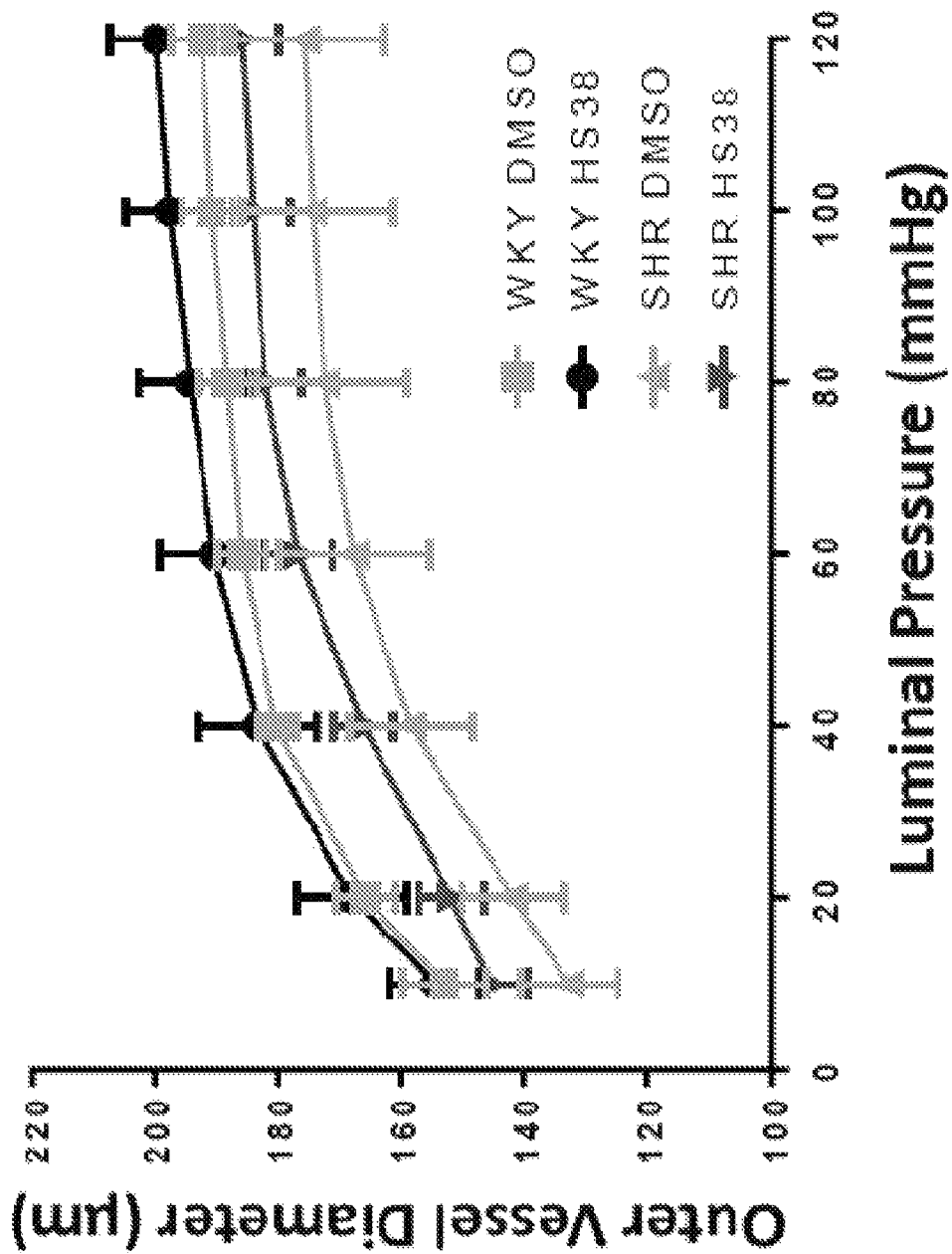
FIG. 32 is a graph of luiminal pressure versus outer vessel diameter for spontaneous hypertensive rats and Wistar Kyoto rats with control (DMSO) and HS-38 treatment.
Figure 33:
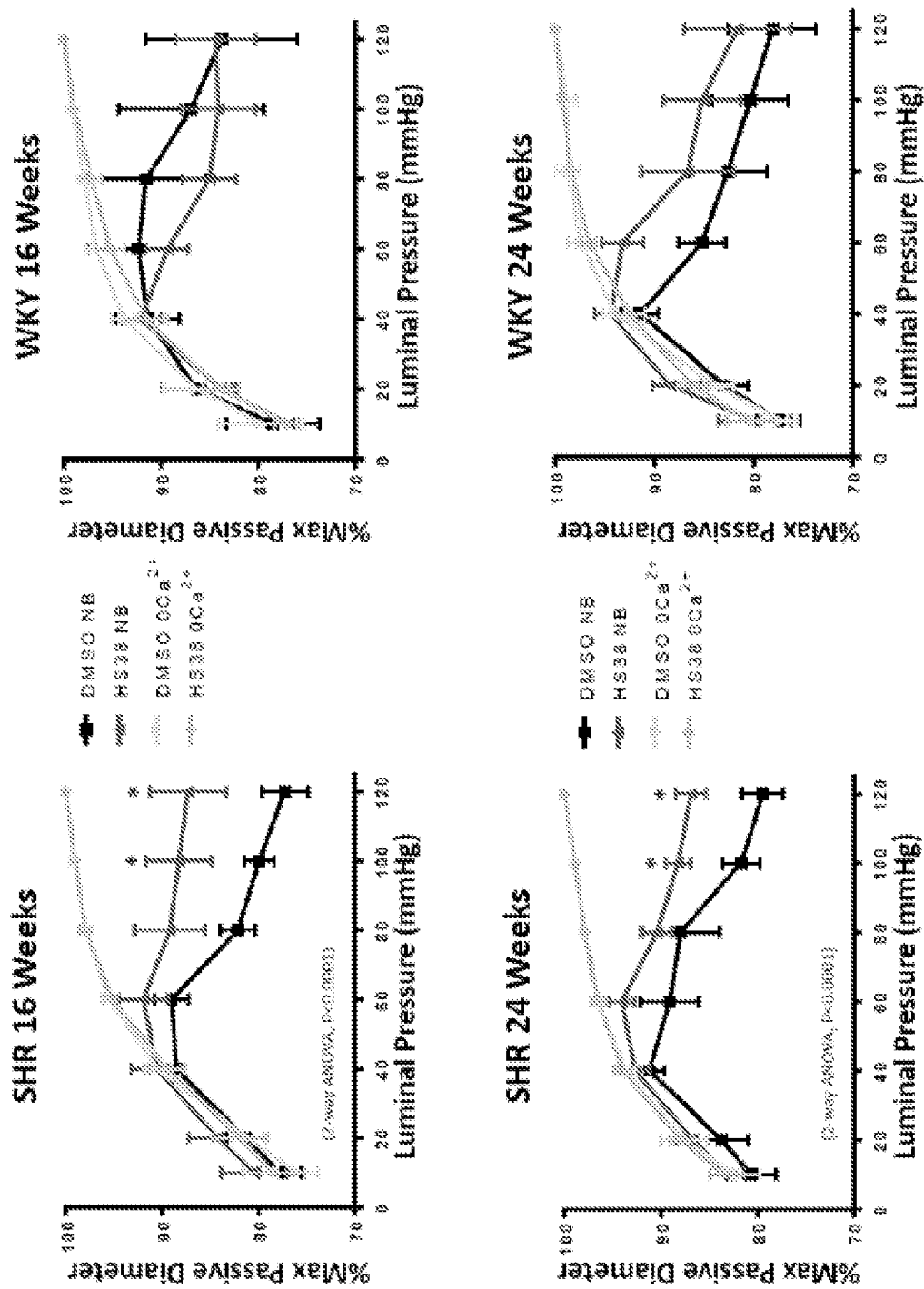
FIG. 33 are graphs of luminal pressure versus percent maximum passive diameter for 16 and 24 week spontaneous hypertensive rats and 16 and 24 week Wistar Kyoto rats with control (DMSO) and HS-38 treatment.
Figure 34:
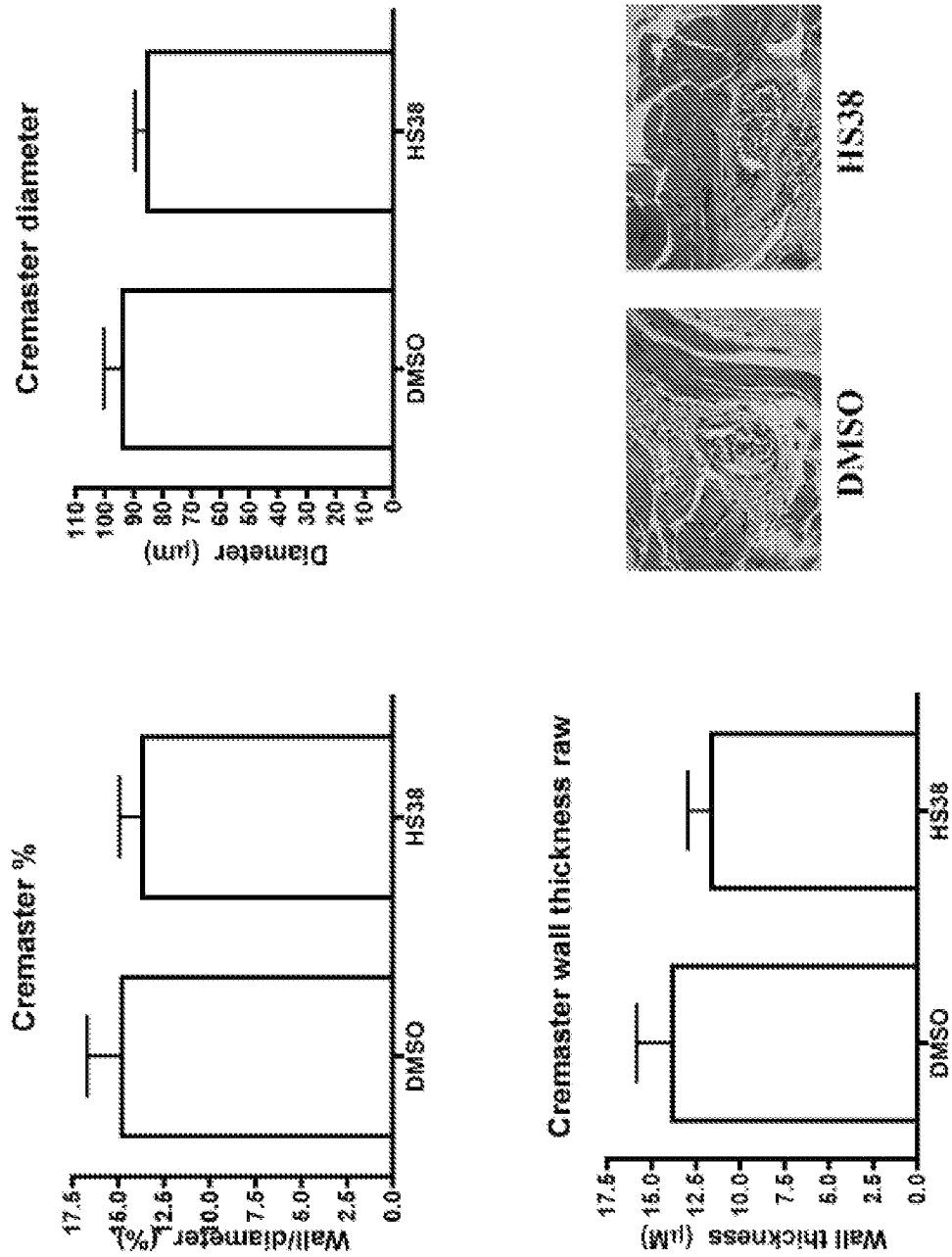
FIG. 34 are graphs of wall/diameter, diameter, and wall thickness for cremaster for DMSO (control) and HS-38-treated 10 week Wistar Kyoto rats.
Figure 35:
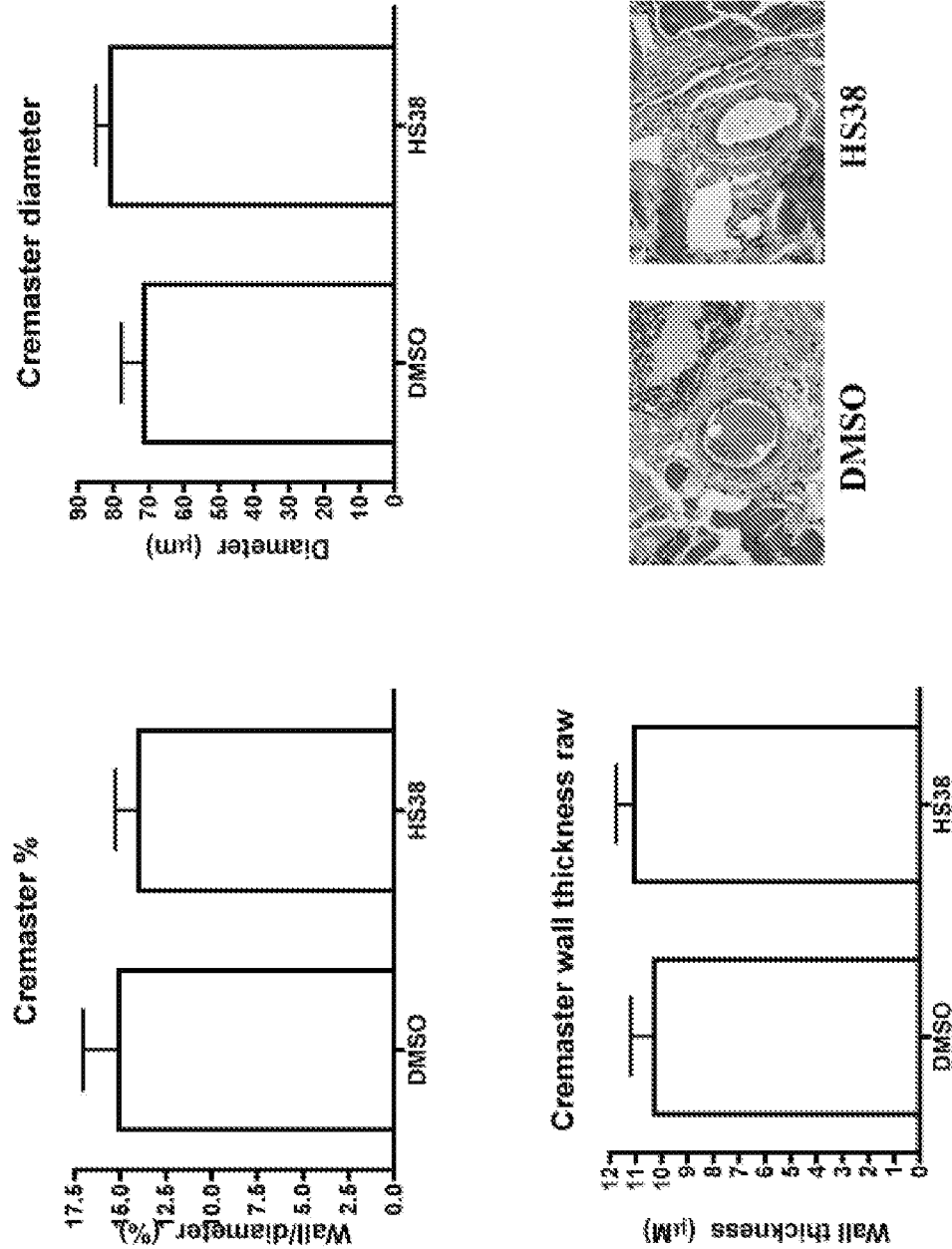
FIG. 35 are graphs of wall/diameter, diameter, and wall thickness for cremaster for DMSO (control) and HS-38-treated 18 week Wistar Kyoto rats.
Figure 36:
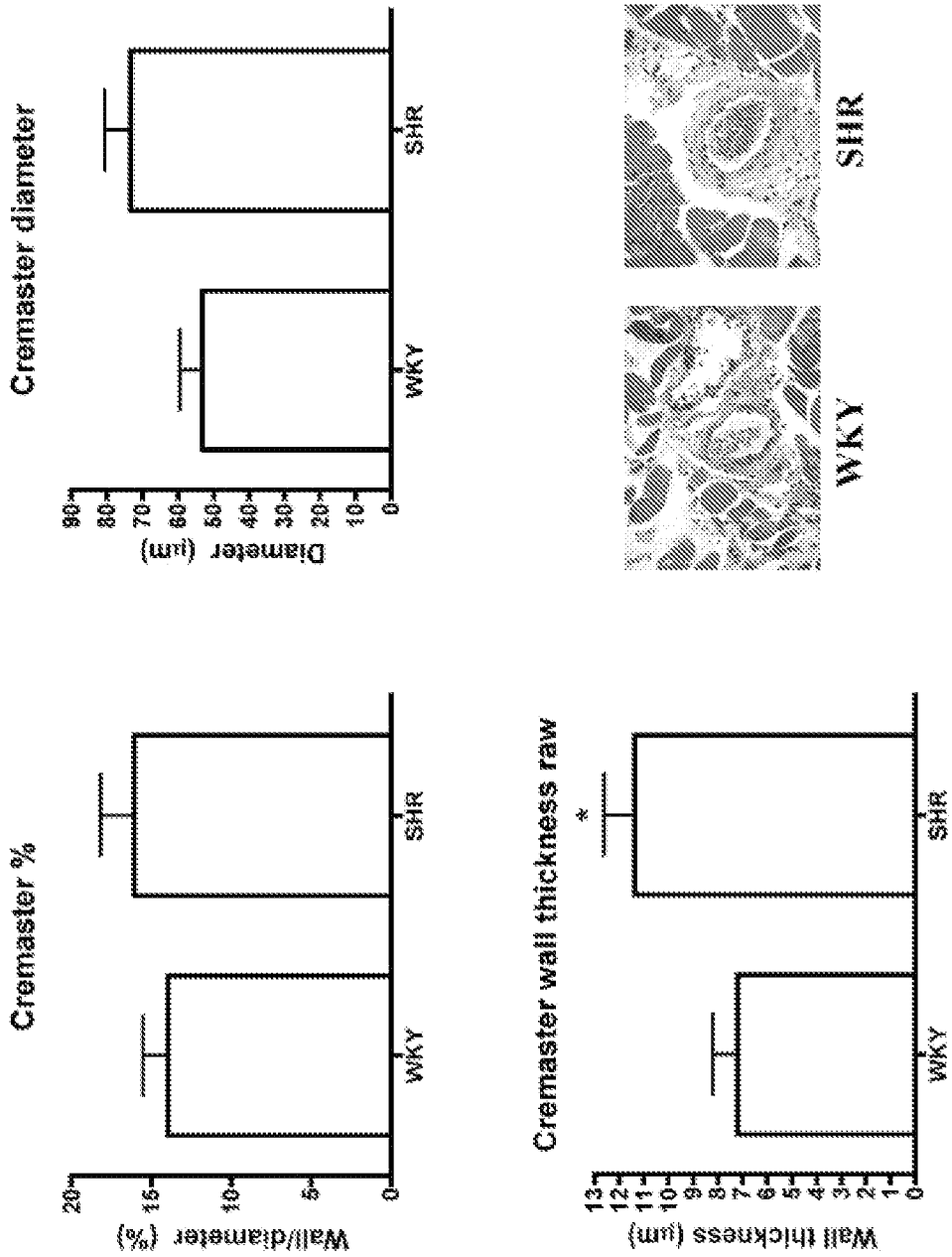
FIG. 36 are graphs of wall/diameter, diameter, and wall thickness for cremaster for spontaneous hypertensive rats and Wistar Kyoto rats.
Figure 37:
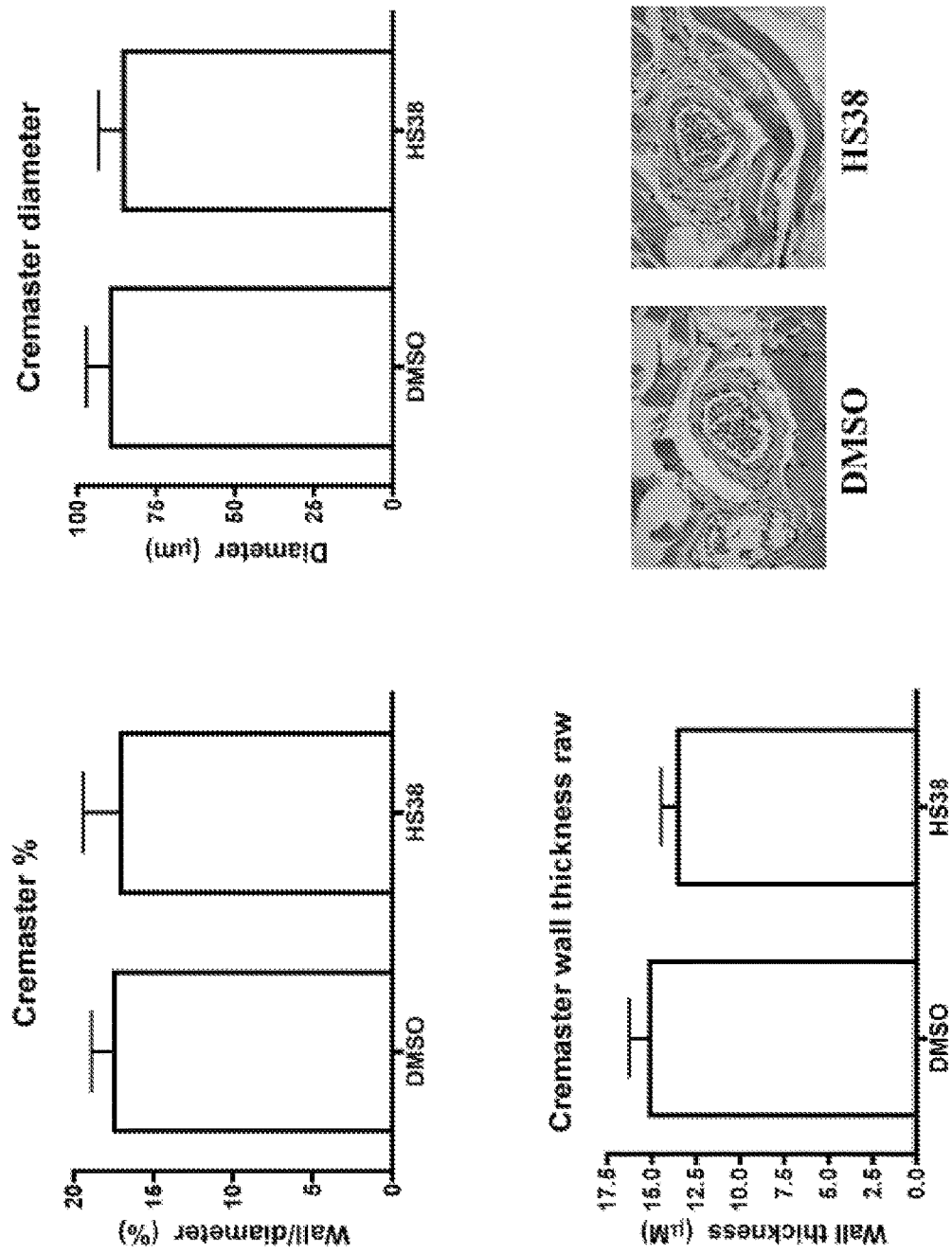
FIG. 37 are graphs of wall/diameter, diameter, and wall thickness for cremaster for DMSO (control) and HS-38-treated 10 week spontaneous hypertensive rats.
Figure 38:
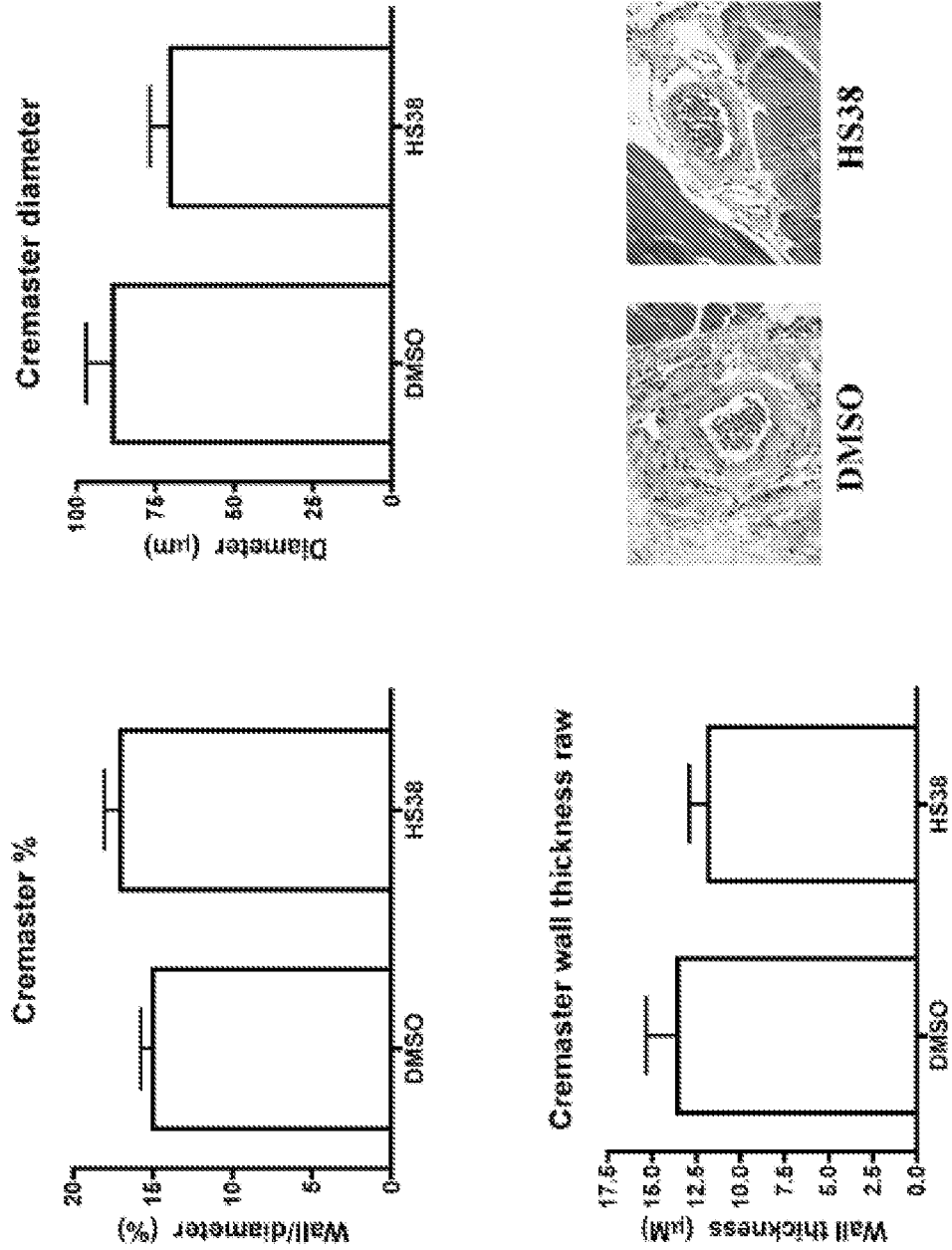
FIG. 38 are graphs of wall/diameter, diameter, and wall thickness for cremaster for DMSO (control) and HS-38-treated 18 week spontaneous hypertensive rats.

The myogenic response and ZIP-dependency of pressure autoregulation were assessed. Two age groups, 8-10 weeks and 18-20 weeks, were used to permit identification of age-dependent alterations in myogenic responses associated with the onset of diabetes/hypertension and after the diseases had become fully established. The experimental scheme is shown in FIG. 26. Two rat models were used, spontaneous hypertensive rat (SHR) model, and Goto-Kakizaki (GK) rat model of type 2 diabetes (T2D). Results are shown in FIGS. 27-33. Hypertension and HS-38 treatment increased circumferential strain (FIG. 31). HS-38 treatment partially reversed vessel narrowing seen in hypertension (FIG. 32). HS-38 treatment attenuated myogenic hypercontractility in the cremaster artery of spontaneously-hypertensive rats (SHR; FIG. 33; WKY=Wistar Kyoto rat, control).

The data shown in FIGS. 34-38 is suggestive of HS-38 effects on contractile physiology/pathophysiology via ZIPK targets that regulate vascular smooth muscle tone/force development rather than vessel wall remodeling (vascular smooth muscle cell proliferation and hypertrophy observed in hypertension). No effect of HS38 was observed on the ratio of wall thickness/vessel diameter in the SHR mesenteric artery.

Figure 39:
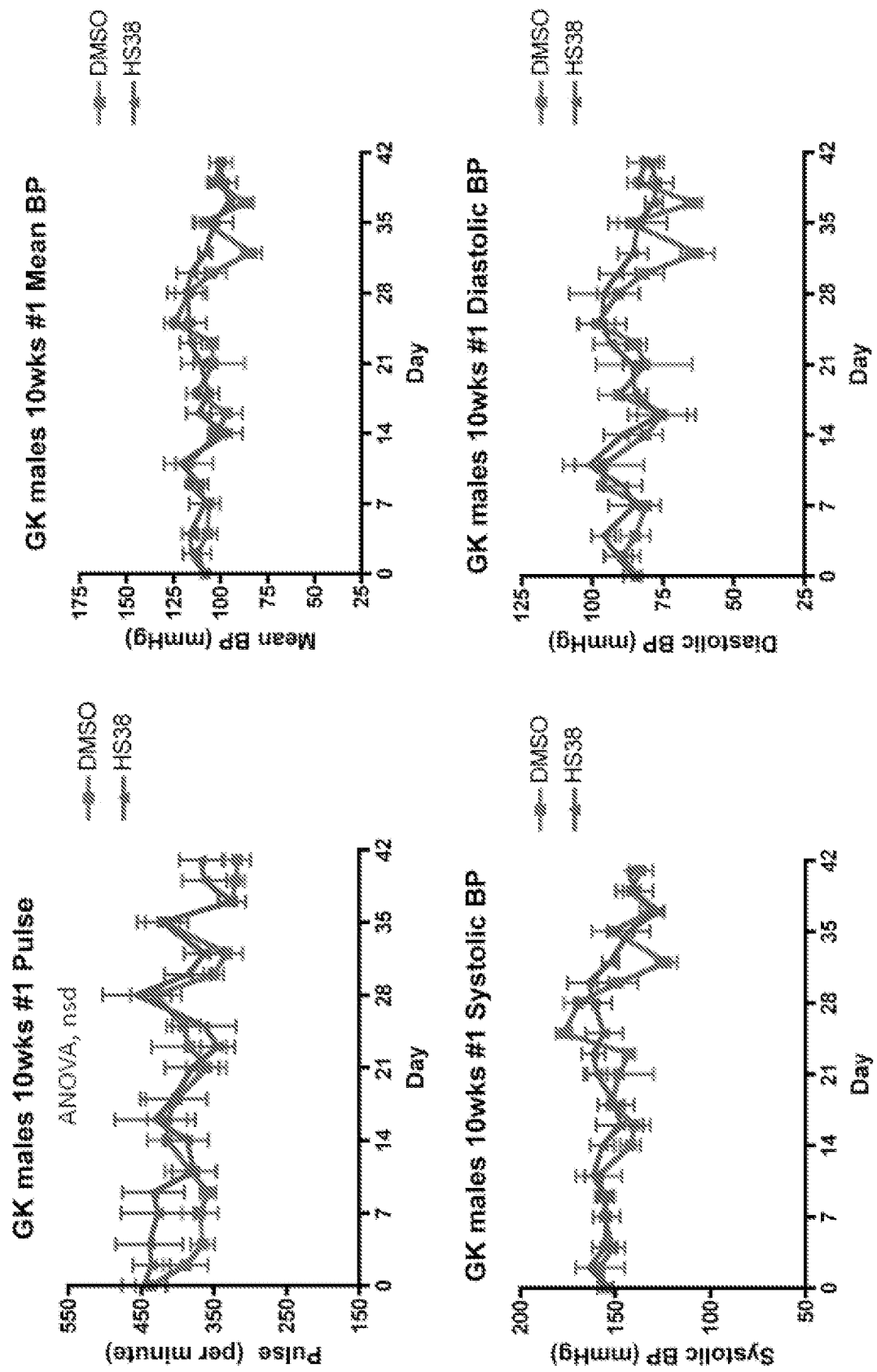
FIG. 39 are graphs of pulse, mean blood pressure, systolic blood pressure, and diastolic blood pressure over time in 10-week Goto-Kakizaki rats with control (DMSO) and HS-38 treatment.
Figure 40:
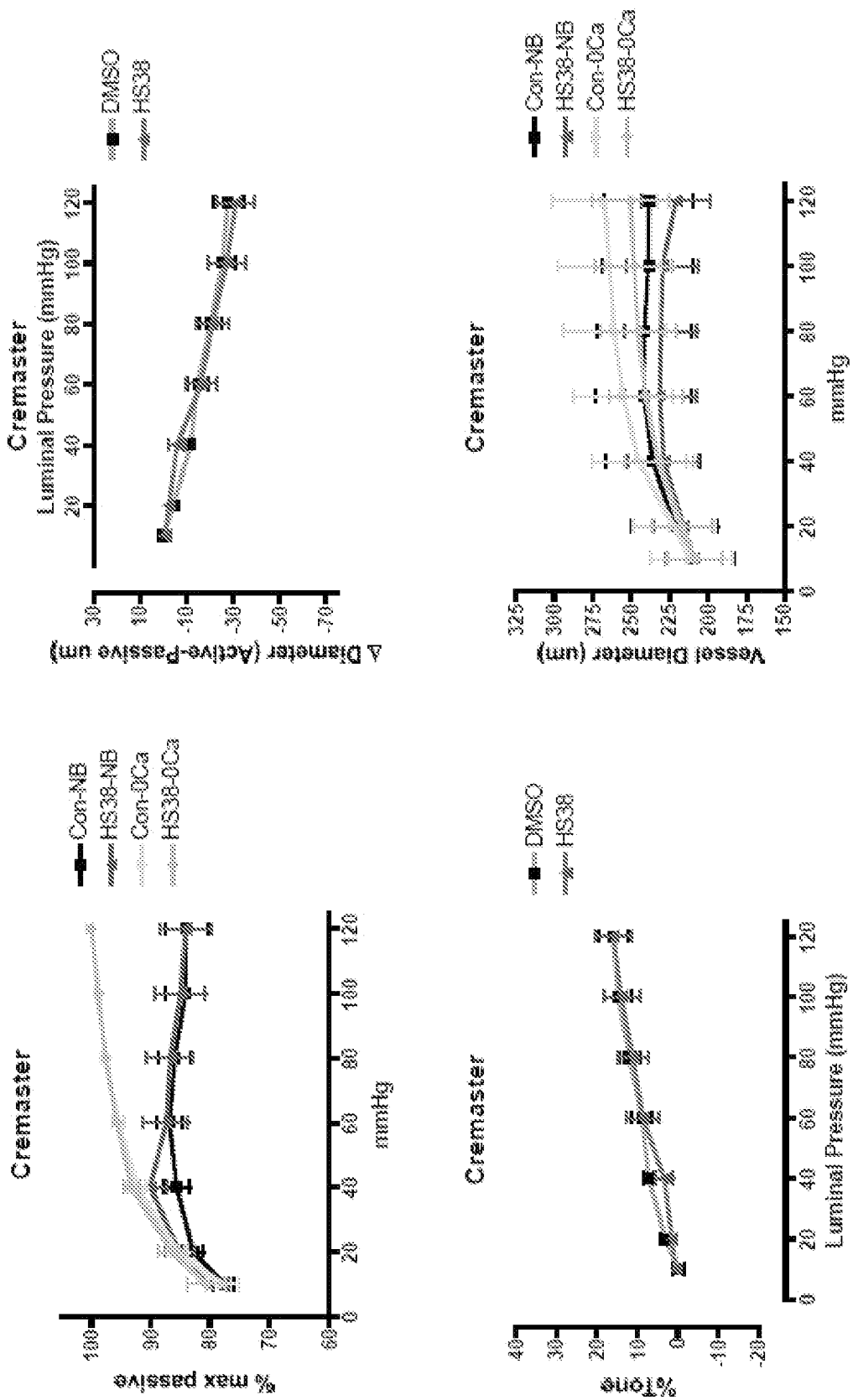
FIG. 40 are graphs of percent maximum passive versus pressure, change in diameter versus pressure, percent tone versus pressure, and vessel diameter versus pressure to show the effects of HS-38 dosing on the resistance vessel contractile responses to pressure for male 10-week Goto-Kakizaki rats.
Figure 41:
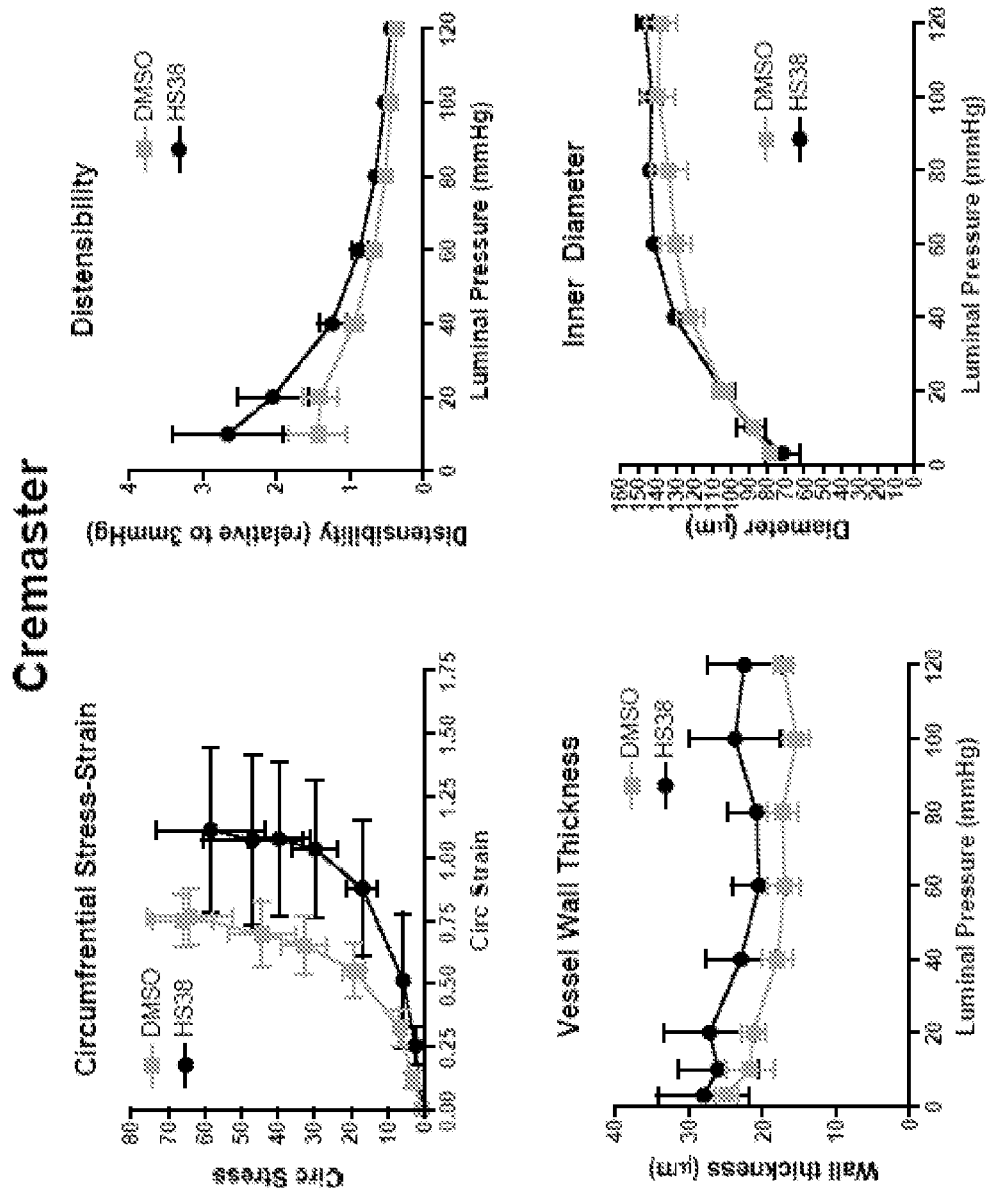
FIG. 41 are graphs of circumferential strain versus circumferential stress, pressure versus distensibility, pressure versus wall thickness, and pressure versus diameter to show the effects of HS-38 dosing on resistance vessel wall dynamics for male 10-week Goto-Kakizaki rats.
Figure 42:
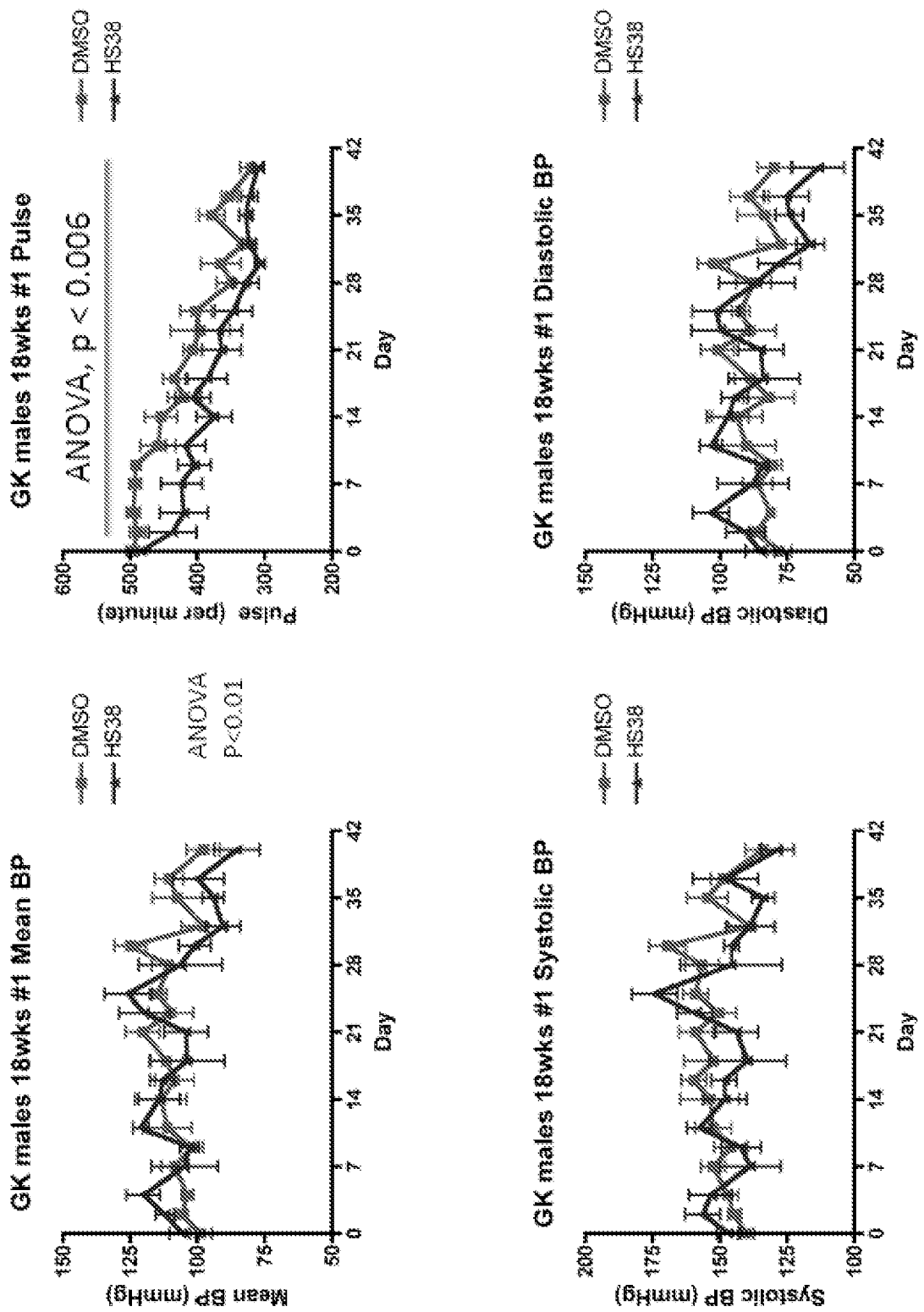
FIG. 42 are graphs of pulse, mean blood pressure, systolic blood pressure, and diastolic blood pressure over time in 18-week Goto-Kakizaki rats with control (DMSO) and HS-38 treatment.
Figure 43:
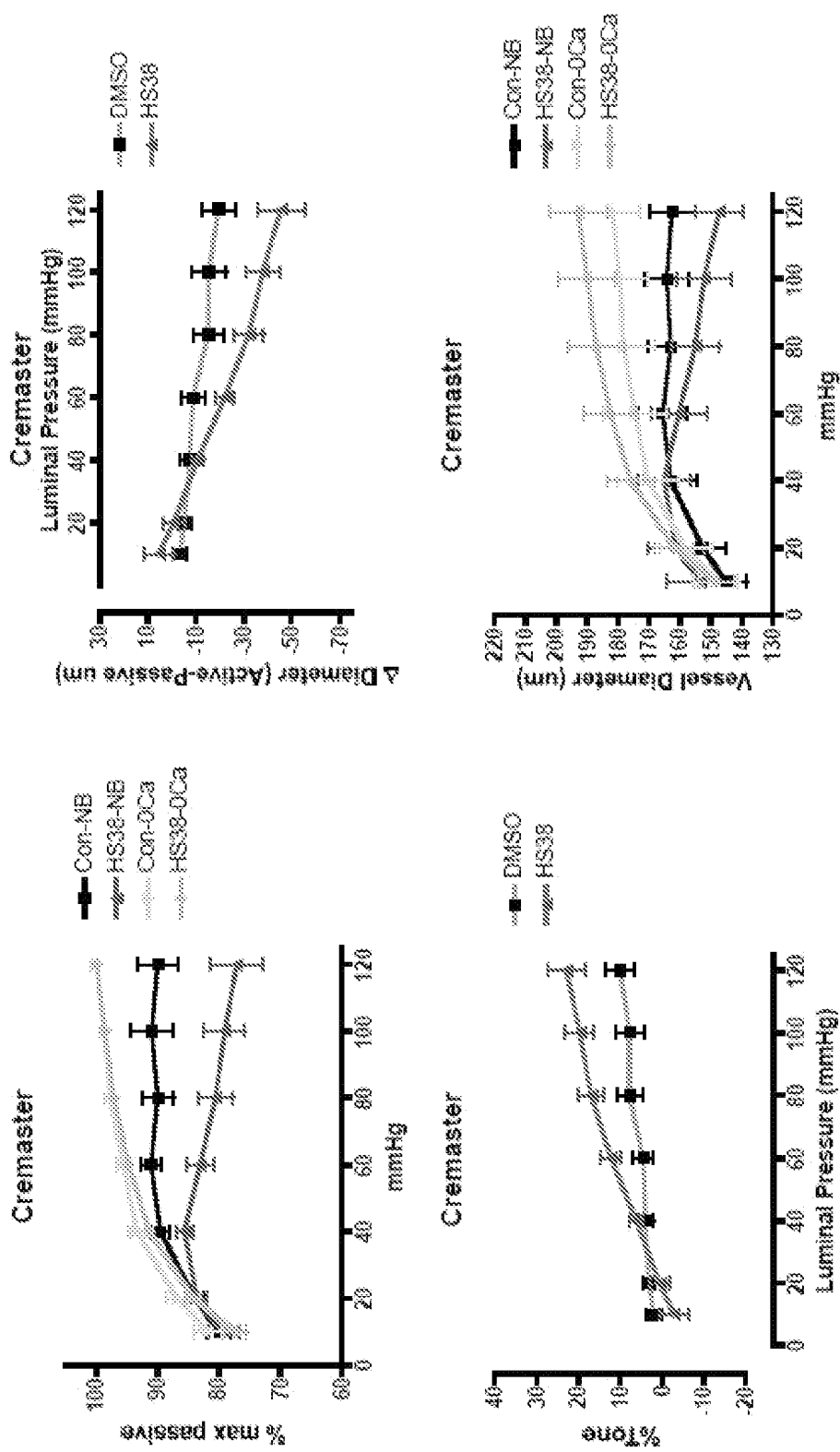
FIG. 43 are graphs of percent maximum passive versus pressure, change in diameter versus pressure, percent tone versus pressure, and vessel diameter versus pressure to show the effects of HS-38 dosing on the resistance vessel contractile responses to pressure for male 18-week Goto-Kakizaki rats.
Figure 44:
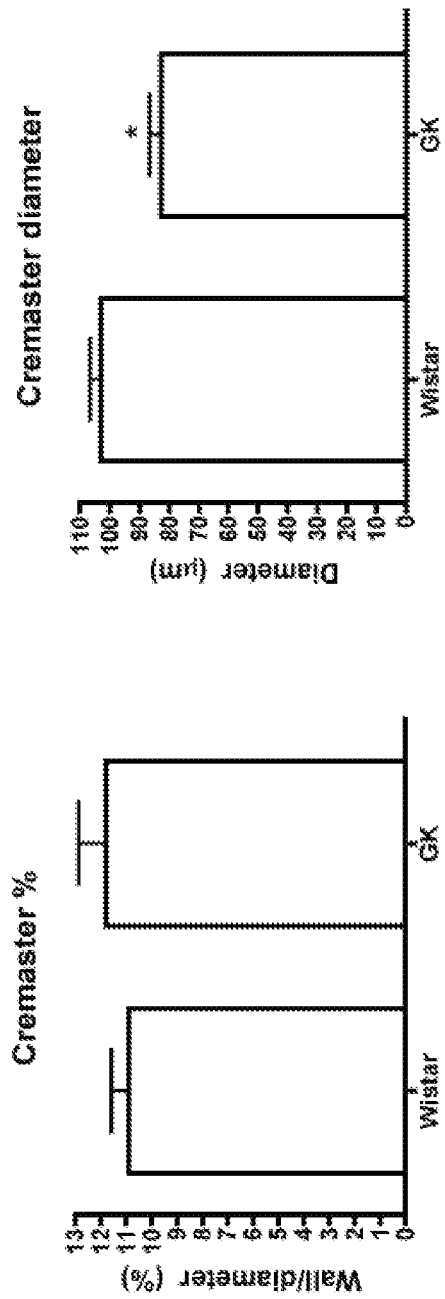
FIG. 44 are graphs of wall/diameter, diameter, and wall thickness for cremaster for Wistar Kyoto rats and Goto-Kakizaki rats.
Figure 44:
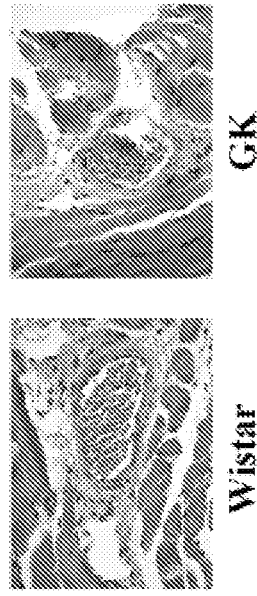
Figure 44:
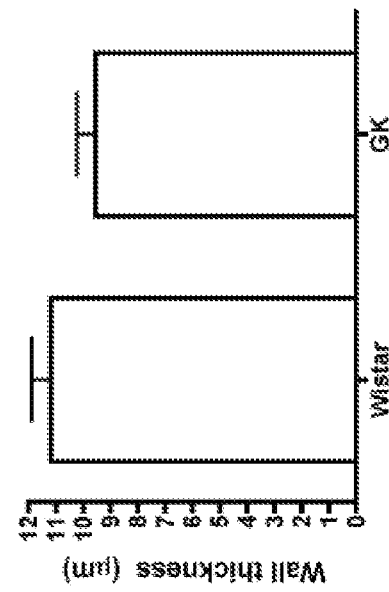
Figure 45:
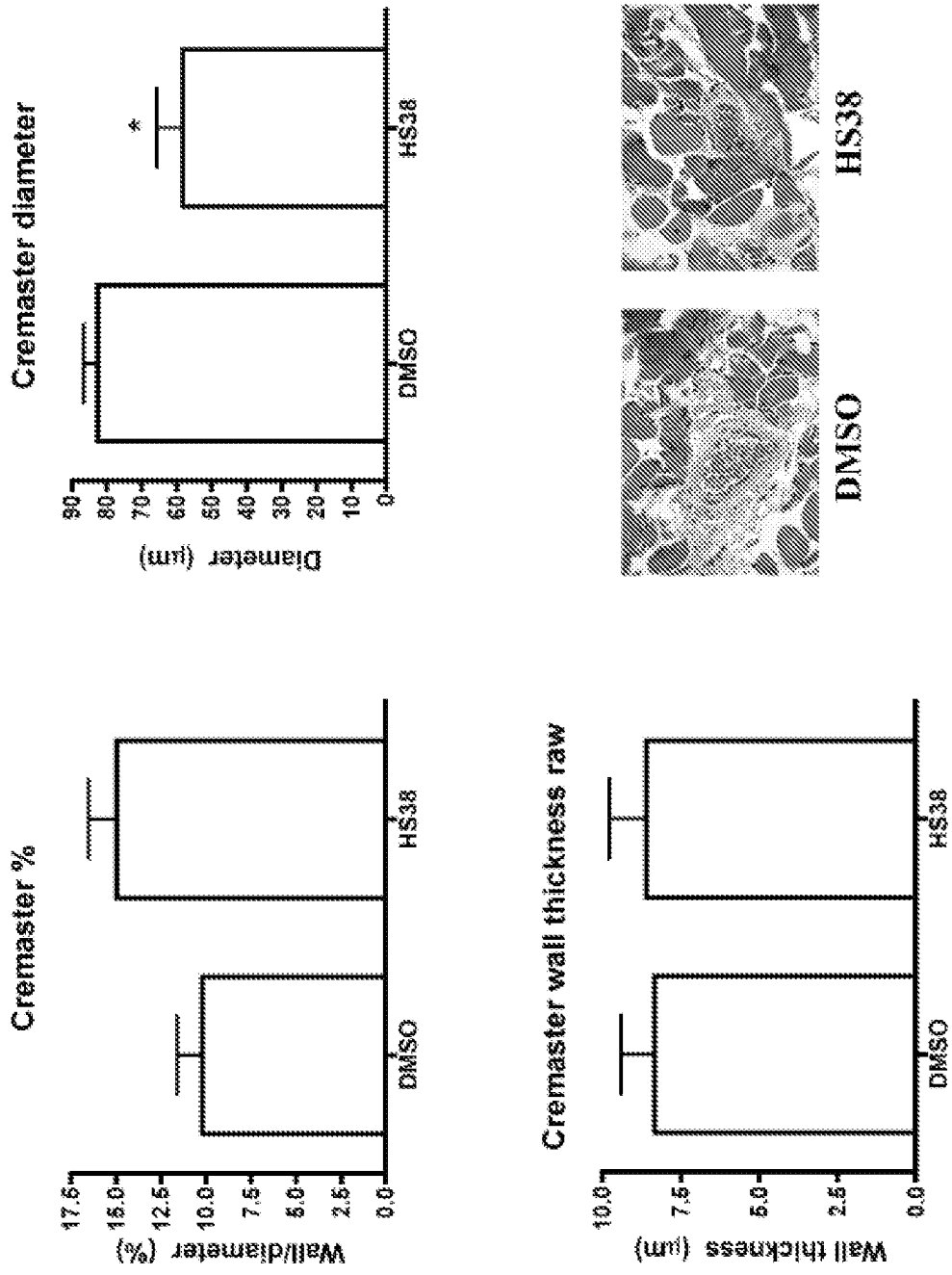
FIG. 45 are graphs of wall/diameter, diameter, and wall thickness for cremaster for DMSO (control) and HS-38-treated 10 week Goto-Kakizaki rats.
Figure 46:
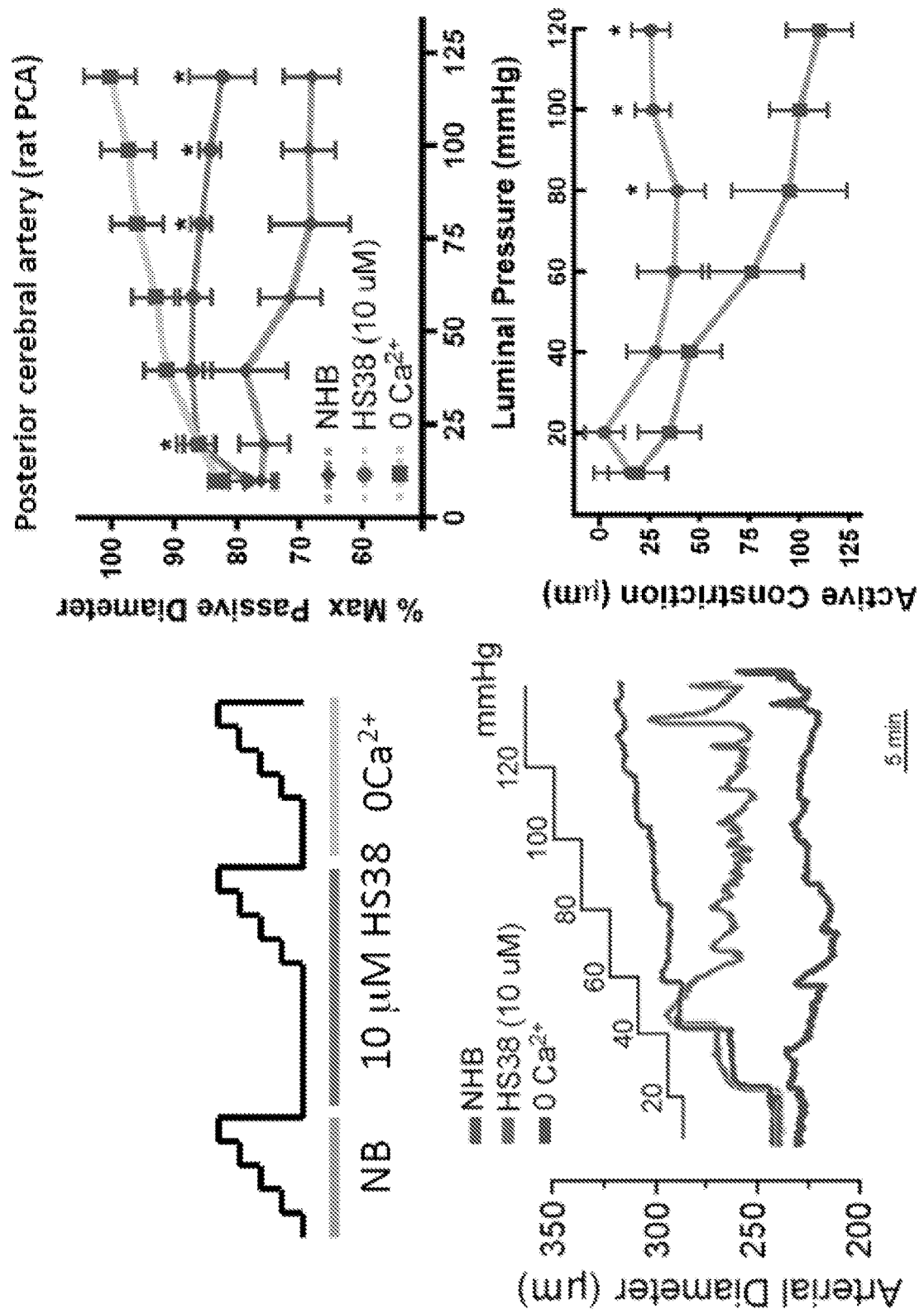
FIG. 46 are graphs of arterial diameter for various pressures, pressure versus percent maximal passive diameter, and pressure versus active constriction with HS-38 treatment.

Results from studies with the GK rat model of type 2 diabetes are shown in FIGS. 39-46. FIG. 39 shows results from male GK rats at 10 weeks, early stage, with a 6-week dosing regimen. Shown in FIG. 40 are the effects of HS-38 dosing on the resistance vessel contractile responses to pressure for male 10-week GK rats. Shown in FIG. 41 are the effects of HS-38 dosing on resistance vessel wall dynamics for male 10-week GK rats. FIG. 42 shows results from male GK rats at 18 weeks, late stage, with a 6-week dosing regimen. Shown in FIG. 43 are the effects of HS-38 dosing on the resistance vessel contractile responses to pressure for male 18-week GK rats.

Example 23. Effect on "Naïve" Middle/Posterior Cerebral Arteries in Rat

Figure 47:
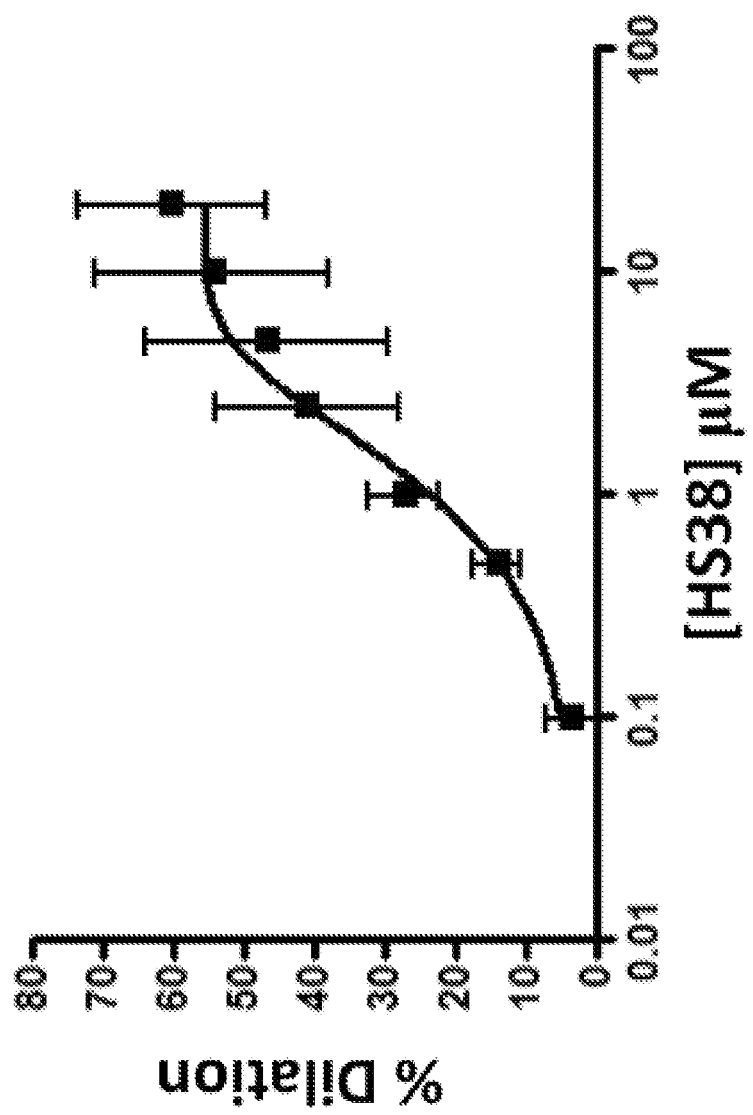
FIG. 47 is a graph of HS-38 concentration versus percent dilation of isolated PCA vessels (posterior cerebral artery of the rat) previously constricted with 5HT.

As shown in FIG. 47, ZIPK expression differences within different vascular beds may provide distinct pharmacology. ZIPK contributed to the normal cerebral myogenic response, and as shown in FIG. 48, extralumen application of the ZIPK inhibitor HS-38 suppressed the development of myogenic tone. As shown in FIG. 49, application of HS-38 induced dilation of isolated PCA vessels (posterior cerebral artery of the rat) previously constricted with 5HT.

Example 24. Effect on Human Cerebral Vessels

Tissues were obtained from patients undergoing resections for treatment for epilepsy or tumors. Surface vessels of ~200 µm diameter were analyzed by pressure myography and western immunoblotting. As shown in FIG. 50, and also FIG. 20D and FIG. 20A, ex vivo application of HS-38 suppressed myogenic tone of human cerebral vessels.

While the disclosure has been described in detail and with reference to specific embodiments thereof, it will be apparent to one skilled in the art that various changes and modifications can be made without departing from the spirit and scope of the disclosure.

The invention claimed is:
1. A compound of formula

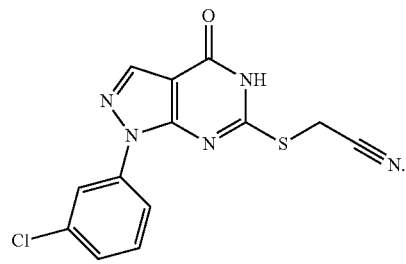 [SMILES: N#CCSc1nc2c(cnn2-c2cccc(Cl)c2)c(=O)[nH]1]

2. A pharmaceutical composition comprising the compound of claim 1 and a pharmaceutically acceptable carrier.

3. A method of treating hypertension in a subject in need of treatment, comprising administering to the subject a therapeutically effective amount of the compound of claim 1.

4. A method of treating pulmonary hypertension in a subject in need of treatment, comprising administering to the subject a therapeutically effective amount of the compound of claim 1.

5. A method of treating pre-eclampsia in a subject in need of treatment, comprising administering to the subject a therapeutically effective amount of the compound of claim 1.

6. A compound of formula

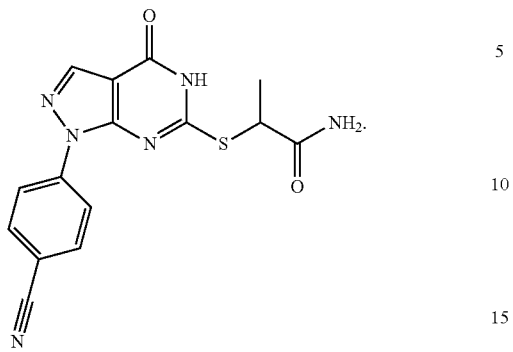

7. A pharmaceutical composition comprising the compound of claim 6 and a pharmaceutically acceptable carrier.

8. A method of treating breast cancer in a subject in need of treatment, comprising administering to the subject a therapeutically effective amount of the compound of claim 6.

9. A method of treating myeloma in a subject in need of treatment, comprising administering to the subject a therapeutically effective amount of the compound of claim 6.

10. A method of treating leukemia in a subject in need of treatment, comprising administering to the subject a therapeutically effective amount of the compound of claim 6.

11. A method of treating prostate cancer in a subject in need of treatment, comprising administering to the subject a therapeutically effective amount of the compound of claim 6.

* * * * *